(12) United States Patent
Hanlon et al.

(10) Patent No.: US 10,017,749 B2
(45) Date of Patent: Jul. 10, 2018

(54) MUTANT TRANSAMINASES AS WELL AS METHODS AND USES RELATING THERETO

(71) Applicant: Hoffmann-La Roche Inc., Little Falls, NJ (US)

(72) Inventors: Steven Paul Hanlon, Oberwil (CH); Hans Iding, Rheinfelden (CH); Paul Spurr, Riehen (CH); Beat Wirz, Reinach (CH); Uwe Bornscheuer, Greifswald (DE); Ioannis Pavlidis, Greifswald (DE); Martin Steffen Weiss, Greifswald (DE)

(73) Assignee: HOFFMAN-LA ROCHE INC., Little Falls, NJ (US)

( * ) Notice: Subject to any disclaimer, the term of this patent is extended or adjusted under 35 U.S.C. 154(b) by 0 days.

(21) Appl. No.: 15/130,030

(22) Filed: Apr. 15, 2016

(65) Prior Publication Data

US 2016/0304843 A1    Oct. 20, 2016

(30) Foreign Application Priority Data

Apr. 16, 2015    (EP) .................................... 15001113

(51) Int. Cl.
| | |
|---|---|
| *C12N 1/16* | (2006.01) |
| *C12N 1/20* | (2006.01) |
| *C12N 9/10* | (2006.01) |
| *C12P 13/00* | (2006.01) |

(52) U.S. Cl.
CPC ............. *C12N 9/1096* (2013.01); *C12N 1/16* (2013.01); *C12N 1/20* (2013.01); *C12P 13/001* (2013.01); *C07K 2319/00* (2013.01); *C07K 2319/21* (2013.01); *C12Y 206/01* (2013.01)

(58) Field of Classification Search
None
See application file for complete search history.

(56) References Cited

U.S. PATENT DOCUMENTS

2016/0304843 A1*    10/2016    Hanlon ................ C12P 13/001

FOREIGN PATENT DOCUMENTS

WO    2010/099501 A2    2/2010

OTHER PUBLICATIONS

International Search Report for PCT/EP2016/058051.
Other Database,Database UniProt [Online] retrieved from EBI accession No. UNIPROT: A0A061M288 sequence Sep. 3, 2014.
Wang et al., "Enhanced transaminase activity of bifunctional L-aspartate 4-decarboxylase" Biochemical and Biophysical Research Communication 356:368-373 ( 2007).

\* cited by examiner

*Primary Examiner* — Richard C Ekstrom
(74) *Attorney, Agent, or Firm* — Bonny G. Yeung

(57) ABSTRACT

The present invention relates to a mutant transaminase with increased transaminase activity relative to the wild-type transaminase, a fusion protein comprising the transaminase, a polynucleotide coding for the transaminase, a host cell comprising the polynucleotide, mutant transaminase and/or fusion protein, a method of producing an amine with the mutant transaminase or fusion protein and the use of the mutant transaminase or fusion protein for the production of an amine.

20 Claims, 5 Drawing Sheets

Figure 1:
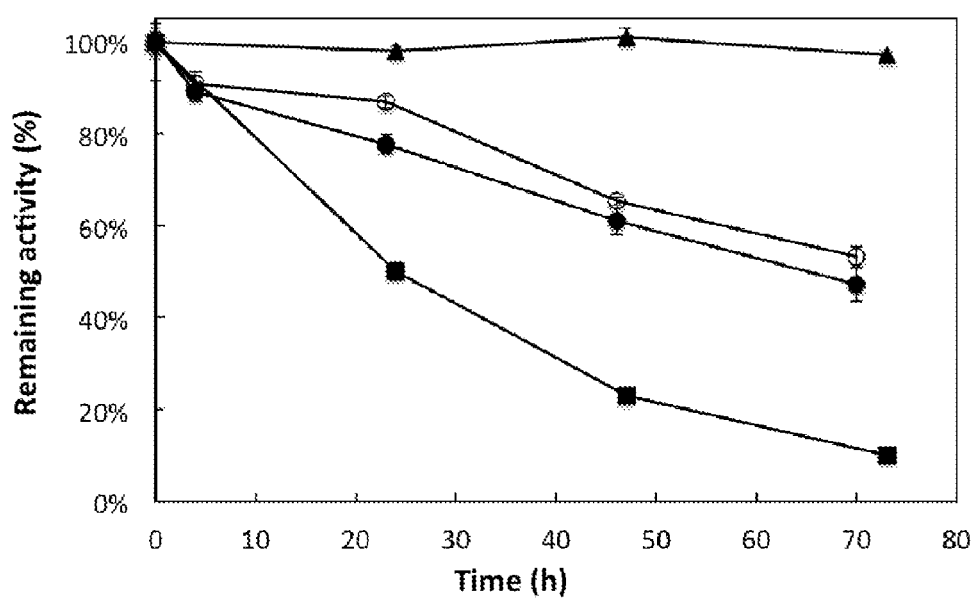

```
  1  ML-----KNDQLDQWDRDNFFHPSTHLAQHARGESANRVIKTASGVFIEDRDGTKLLDAFAGLYCVNVGYGRQEIAEAIADQ   77
  1  ML----nQSNELNAWDRDHFFHPSTHMGTHARGESPTRIMAGGEGVTVWDNNGRKSIDAFAGLYCVNVGYGRQKIADAIATQ   78
  1  ML-----KNDPLEQWDRDHFLHPSTHLAEFARGNVAHRLVSGGEGSHLVDRNGTRLLDGFAGLYCVNVGYGRREIADAIAKQ   77
  1  ML     TNDQLSQWDQDHFFHPSTALGAHARGEAPGMVVQTAEGCHITDRNGNRMLDAFAGLYCVNIGYGRQEVAEAIAAQ   77
  1  MLdhpapASNAFDSWDRDHFFHPSTHMGQHARGETPNRIITGAEGVYIVDREGRRSLDAFGGLYCVNVGYGRSKITDAIAEQ   82
  1  ML-----RNDQLAEWDRENFFHASTHLAAHARGDTPTRIITGGEGVYIQDRDGAKILDGFAGLYCVNVGYGRREITDAIAAQ   77
  1  ML-----TNDQLDRFDRENFFHPSTHLAQHARGESPSRIVKTAKGVFIEDRDGNKLLDGFGGLYCVNVGYGQESIIEAIAEQ   77
  1  ML-----KNDQLDQWDRENFFHPSTHLAQHARGDSANRVIKTASGVFIEDRDGNKLLDAFAGLYCVNVGYGRQEIADAIADQ   77
  1  ML-----TNDQLSQWDRENFFHPSTHLAQHARGETATRVTTTGQGCHIEDRDGTKLLDAFAGLYCVNVGYGRTEIADAIAAQ   77

78  ARELAYYHSYVGHGTEASITLAKMILDRAPKNMSKVYFGLGGSDANETNVKLIWYYNNILGRPEKKKIISRWRGYHGSGL   157
 79  AKNLAYYIAYVGHGTEASITLAKMIIDRAPKGMSRVYFGLSGSDANETNIKLIWYYNNVLGRPEKKKIISRWRGYIIGSGV   158
 78  ARELSYYHSYVGHGTEASVTLAHMILERAPANMSKVFFGLGGSDANETNIKLIWYMNNILGRPGKKKIISRWRGYHGSGL   157
 78  ARELAYYHSYMGNGTEASITLAKMVTERAPEGMNRVYFGQGGSDANETNIKLVWYYNNILGRPEKKKIVSRWRGYHGSGL   157
 83  ASKLAYYHAYAGHGSEPS-RLARMVIERAPAGMSRVFFGLGGSDANETNIKLVWYINNVLGRPQKKKIISRWRGYHGSGV   162
 78  VSELSYYHAYAGHGTEASVTLAKMVLDRAPDNMSKVYFGLGGSDANETNIKLIWYYNNILGRPEKKKIISRWRGYHGSGL   157
 78  AKELAYYHAYAGHGTEASINLAKMVIDRAPDHMSKVYFGLSGSDANETNIKLIWYYNNILGRPEKKKIISRWRGYHGSGL   157
 78  AKDLAYYHSYVGHGTEASITLAKMILDRAPANMSKVYFGLSGSDANETNVKLIWYYNNILGRPEKKKIISRWRGYHGSGL   157
 78  AKELAYYHAYVGHGTEASITLSKMILDRAPAHMSKVYFGLSGSDANETNIKLIWYYNNILGRPEKKKIISRWRGYHGSGL   157

158  VTGSLTGLEFHKKFDLPVEQVIHTEAPYYFRREDLNQIEEQFVAHCVAELEALIEREGADTIAAFIGEPILGTGGIVPP   237
159  MTGSLTGLDLFHNAFDLPRAPVLHTEAPYYFRRTDRSMSEEQFSQHCADKLEEMILAEGPETIAAFIGEPILGTGGIVPP   238
158  MSGSLTGLPLFHKAFDLPLAPILHTEAPYYRRPNADMSEEAFSAWCASELEAMIQREGPDTIAAFWAEPVLGTGGIVPP   237
158  MSGSLTGLSLFIRKFDLPLDKVLHTTAPYYFQRENVAQSEQEFTAQCVADLEELIAREGADTIAAFIAEPVIGTGGIVPP   237
163  MTGSLTGLAGFHKLFDLPRAPILHTEAPYYFRREDRSMSEEQFSQHCADRLEEMILPEGADTIAAFIGEPVLGTGGIVPP   242
158  MTGSLTGLGLFHAKFDLPMDGVLHTEAPHYLHRADRNQIEEQFSAYCAAKLEEMILAEGPDTIAAFIGEPILGTGGIVPP   237
158  MTGSLTGLAGFQRKFDLPLERVFHTTAPYYYRRKDLAMSEADFVAHCVAELEMRIEREGADTIAAFIGEPVLGTGGIVPP   237
158  VTGSLTGLELFHKKFDLPVNQVIHTEAPYYFRRADPDQSEAQFVAHCAEELEALIEREGADTIAAFIGEPVLGTGGIVPP   237
158  MTGSLTGLELFHKKFDLPLAQVIHTEAPYYFRRPDLAMSEEAFSAYCAAELEQLIEREGADTIAAFIGEPVLGTGGIVPP   237

238  PAGYWEAIQTVLNKHDILLVADEVVTGFGRLGTMFGSDHYGLEPDIITIAKGLTSAYAPLSGSIVSDKVWKVLEQGTDEN   317
239  PAGYWEKIQAVLKKYDVLLVADEVVTGFGRLGTMFGSDHYGIKPDLITIAKGLTSAYAPLSGVIVADRVWQVLVQGSDKL   318
238  PEGYWAAIQEVLDRHDILLVADEVITGFGRLGTMFGSDHYGMKPDVITIAKGLTSAYAPLSGSVLSEKVWKVLEQGTDEM   317
238  PEGYWNAIQPVLKKHDILLIADEVITGFGRLGAMFGSPLYGIEPDIMTIAKGLTSAYAPLSGSIVHDRVWDVLARGTDEN   317
243  PAGYWPKIQAVLKKYDIMLIADEVVTGFGRLGSMFGSDHYGIEPDLITIAKGLTSAYAPLSGVIVSEKVWRVLEQGSDEF   322
238  PEGYWAAIQAVLRKYDILLVVDEVVTGFGRLGTMFGSEHYGLKADLITIAKGLTSAYAPLSGSIVSKKMWAVLEKGTDEN   317
238  PEGYWKAISAVLEKHDILLIADEVVTGFGRLGSMFGSDHYGLKPDLITIAKGLTSAYAPLSGTIVSDKVWKVLEQGTDEN   317
238  PAGYWAAVLRKHDILLLIADEVVTGFGRLGTMFGSDHYGIEADIITIAKGLTSAYAPLSGSIISDKVWKVLEQGTDEN   317
238  PKGYWEAIQPILEKHDILLVADEVVTGFGRLGTMFGSDHYGLKPDLITIAKGLTSAYAPLSGSIVGDKMWKVLEQGTDEN   317

318  GPIGHGWTYSAHPIGAAAGVANLKLLDELNLVSNAGEVGAYLNATMAEALSQHANVGDVRGEGLLCAVEFVKDRDSRT   395
319  GSLGHGWTYSAHPICVAAGVANLELIDEMDLVTNAGETGAYFRAELAKAVGGHKNVGEVRGDGMLAAVEFVADKEDRV   396
318  GAIGHGWTYSAHPICGAAAGVANLKLIDELGLIDNAAEVGAHLRAGMRDALGEHPNVGDIRGEGMLCAVELVSDRESKE   395
318  GPLGHGWTYSAHPIGAAAGVANLILLDTLGLVDNAADVGFYLTAQMRAAMQDHAHVGDIRGVGMLTAVELVADREKGSgvga 399
323  GPIGHGWTYSSHPLCTAAGVANLELVDELDLVTNARETGAYFNAALKDALSGHRHVGEVRGEGLLAAVELVRDREDRT   400
318  GAFGHGWTYSAHPIGAAAGVANLKLIDDLGLIANASETGAYLKSALQAALGDHPNVAEIRGEGMLAAVEFCADRDDLK   395
318  GPIGHGWTYSAHPIGAAAGVANLKLIDELGLVKNAAETGAYLRAAMKDALSDHPHVGDIRGEGMLMAVEFVKDRESRT   395
318  GPIGHGWTYSAHPIGAAAGVANLKLIDRLNLVQNAGETGAYLNATMTEALAGIPNVGEVRGAGMLCAVEFVKDKESRL   395
318  GPIGHGWTYSAHPIGAAAGVANLKLIDDMNLVANAGETGAHFRKAMTDALGDHAKVGDIRGEGMLCAVELVDDKDNRT   395

396  FFDAADKIGPQISAKLLEQDKIIARAMPQGDILGFAPPFCLTRAEADQVVEGTLRAVKAV---LG   457   SEQ ID NO: 1
397  FFDASQKIGPQVATALAASG VIGRAMPQGDILGFAPPLCLTREQADIVVSKTADAVKSVfanL   459   SEQ ID NO: 3
396  GFDPSRKVTVNAVAHLMENG-VIGRAMPHSETIGFAPPFCLTRDEADEIVAKIAAAVKAV---LG   456   SEQ ID NO: 5
400  GFDPAAKIVPQISAAMAKRG-VIARAMPQADIVGFSPPLCLTRAEADTIVSVIAEAVAEV---LG   460   SEQ ID NO: 6
401  FFEASEKVGPRVAAAMLERG-VIARAMPQGDILGFAPPLCLTREEADIVVDATRGAVEAVcatLG   464   SEQ ID NO: 7
396  QFDTSATIGPRLAAELLTRG-VIGRAMPQSDTIGFAPPLCLTRAEVDQIVAAMKGAVDAV---LPa 457   SEQ ID NO: 8
396  FYDPSEKVGPNLAAALISEG-VIARAMPEGDILGYAPPLCLTREEADQIVAATKKAVIAV---LG   456   SEQ ID NO: 9
396  FFDAADKIGPQISAKLLEQDKVIARAMPQGDILGFAPPFCLSRAEADQVVDATLRAVRTV---LG   457   SEQ ID NO:10
396  FFDPSQKVGAQIASALLSKG-VIARAMPQGDILGFAPPLCLTPAEAEEVATKTGEAVRDV---LG   456   SEQ ID NO:11
```

*FIG. 2*

```
  1  ML-----KNDQLDQWDRDNFFHPSTHLAQHARGESANRVIKTASGVFIEDRDGTKLLDAFAGLWCVNVGYGRQEIAEAIADQ   77
  1  ML----nQSNELNAWDRDHFFHPSTHMGTHARGESPTRIMAGGEGVTVWDNNGRKSIDAFAGLWCVNVGYGRQKIADAIATQ   78
  1  ML-----KNDPLEQWDRDHFLHPSTHLAEFARGNVAHRIVSGGEGSHIVDRNGTRLLDGFAGLWCVNVGYGRREIADAIAKQ   77
  1  ML-----TNDQLSQWDQDHFFHPSTALGAHARGEAPGMVVQTAEGCHITDRNGNRMLDAFAGLWCVNIGYGRQEVAEAIAAQ   77
  1  MLdhpapASNAFDSWDRDHFFHPSTHMGQHARGETPNRIITGAEGVYIVDREGRRSLDAFGGLWCVNVGYGRSKITDAIAEQ   82
  1  ML-----RNDQLAEWDRENFFHASTHLAAHARGDTPTRIITGGEGVYIQDRDGAKLLDGFAGLWCVNVGYGRRETTDAIAAQ   77
  1  ML-----TNDQLDRFDRENFFHPSTHLAQHARGESPSRIVKTAKGVFIEDRDGNKLLDGFGGLWCVNVGYGQESIIEAIAEQ   77
  1  ML-----KNDQLDQWDRENFFHPSTHLAQHARGDSANRVIKTASGVFIEDRDGNKLLDAFAGLWCVNVGYGRQEIADAIADQ   77
  1  ML     TNDQLSQWDRENFFHPSTHLAQHARGETATRVITTGCGCHIEDRDGTKLLDAFAGLWCVNVGYGRTEIADAIAAQ   77

78  ARELAYYHSFVGHGTEASIPLAKMILDRAPKNMSKVYFGLGGSDANETNVKLIWYYNNILGRPEKKKIISRWRGFHGSGL  157
 79  AKNLAYYHAFVGHGTEASITLAKMIIDRAPKGMSRVYFGLSGSDANETNIKLIWYYNNVLGRPEKKIISRWRGFHGSGV  158
 78  ARELSYYHSFVGHGTEASVPLAHMILERAPANMSKVFFGLGGSDANETNIKLIWYMNNILGRPGKKKIISRWRGFHGSGL  157
 78  ARELAYYHSFMGNGTEASIPLAKMVTERAPEGMNRVYFGQGGSDANETNIKLVWYYNNILGRPEKKKIVSRWRGFHGSGL  157
 83  ASKLAYYHAFAGHGSEPSIRLARMVIERAPAGMSRVFFGLSGSDANETNIKLVWYINNVLGRPQKKKILSRWRGFHGSGV  162
 78  VSELSYYHAFAGHGTEASVPLAKMVLDRAPDNMSKVYFGLGGSDANETNIKLIWYYNNILGRPEKKKIISRWRGFHGSGL  157
 78  AKELAYYHAFAGHGTEASINLAKMVIDRAPDHMSKVYFGLGGSDANETNIKLIWYYNNILGRPEKKKIISRWRGFHGSGL  157
 78  ARELAYYHSFVGHGTEASIPLAKMILDRAPANMSKVYFGLGGSDANETNVKLIWYYNNILGRPEKKKIISRWRGFHGSGL  157
 78  AKELAYYHAFVGHGTEASITLSKMILDRAPAHMSKVYFGLSGSDANETNIKLIWYYNNILGRPEKKKIISRWRGFHGSGL  157

158  VTGSLTGLELFHKKFDLPVEQVIHTEAPYYFRREDLNQTEEQFVAHCVAELEALIEREGADTIAAFIGEPILGAGGIVPP  237
159  MTGSLTGLDLFHNAFDLPRAPVLHTEAPYYFRRTDRSMSEEQFSQHCADKLEEMILAEGPETIAAFIGEPILGAGGIVPP  238
158  MSGSLTGLPLFHKAFDLPLAPILHTEAPYYYRRPNADMSEEAFSAWCASELEAMIQREGPDTIAAFWAEPVLGAGGIVPP  237
158  MSGSLTGLSLFHRKFDLPLDKVLHTTAPYYFQRENVAQSEQEFTAQCVADLEELIAREGADTIAAFIAEPVIGAGGIVPP  237
163  MTGSLTGLAGFHKLFDLPRAPLLHTEAPYYFRREDRSMSEEQFSQHCADRLEEMILTEGADTIAAFIGEPILGAGGIVPP  242
158  MTGSLTGLGLFHAKFDLPMDGVLHTEAPHYLHRADRNQTEEQFSAYCAAKLEEMILAEGPDTIAAFIGEPILGAGGIVPP  237
158  MTGSLTGLAGFQRKFDLPLERVFHTTAPYYYRRKDLAMSEADFVAHCVAELEMRIEREGADTIAAFIGEPVLGAGGIVPP  237
158  VTGSLTGLELFHKKFDLPVNQVIHTEAPYYFRRADPDQSEAQFVAHCAAELEALIEREGADTIAAFIGEPVLGAGGIVPP  237
158  MTGSLTGLELFHKKFDLPLAQVIHTEAPYYFRRPDLAMSEEAFSAYCAAELEQLIEREGADTIAAFIGEPVLGAGGIVPP  237

238  PAGYWEATQTVLNKHDILLVADEVVTGFGRLGTMFGSDHYGLEPDITTIAKGLTSAYAPLSGSIVSDKVWKVLEQGTDEN  317
239  PAGYWEKIQAVLKKYDVLLVADEVVTGFGRLGTMFGSDHYGIKPDLITIAKGLTSAYAPLSGVIVADRVWQVLVQGSDKL  318
238  PEGYWAAIQEVLDRHDILLVADEVITGFGRLGTMFGSDHYGMKPDVITIAKGLTSAYAPLSGSVLSEKVWKVLEQGTDEM  317
238  PEGYWNAIQPVLKRHDILLLADEVITGFGRLGAMFGSPLYGIEPDIMTIAKGLTSAYAPLSGSIVHDRVWDVLARGTDEN  317
243  PAGYWPKIQAVLKKYDIMLEADEVVTGFGRLGSMFGSDHYGIEPDLITIAKGLTSAYAPLSGVIVSEKVWRVLEQGSDEF  322
238  PKGYWEALQAVLRKYDILLVVDEVVTGFGRLGSEHYGLKADLITIAKGLTSAYAPLSGSIVSKKMWAVLEKGTDEN  317
238  PEGYWKASAVLEKHDILLLADEVVTGFGRLGSMFGSDHYGLKPDLITIAKGLTSAYAPLSGTIVSDKVWKVLEQGTDEN  317
238  PAGYWEAIQAVLRKHDILLLADEVVTGFGRLGTMFGSDHYGIEADIITIAKGLTSAYAPLSGSIISDKVWKVLEQGTDEN  317
238  PKGYWEAIQPILEKHDILLVADEVVTGFGRLGTMFGSDHYGLKPDLITIAKGLTSAYAPLSGSIVGDKMWKVLEQGTDEN  317

318  GPIGHGWTYSAHPIGAAAGVANLKLLDELNLVSNAGEVGAYLNATMAEALSQHANVGDVRGEGLLCAVEFVKDRDSRT  395
319  GSLGHGWTYSAHPICVAAGVANLELIDEMDLVTNAGETGAYFRAELAKAVGHIKNVGEVRGDGMLAAVEFVADKDDRV  396
318  GPIGHGWTYSAHPIGAAAGVANLKLIDELGLIDNAAEVGAHLRAGMRDALGEHPNVGDIRGEGMLCAVELVSDRESKE  395
318  GPLGHGWTYSAHPIGAAAGVANLTLLDTLGLVDNAADVGPYLTAQMRAAMQDHAHVGDIRGVGMLTAVELVADRDKGSgvga  399
323  GPIGHGWTYSSHPLCTAAGVANLELVDELDLVTNARETGAYFNAALKDALSGHRHVGEVRGEGLLAAVELVRDRDDRT  400
318  GAFGHGWTYSAHPIGAAAGVANLKLIDDLGLIANASETGAYLKSALQAALGDHPNVAEIRGEGMLAAVEFCADRDDLK  395
318  GPIGHGWTYSAHPIGAAAGVANLKLIDELGLVKNAAETGAYLRAAMKDALSDHPHVGDIRGEGMLMAVEFVKDRESRT  395
318  GPIGHGWTYSAHPIGAAAGVANLKLIDRLNLVQNAGETGAYLNATMEEALAGHPNVGVRGAGMLCAVEFVKDKDSRL  395
318  GPIGHGWTYSAHPIGAAAGVANLKLIDDMNLVANAGETGAHFRKAMTDALGDHAKVGDIRGEGMLCAVELVDDKDNRT  395

396  FFDAADKIGPQISAKLLEQDkIIARAMPQGDILGFAPPFCLTRAEADQVVEGTLRAVKAV---LG  457   SEQ ID NO: 30
397  FFDASQKIGPQVATALAASG-VIGRAMPQGDILGFAPPLCLTREQADIVVSKTADAVKSVfanL  459   SEQ ID NO: 31
396  GFDPSRKVTVNAVAHLMENG-VIGRAMPHSETIGFAPPFCLTRDEADEIVAKTAAAVKAV---LG  456   SEQ ID NO: 32
400  GFDPAAKIVPQISAAMAKRG-VIARAMPQADIVGFSPPLCLTRAEADTIVSVTAEAVAEV---LG  460   SEQ ID NO: 33
401  FFEASEKVGPRVAAAMLERG-VIGRAMPQGDILGFAPPLCLTREEADIVVDATRGAVEAVcatLG  464   SEQ ID NO: 34
396  QFDTSATIGPRLAAFLLTRG-VIGRAMPQSDTIGFAPPLCITRAEVDQIVAAMKGAVDAV---LPa 457   SEQ ID NO: 35
396  FYDPSEKVGPNLAAALISEG-VIARAMPEGDILGFAPPLCLTREEADQIVAATKKAVIAV---LG  456   SEQ ID NO: 36
396  FFDAADKIGPQISAKLLEQDkVIARAMPQGDILGFAPPFCLSRAEADQVVDATLRAVRTV---LG  457   SEQ ID NO: 37
396  FFDPSQKVGAQIASALLSKG-VIARAMPQGDILGFAPPLCLTPAEAEEVATKTGEAVRDV---LG  456   SEQ ID NO: 38
```

FIG. 3

FIG. 4

```
  1 ML-----KNDQLDQWDRDNFFHPSTHLAQHARGESANRVIKTASGVFIEDRDGTKLLDAFAGLWCVNVGYGRQEIAEAIADQ   77
  1 ML----nQSNELNAWDRDHFFHPSTHMGTHARGESPTRIMAGGEGVTVWDNNGRKSIDAFAGLWCVNVGYGRQKIADAIATQ   78
  1 ML-----KNDPLEQWDRDIIFLIIPSTIILAEFARGNVAIIRIVSGGEGSIIIVDRNGTRLLDGFAGLWCVNVGYGRREIADAIAKQ   77
  1 ML-----TNDQLSQWDQDIIFFIIPSTALGAIIARGEAPGMVVQTAEGCIIITDRNGNRMLDAFAGLWCVNIGYGRQEVAEAIAAQ   77
  1 MLdhpapASNAFDSWDRDHFFHPSTHMGQHARGETPNRLITGAEGVYIVDREGRRSLDAFGGLWCVNVGYGRSKITDAIAEQ    82
  1 ML-----RNDQLAEWDRENFFHASTHLAAHARGDTPTRIITGGEGVYIQDRDGAKILDGFAGLWCVNVGYGRREITDAIAAQ   77
  1 ML-----TNDQLDRFDRENFFHPSTHLAQHARGESPSRIVKTAKGVFIEDRDGNKLLDGFGGLWCVNVGYGQESIIEAIAEQ   77
  1 ML-----KNDQLDQWDRENFFHPSTHLAQHARGDSANRVIKTASGVFIEDRDGNKLLDAFAGLWCVNVGYGRQEIADAIADQ   77
  1 ML-----TNDQLSQWDRENFFHPSTHLAQHARGETATRVITTGQGCHIEDRDGTKLLDAFAGLWCVNVGYGRTEIADAIAAQ   77

78 ARELAYYHSFVGHGTEASITLAKMILDRAPKNMSKVYFGLGGSDANETNVKLIWYYNNILGRPEKKKILSRWRGFHGSGL   157
 79 AKNLAYYHAFVGHGTEASITLAKMILDRAPKGMSRVYFGLSGSDANETNIKLIWYYNNVLGRPEKKKILSRWRGFHGSGV   158
 78 ARELSYYHSFVGHGTEASVTLAHMILERAPANMSKVFFGLGGSDANETNIKLIWYMNNILGRPGKKKIISRWRGFHGSGL   157
 78 ARELAYYHSFMGNGTEASITLAKMVTERAPEGMNRVYFGQGGSDANETNIKLVWYYNNILGRPEKKKIVSRWRGFHGSGL   157
 83 ASKLAYYHAFAGHGGSEPSIRLARMVIERAPAGMSRVFFGLSGSDANETNIKLVWYINNVLGRPQKKKILSRWRGFIGSGV   162
 78 VSELSYYHAFAGHGTEASVTLAKMVLDRAPDNMSKVYFGLSGSDANETNIKLIWYYNNVLGRPEKKKILSRWRGFHGSGL   157
 78 AKELAYYHAFAGHGTEASINLAKMVIDRAPDHMSKVYFGLSGSDANETNIKLIWYYNNILGRPEKKKILSRWRGFHGSGL   157
 78 ARELAYYHSFVGHGTEASITLAKMILDRAPANMSKVYFGLGGSDANETNVKLIWYYNNILGRPEKKKIISRWRGFHGSGL   157
 78 AKELAYYHAFVGHGTEASITLSKMILDRAPAHMSKVYFGLSGSDANETNIKLIWYYNNILGRPEKKKIISRWRGFHGSGL   157

158 VTGSLTGLELFHKKFDLPVEQVIHTEAPYYFRREDLNQTEEQFVAIICVAELEALIEREGADTIAAFIGEPILGAGGMVPP   237
159 MTGSLTGLDLFHNAFDLFRAPVLHTEAPYYFRRTDRSMSEEQFSQHCADKLEEMLAEGPETIAAFIGEPILGAGGMVPP   238
158 MSGSLTGLPLFHKAFDLFLAPILHTEAPYYYRRPNADMSEEAFSAWCASELEAMIQREGPDTIAAFWAEPVLGAGGMVPP   237
158 MSGSLTGLSLFHRKFDLPLDKVLHTTAPYYFQRENVAQSEQEFTAQCVADLEELIAREGADTIAAFIAEPVLGAGGMVPP   237
163 MTGSLTGLAGFHKLFDLPRAPILHTEAPYYFRREDRSMSEEQFSQHCADRLEEMILTEGADTIAAFIGEPVLGAGGMVPP   242
158 MTGSLTGLGLFHAKFDLPMDGVLHTEAPHYLIIRADRNQTEEQFSAYCAAKLEEMILAEGPDTIAAFIGEPILGAGGMVPP   237
158 MTGSLTGLAGFQRKFDLPLERVFHTTAPYYYRRKDLAMSEADFVAHCVAELEMRIEREGADTIAAFIGEPVLGAGGMVPP   237
158 VTGSLTGLELFHKKFDLFVNQVLHTEAPYYFRRADPDQSEAQFVAHCAAELEALIEREGADTIAAFIGEPVLGAGGMVPP   237
158 MTGSLTGLELFHKKFDLPLAQVLHTEAPYYFRRPDLAMSEEAFSAYCAAELEQLIEREGADTIAAFIGEPVLGAGGMVPP   237

238 PAGYWEAIQTVLNKHDILLVADEVVTGFGRLGTMFGSDHYGLEPDIITIAKGLTSAYAPLSGSIVSDKVWKVLEQGTDEN   317
239 PAGYWEKIQAVLKKYDVLLVADEVVTGFGRLGTMFGSDHYGIEKPDLITIAKGLTSAYAPLSGVIVADRVWQVLVQGSDKL   318
238 PEGYWAAIQEVLDRHDILLVADEVITGFGRLGTMFGSDHYGMKPDVITIAKGLTSAYAPLSGSVLSEKVWKVLEQGTDEM   317
238 PEGYWNAIQPVLKRIIDILLIADEVITGFGRLGAMFGSPLYGIEPDIMTIAKGLTSAYAPLSGSIVIIDRVWDVLARGTDEN   317
243 PAGYWPKIQAVLKKYDIMLIADEVVTGFGRLGSMFGSDHYGIEPDLITIAKGLTSAYAPLSGVIVSEKVWRVLEQGSDEF   322
238 PKGYWAAIQAVLRKYDILLVVDEVVTGFGRLGTMFGSEHYGLKADLITIAKGLTSAYAPLSGSIVSKKMWAVLEKGTDEN   317
238 PEGYWAAISAVLEKHDILLIADEVVTGFGRLGTMFGSDHYGLKPDLITIAKGLTSAYAPLSGTIVSDKVWKVLEQGTDEN   317
238 PAGYWEAIQAVLRKHDILLIADEVVTGFGRLGTMFGSDHYGIEADIITIAKGLTSAYAPLSGSIISDKVWKVLEQGTDEN   317
238 PKGYWEAIQPILEKIIDILLVADEVVTGFGRLGTMFGSDIIYGLKPDLITIAKGLTSAYAPLSGSIVGDKMWKVLEQGTDEN   317

318 GPIGHGWTYSAHPIGAAAGVANLKLLDELNLVSNAGEVGAYLNATMAIALSQHANVGDVRGEGLLCAVEFVKDRDSRT           395
319 GSLGHGWTYSAHPICVAAGVANLLELIDEMDLVTNAGETGAYFRAELAKAVGGHKNVGEVRGJGMLAAVEFVADKDRV           396
318 GAIGHGWTYSAHPIGAAAGVANLKLIDELGLIDNAAEVGAHLRAGMRDALGEHPNVGDIRGEGMLCAVELVSDRESKE           395
318 GPLGHGWTYSAHPIGAAAGVANLTLLDDLGLVDNAADVGPYLTAQMRAAMQDHAHVGDIRGVGMLTAVELVADRDKGSgvga    399
323 GPIIGHGWTYSSIIPLCTAAGVANLIELVDELDLVTNARETGAYFNAALKDALSGIIRIVGEVRGEGLLAAVELVRDRDDRT      400
318 GAFGHGWTYSAHPIGAAAGVANLKLIDDLGLIANASETGAYLKSALQAALGDIIPNVAEIRGEGMLAAVEFCADRDDLK         395
318 GPLGHGWTYSAHPIGAAAGVANLKLIDELGLVKNAAETGAYLRAAMKDALSDHPHVGDIRGEGMLMAVEFVKDRESRT          395
318 GPLGHGWTYSAHPIGAAAGVANLKLIDRLNLVQNAGETGAYLNATMTEALAGHPNVGEVRGEGMLCAVEFVKDKSRL           395
318 GPIGHGWTYSAHPIGAAAGVANLKLIDDMNLVANAGETGAHFRKAMTDALGDHAKVGDIRGEGMLCAVELVDDKDNRT          395

396 FFDAADKIGPQISAKLLEQDkIIARAMPQGDILGFAPPFCLTRAEADQVVEGTLRAVKAV     LG   457   SEQ ID NO: 53
397 FFDASQKIGPQVATALAASG-VIGRAMPQGDILGFAPPLCLTREQADIVVSKTADAVKSVfanL     459   SEQ ID NO: 55
396 GFDPSRKVTVNAVAHLMENG-VIGRAMPHSETIGFAPPFCLTRDEADEIVAKTAAAVKAV---LG   456   SEQ ID NO: 58
400 GFDPAAKIVPQISAAMAKRG-VIARAMPQADIVGFSPPLCLTRAEADTIVSVTAEAVAEV---LG   460   SEQ ID NO: 59
401 FFEASEKVGPRVAAAMLERG-VIARAMPQGDILGFAPPLCLTRREEADIVVDATRGAVEAVcatLG   464   SEQ ID NO: 60
396 QFDTSATIGPRLAAELLTRG-VIGRAMPQSDTIGFAPPLCITRAEVDQIVAAMKGAVDAV---LPa  457   SEQ ID NO: 61
396 FYDPSEKVGPNLAAALISEG-VIARAMPEGDILGYAPPLCLTREEADQIVAATKKAVIAV    LG   456   SEQ ID NO: 62
396 FFDAADKIGPQISAKLLEQDkVIARAMPQGDILGFAPPFCLSRAEADQVVDATLRAVRTV---LG   457   SEQ ID NO: 63
396 FFDPSQKVGAQIASALLSKG-VIARAMPQGDILGFAPPLCLTPAEAEEVATKTGEAVRDV---LG   456   SEQ ID NO: 64
```

FIG. 5

SEQUENCE LISTING

```
<160> NUMBER OF SEQ ID NOS: 64

<210> SEQ ID NO 1
<211> LENGTH: 457
<212> TYPE: PRT
<213> ORGANISM: Ruegeria sp. TM1040

<400> SEQUENCE: 1

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Tyr Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Tyr Val Gly His Gly Thr Glu Ala Ser Ile
            85                  90                  95
```

```
Thr Leu Ala Lys Met Ile Leu Asp Arg Ala Pro Lys Asn Met Ser Lys
                100                 105                 110

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
        130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
210                 215                 220

Gly Glu Pro Ile Leu Gly Thr Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
450                 455

<210> SEQ ID NO 2
<211> LENGTH: 1395
<212> TYPE: DNA
<213> ORGANISM: Artificial Sequence
<220> FEATURE:
<223> OTHER INFORMATION: Transaminase plus tag

<400> SEQUENCE: 2
```

-continued

| | |
|---|---|
| atgctgaaaa acgaccaact ggaccaatgg gaccgtgata acttcttcca cccgtcaacg | 60 |
| cacctggcgc aacatgcccg tggcgaatca gctaaccgtg tgatcaaaac cgcgtcgggc | 120 |
| gtttttattg aagatcgcga cggtacgaaa ctgctggatg ctttcgcggg cctgtattgc | 180 |
| gttaatgtcg gctacggtcg tcaggaaatt gccgaagcaa tcgctgatca agcgcgcgaa | 240 |
| ctggcctatt accatagcta tgtgggccac ggtaccgaag cttctatcac gctggcgaaa | 300 |
| atgattctgg atcgtgcccc gaaaaacatg agtaaagttt actttggtct gggcggttcc | 360 |
| gacgcaaacg aaaccaatgt caaactgatc tggtattaca caatattct gggccgcccg | 420 |
| gagaaaaaga aaattatcag tcgttggcgc ggttatcatg cagtggtct ggttaccggc | 480 |
| tccctgacgg gtctggaact gtttcataaa aaattcgatc tgccggtgga caggttatt | 540 |
| cacaccgaag ccccgtatta ctttcgtcgc gaagacctga accagacgga agaacaattc | 600 |
| gtcgcacact gtgtggctga actggaagcg ctgatcgaac gtgaaggcgc ggataccatt | 660 |
| gcggccttca tcggcgaacc gattctgggt acgggcggta ttgtgccgcc gccggccggt | 720 |
| tattgggaag caatccagac cgtcctgaat aaacatgata ttctgctggt tgcggacgaa | 780 |
| gtggttaccg gctttggtcg cctgggcacg atgttcggtt ctgatcacta tggcctggaa | 840 |
| ccggacatta tcaccatcgc gaaaggtctg acgtcagcgt acgccccgct gagcggttct | 900 |
| attgtgtcgg ataaagtctg gaaagtgctg gaacagggca ccgacgaaaa cggtccgatc | 960 |
| ggccatggtt ggacgtatag cgcacacccg attggtgcag ctgcaggtgt tgcaaatctg | 1020 |
| aaactgctgg atgaactgaa cctggttagc aatgccggcg aagtcggtgc ctacctgaac | 1080 |
| gcaaccatgg cagaagctct gtcccaacat gctaatgttg gcgatgtccg tggcgaaggt | 1140 |
| ctgctgtgcg cggtggaatt tgttaaagat cgtgacagcc gcacgttttt cgatgccgca | 1200 |
| gacaaaatcg gtccgcagat ttctgcgaaa ctgctggaac aagataaaat tatcgcgcgt | 1260 |
| gccatgccgc agggcgacat tctgggtttt gccccgccgt tctgtctgac ccgcgcagaa | 1320 |
| gctgatcaag tcgtggaagg tacgctgcgc gctgtcaaag ccgttctggg ttcacatcac | 1380 |
| catcaccacc actaa | 1395 |

<210> SEQ ID NO 3
<211> LENGTH: 459
<212> TYPE: PRT
<213> ORGANISM: Mesorhizobium loti maff303099

<400> SEQUENCE: 3

```
Met Leu Asn Gln Ser Asn Glu Leu Asn Ala Trp Asp Arg Asp His Phe
1               5                  10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Tyr Cys Val Asn Val
    50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Tyr Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125
```

Lys Leu Ile Trp Tyr Tyr Asn Asn Val Leu Gly Arg Pro Glu Lys Lys
130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
                180                 185                 190

Asp Arg Ser Met Ser Glu Glu Gln Phe Ser Gln His Cys Ala Asp Lys
                195                 200                 205

Leu Glu Glu Met Ile Leu Ala Glu Gly Pro Glu Thr Ile Ala Ala Phe
210                 215                 220

Ile Gly Glu Pro Ile Leu Gly Thr Gly Gly Ile Val Pro Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
                260                 265                 270

Phe Gly Ser Asp His Tyr Gly Ile Lys Pro Asp Leu Ile Thr Ile Ala
                275                 280                 285

Lys Gly Leu Thr Ser Ala Tyr Ala Pro Leu Ser Gly Val Ile Val Ala
290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
                340                 345                 350

Ala Gly Glu Thr Gly Ala Tyr Phe Arg Ala Glu Leu Ala Lys Ala Val
                355                 360                 365

Gly Gly His Lys Asn Val Gly Glu Val Arg Gly Asp Gly Met Leu Ala
                370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
                420                 425                 430

Pro Leu Cys Leu Thr Arg Glu Gln Ala Asp Ile Val Val Ser Lys Thr
                435                 440                 445

Ala Asp Ala Val Lys Ser Val Phe Ala Asn Leu
450                 455

<210> SEQ ID NO 4
<211> LENGTH: 1401
<212> TYPE: DNA
<213> ORGANISM: Artificial Sequence
<220> FEATURE:
<223> OTHER INFORMATION: Transaminase plus tag

<400> SEQUENCE: 4
atgctgaacc aatcgaacga actgaacgcc tgggatcgcg accactttt ccacccgtca    60 acgcacatgg gcacgcacgc acgcggcgaa agtccgaccc gtatcatggc cggcggtgaa    120
ggcgttacgg tctgggataa caatggtcgc aaatccattg acgcgtttgc cggcctgtat    180

```
tgcgtgaacg ttggctacgg tcgccagaaa attgcagatg ctatcgcgac ccaagctaaa    240
aatctggcgt attaccatgc ctatgtgggc cacggtaccg aagcgagcat acgctggcc     300 aaaatgatta tcgatcgtgc gccgaaaggc atgtctcgcg tttacttcgg cctgagcggt    360
tctgatgcca acgaaaccaa catcaaactg atctggtact acaacaacgt cctgggccgt    420
ccggagaaaa agaaaattat ctcccgttgg cgcggttatc atggcagcgg tgttatgacc    480
ggctctctga cgggtctgga cctgtttcat aacgcattcg acctgccgcg tgctccggtg    540
ctgcacaccg aagccccgta ttactttcgt cgcacggatc gcagtatgtc cgaagaacag    600
ttcagccaac actgtgcaga caaactggaa gaaatgattc tggctgaagg cccggaaacc    660
attgcggcct ttatcggcga accgattctg ggtacgggcg tatcgttcc gccgccggcg     720 ggttattggg aaaaaattca ggccgtcctg aaaaaatacg atgtgctgct ggttgcggac    780
gaagtggtta ccggctttgg tcgcctgggc acgatgttcg gttcagatca ttatggcatc    840
aaaccggacc tgattaccat cgcaaaaggc ctgacgagtg cctacgcacc gctgtccggt    900
gtcattgtgg cggatcgtgt gtggcaggtt ctggtccaag gctcagacaa actgggttcg    960
ctgggccatg gttggaccta ttcggcacac ccgatctgcg tggcagctgg tgttgccaac   1020
ctggaactga ttgatgaaat ggacctggtg accaatgcgg gcgaaacggg tgcatatttt   1080
cgtgctgaac tggctaaagc ggttggcggt cacaaaaatg tcggcgaagt gcgcggcgat   1140
ggtatgctgg cggccgttga attcgtcgca gataaagatg accgtgtgtt tttcgacgct   1200
tcacagaaaa tcggtccgca agtcgcaacc gcactggcag cttcgggtgt gatcggtcgt   1260
gcaatgccgc agggcgatat tctgggtttt gccccgccgc tgtgtctgac ccgtgaacag   1320
gcagatattg tcgtgagcaa aacggccgac gctgtcaaat cagtcttcgc aaacctgtca   1380
caccaccatc accaccacta a                                             1401
```

<210> SEQ ID NO 5
<211> LENGTH: 456
<212> TYPE: PRT
<213> ORGANISM: Oceanicola granulosus

<400> SEQUENCE: 5

```
Met Leu Lys Asn Asp Pro Leu Glu Gln Trp Asp Arg Asp His Phe Leu
1               5                   10                  15

His Pro Ser Thr His Leu Ala Glu Phe Ala Arg Gly Asn Val Ala His
                20                  25                  30

Arg Ile Val Ser Gly Gly Glu Gly Ser His Ile Val Asp Arg Asn Gly
            35                  40                  45

Thr Arg Leu Leu Asp Gly Phe Ala Gly Leu Tyr Cys Val Asn Val Gly
        50                  55                  60

Tyr Gly Arg Arg Glu Ile Ala Asp Ala Ile Ala Lys Gln Ala Arg Glu
65                  70                  75                  80

Leu Ser Tyr Tyr His Ser Tyr Val Gly His Gly Thr Glu Ala Ser Val
                85                  90                  95

Thr Leu Ala His Met Ile Leu Glu Arg Ala Pro Ala Asn Met Ser Lys
            100                 105                 110

Val Phe Phe Gly Leu Gly Gly Ser Asp Ala Asn Glu Thr Asn Ile Lys
        115                 120                 125

Leu Ile Trp Tyr Met Asn Asn Ile Leu Gly Arg Pro Gly Lys Lys Lys
    130                 135                 140

Ile Ile Ser Arg Trp Arg Gly Tyr His Gly Ser Gly Leu Met Ser Gly
```

```
                145                 150                 155                 160
        Ser Leu Thr Gly Leu Pro Leu Phe His Lys Ala Phe Asp Leu Pro Leu
                        165                 170                 175

Ala Pro Ile Leu His Thr Glu Ala Pro Tyr Tyr Arg Arg Pro Asn
                180                 185                 190

Ala Asp Met Ser Glu Glu Ala Phe Ser Ala Trp Cys Ala Ser Glu Leu
                        195                 200                 205

Glu Ala Met Ile Gln Arg Glu Gly Pro Asp Thr Ile Ala Ala Phe Trp
                        210                 215                 220

Ala Glu Pro Val Leu Gly Thr Gly Ile Val Pro Pro Glu Gly
        225                 230                 235                 240

Tyr Trp Ala Ala Ile Gln Glu Val Leu Asp Arg His Asp Ile Leu Leu
                                245                 250                 255

Val Ala Asp Glu Val Ile Thr Gly Phe Gly Arg Leu Gly Thr Met Phe
                        260                 265                 270

Gly Ser Asp His Tyr Gly Met Lys Pro Asp Val Ile Thr Ile Ala Lys
                        275                 280                 285

Gly Leu Thr Ser Ala Tyr Ala Pro Leu Ser Gly Ser Val Leu Ser Glu
                        290                 295                 300

Lys Val Trp Lys Val Leu Glu Gln Gly Thr Asp Glu Met Gly Ala Ile
        305                 310                 315                 320

Gly His Gly Trp Thr Tyr Ser Ala His Pro Ile Gly Ala Ala Ala Gly
                                325                 330                 335

Val Ala Asn Leu Lys Leu Ile Asp Glu Leu Gly Leu Ile Asp Asn Ala
                        340                 345                 350

Ala Glu Val Gly Ala His Leu Arg Ala Gly Met Arg Asp Ala Leu Gly
                        355                 360                 365

Glu His Pro Asn Val Gly Asp Ile Arg Gly Glu Gly Met Leu Cys Ala
                        370                 375                 380

Val Glu Leu Val Ser Asp Arg Glu Ser Lys Glu Gly Phe Asp Pro Ser
        385                 390                 395                 400

Arg Lys Val Thr Val Asn Ala Val Ala His Leu Met Glu Asn Gly Val
                                405                 410                 415

Ile Gly Arg Ala Met Pro His Ser Glu Thr Ile Gly Phe Ala Pro Pro
                        420                 425                 430

Phe Cys Leu Thr Arg Asp Glu Ala Asp Glu Ile Val Ala Lys Thr Ala
                        435                 440                 445

Ala Ala Val Lys Ala Val Leu Gly
            450                 455

<210> SEQ ID NO 6
<211> LENGTH: 460
<212> TYPE: PRT
<213> ORGANISM: Jannaschia Sp CCS1

<400> SEQUENCE: 6

Met Leu Thr Asn Asp Gln Leu Ser Gln Trp Asp Gln Asp His Phe Phe
1               5                   10                  15

His Pro Ser Thr Ala Leu Gly Ala His Ala Arg Gly Glu Ala Pro Gly
                20                  25                  30

Met Val Val Gln Thr Ala Glu Gly Cys His Ile Thr Asp Arg Asn Gly
                35                  40                  45

Asn Arg Met Leu Asp Ala Phe Ala Gly Leu Tyr Cys Val Asn Ile Gly
        50                  55                  60
```

Tyr Gly Arg Gln Glu Val Ala Glu Ala Ile Ala Ala Gln Ala Arg Glu
 65                  70                  75                  80

Leu Ala Tyr Tyr His Ser Tyr Met Gly Asn Gly Thr Glu Ala Ser Ile
                 85                  90                  95

Thr Leu Ala Lys Met Val Thr Glu Arg Ala Pro Glu Gly Met Asn Arg
            100                 105                 110

Val Tyr Phe Gly Gln Gly Gly Ser Asp Ala Asn Glu Thr Asn Ile Lys
        115                 120                 125

Leu Val Trp Tyr Tyr Asn Asn Ile Leu Gly Arg Pro Glu Lys Lys Lys
    130                 135                 140

Ile Val Ser Arg Trp Arg Gly Tyr His Gly Ser Gly Leu Met Ser Gly
145                 150                 155                 160

Ser Leu Thr Gly Leu Ser Leu Phe His Arg Lys Phe Asp Leu Pro Leu
                165                 170                 175

Asp Lys Val Leu His Thr Thr Ala Pro Tyr Tyr Phe Gln Arg Glu Asn
            180                 185                 190

Val Ala Gln Ser Glu Gln Glu Phe Thr Ala Gln Cys Val Ala Asp Leu
        195                 200                 205

Glu Glu Leu Ile Ala Arg Glu Gly Ala Asp Thr Ile Ala Ala Phe Ile
    210                 215                 220

Ala Glu Pro Val Ile Gly Thr Gly Gly Ile Val Pro Pro Glu Gly
225                 230                 235                 240

Tyr Trp Asn Ala Ile Gln Pro Val Leu Lys Arg His Asp Ile Leu Leu
                245                 250                 255

Ile Ala Asp Glu Val Ile Thr Gly Phe Gly Arg Leu Gly Ala Met Phe
            260                 265                 270

Gly Ser Pro Leu Tyr Gly Ile Glu Pro Asp Ile Met Thr Ile Ala Lys
        275                 280                 285

Gly Leu Thr Ser Ala Tyr Ala Pro Leu Ser Gly Ser Ile Val His Asp
    290                 295                 300

Arg Val Trp Asp Val Leu Ala Arg Gly Thr Asp Glu Asn Gly Pro Leu
305                 310                 315                 320

Gly His Gly Trp Thr Tyr Ser Ala His Pro Ile Gly Ala Ala Ala Gly
                325                 330                 335

Val Ala Asn Leu Thr Leu Leu Asp Thr Leu Gly Leu Val Asp Asn Ala
            340                 345                 350

Ala Asp Val Gly Pro Tyr Leu Thr Ala Gln Met Arg Ala Ala Met Gln
        355                 360                 365

Asp His Ala His Val Gly Asp Ile Arg Gly Val Gly Met Leu Thr Ala
    370                 375                 380

Val Glu Leu Val Ala Asp Arg Asp Lys Gly Ser Gly Val Gly Ala Gly
385                 390                 395                 400

Phe Asp Pro Ala Ala Lys Ile Val Pro Gln Ile Ser Ala Ala Met Ala
                405                 410                 415

Lys Arg Gly Val Ile Ala Arg Ala Met Pro Gln Ala Asp Ile Val Gly
            420                 425                 430

Phe Ser Pro Pro Leu Cys Leu Thr Arg Ala Glu Ala Asp Thr Ile Val
        435                 440                 445

Ser Val Thr Ala Glu Ala Val Ala Glu Val Leu Gly
    450                 455                 460

<210> SEQ ID NO 7
<211> LENGTH: 464
<212> TYPE: PRT

<213> ORGANISM: Xanthobacteraceae

<400> SEQUENCE: 7

```
Met Leu Asp His Pro Ala Pro Ala Ser Asn Ala Phe Asp Ser Trp Asp
 1               5                  10                  15
Arg Asp His Phe Phe His Pro Ser Thr His Met Gly Gln His Ala Arg
            20                  25                  30
Gly Glu Thr Pro Asn Arg Ile Ile Thr Gly Ala Glu Gly Val Tyr Ile
        35                  40                  45
Val Asp Arg Glu Gly Arg Ser Leu Asp Ala Phe Gly Gly Leu Tyr
    50                  55                  60
Cys Val Asn Val Gly Tyr Gly Arg Ser Lys Ile Thr Asp Ala Ile Ala
 65                  70                  75                  80
Glu Gln Ala Ser Lys Leu Ala Tyr Tyr His Ala Tyr Ala Gly His Gly
                85                  90                  95
Ser Glu Pro Ser Ile Arg Leu Ala Arg Met Val Ile Glu Arg Ala Pro
            100                 105                 110
Ala Gly Met Ser Arg Val Phe Phe Gly Leu Ser Gly Ser Asp Ala Asn
        115                 120                 125
Glu Thr Asn Ile Lys Leu Val Trp Tyr Ile Asn Asn Val Leu Gly Arg
    130                 135                 140
Pro Gln Lys Lys Lys Ile Ile Ser Arg Trp Arg Gly Tyr His Gly Ser
145                 150                 155                 160
Gly Val Met Thr Gly Ser Leu Thr Gly Leu Ala Gly Phe His Lys Leu
                165                 170                 175
Phe Asp Leu Pro Arg Ala Pro Ile Leu His Thr Glu Ala Pro Tyr Tyr
            180                 185                 190
Phe Arg Arg Glu Asp Arg Ser Met Ser Glu Glu Gln Phe Ser Gln His
        195                 200                 205
Cys Ala Asp Arg Leu Glu Glu Met Ile Leu Thr Glu Gly Ala Asp Thr
    210                 215                 220
Ile Ala Ala Phe Ile Gly Glu Pro Val Leu Gly Thr Gly Gly Ile Val
225                 230                 235                 240
Pro Pro Pro Ala Gly Tyr Trp Pro Lys Ile Gln Ala Val Leu Lys Lys
                245                 250                 255
Tyr Asp Ile Met Leu Ile Ala Asp Glu Val Val Thr Gly Phe Gly Arg
            260                 265                 270
Leu Gly Ser Met Phe Gly Ser Asp His Tyr Gly Ile Glu Pro Asp Leu
        275                 280                 285
Ile Thr Ile Ala Lys Gly Leu Thr Ser Ala Tyr Ala Pro Leu Ser Gly
    290                 295                 300
Val Ile Val Ser Glu Lys Val Trp Arg Val Leu Glu Gln Gly Ser Asp
305                 310                 315                 320
Glu Phe Gly Pro Ile Gly His Gly Trp Thr Tyr Ser Ser His Pro Leu
                325                 330                 335
Cys Thr Ala Ala Gly Val Ala Asn Leu Glu Leu Val Asp Glu Leu Asp
            340                 345                 350
Leu Val Thr Asn Ala Arg Glu Thr Gly Ala Tyr Phe Asn Ala Ala Leu
        355                 360                 365
Lys Asp Ala Leu Ser Gly His Arg His Val Gly Glu Val Arg Gly Glu
    370                 375                 380
Gly Leu Leu Ala Ala Val Glu Leu Val Arg Asp Arg Asp Asp Arg Thr
385                 390                 395                 400
```

```
Phe Phe Glu Ala Ser Glu Lys Val Gly Pro Arg Val Ala Ala Met
                405                 410                 415

Leu Glu Arg Gly Val Ile Ala Arg Ala Met Pro Gln Gly Asp Ile Leu
            420                 425                 430

Gly Phe Ala Pro Pro Leu Cys Leu Thr Arg Glu Glu Ala Asp Ile Val
        435                 440                 445

Val Asp Ala Thr Arg Gly Ala Val Glu Ala Val Cys Ala Thr Leu Gly
    450                 455                 460

<210> SEQ ID NO 8
<211> LENGTH: 457
<212> TYPE: PRT
<213> ORGANISM: Rhodobacteraceae bacterium RB2150_13166

<400> SEQUENCE: 8

Met Leu Arg Asn Asp Gln Leu Ala Glu Trp Asp Arg Glu Asn Phe Phe
1               5                   10                  15

His Ala Ser Thr His Leu Ala Ala His Ala Arg Gly Asp Thr Pro Thr
            20                  25                  30

Arg Ile Ile Thr Gly Gly Glu Gly Val Tyr Ile Gln Asp Arg Asp Gly
        35                  40                  45

Ala Lys Ile Leu Asp Gly Phe Ala Gly Leu Tyr Cys Val Asn Val Gly
    50                  55                  60

Tyr Gly Arg Arg Glu Ile Thr Asp Ala Ile Ala Ala Gln Val Ser Glu
65                  70                  75                  80

Leu Ser Tyr Tyr His Ala Tyr Ala Gly His Gly Thr Glu Ala Ser Val
                85                  90                  95

Thr Leu Ala Lys Met Val Leu Asp Arg Ala Pro Asp Asn Met Ser Lys
            100                 105                 110

Val Tyr Phe Gly Leu Gly Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Met Thr Gly
145                 150                 155                 160

Ser Leu Thr Gly Leu Gly Leu Phe His Ala Lys Phe Asp Leu Pro Met
                165                 170                 175

Asp Gly Val Leu His Thr Glu Ala Pro His Tyr Leu His Arg Ala Asp
            180                 185                 190

Arg Asn Gln Thr Glu Glu Gln Phe Ser Ala Tyr Cys Ala Ala Lys Leu
        195                 200                 205

Glu Glu Met Ile Leu Ala Glu Gly Pro Asp Thr Ile Ala Ala Phe Ile
    210                 215                 220

Gly Glu Pro Ile Leu Gly Thr Gly Gly Ile Val Pro Pro Lys Gly
225                 230                 235                 240

Tyr Trp Ala Ala Ile Gln Ala Val Leu Arg Lys Tyr Asp Ile Leu Leu
                245                 250                 255

Val Val Asp Glu Val Val Thr Gly Phe Gly Arg Leu Gly Thr Met Phe
            260                 265                 270

Gly Ser Glu His Tyr Gly Leu Lys Ala Asp Leu Ile Thr Ile Ala Lys
        275                 280                 285

Gly Leu Thr Ser Ala Tyr Ala Pro Leu Ser Gly Ser Ile Val Ser Lys
    290                 295                 300

Lys Met Trp Ala Val Leu Glu Lys Gly Thr Asp Glu Asn Gly Ala Phe
305                 310                 315                 320
```

```
Gly His Gly Trp Thr Tyr Ser Ala His Pro Ile Gly Ala Ala Gly
            325                 330                 335

Val Ala Asn Leu Lys Leu Ile Asp Asp Leu Gly Leu Ile Ala Asn Ala
        340                 345                 350

Ser Glu Thr Gly Ala Tyr Leu Lys Ser Ala Leu Gln Ala Ala Leu Gly
        355                 360                 365

Asp His Pro Asn Val Ala Glu Ile Arg Gly Glu Gly Met Leu Ala Ala
        370                 375                 380

Val Glu Phe Cys Ala Asp Arg Asp Leu Lys Gln Phe Asp Thr Ser
385                 390                 395                 400

Ala Thr Ile Gly Pro Arg Leu Ala Ala Glu Leu Leu Thr Arg Gly Val
            405                 410                 415

Ile Gly Arg Ala Met Pro Gln Ser Asp Thr Ile Gly Phe Ala Pro Pro
            420                 425                 430

Leu Cys Ile Thr Arg Ala Glu Val Asp Gln Ile Val Ala Ala Met Lys
            435                 440                 445

Gly Ala Val Asp Ala Val Leu Pro Ala
        450                 455

<210> SEQ ID NO 9
<211> LENGTH: 456
<212> TYPE: PRT
<213> ORGANISM: Martelella mediterranea DSM 17316

<400> SEQUENCE: 9

Met Leu Thr Asn Asp Gln Leu Asp Arg Phe Asp Arg Glu Asn Phe Phe
1               5                   10                  15

His Pro Ser Thr His Leu Ala Gln His Ala Arg Gly Glu Ser Pro Ser
            20                  25                  30

Arg Ile Val Lys Thr Ala Lys Gly Val Phe Ile Glu Asp Arg Asp Gly
        35                  40                  45

Asn Lys Leu Leu Asp Gly Phe Gly Gly Leu Tyr Cys Val Asn Val Gly
    50                  55                  60

Tyr Gly Gln Glu Ser Ile Ile Glu Ala Ile Ala Glu Gln Ala Lys Glu
65                  70                  75                  80

Leu Ala Tyr Tyr His Ala Tyr Ala Gly His Gly Thr Glu Ala Ser Ile
                85                  90                  95

Asn Leu Ala Lys Met Val Ile Asp Arg Ala Pro Asp His Met Ser Lys
            100                 105                 110

Val Tyr Phe Gly Leu Ser Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Met Thr Gly
145                 150                 155                 160

Ser Leu Thr Gly Leu Ala Gly Phe Gln Arg Lys Phe Asp Leu Pro Leu
                165                 170                 175

Glu Arg Val Phe His Thr Thr Ala Pro Tyr Tyr Tyr Arg Arg Lys Asp
            180                 185                 190

Leu Ala Met Ser Glu Ala Asp Phe Val Ala His Cys Val Ala Glu Leu
        195                 200                 205

Glu Met Arg Ile Glu Arg Glu Gly Ala Asp Thr Ile Ala Ala Phe Ile
    210                 215                 220

Gly Glu Pro Val Leu Gly Thr Gly Gly Ile Val Pro Pro Pro Glu Gly
```

```
                225                 230                 235                 240
Tyr Trp Lys Ala Ile Ser Ala Val Leu Glu Lys His Asp Ile Leu Leu
                    245                 250                 255
Ile Ala Asp Glu Val Val Thr Gly Phe Gly Arg Leu Gly Ser Met Phe
                260                 265                 270
Gly Ser Asp His Tyr Gly Leu Lys Pro Asp Leu Ile Thr Ile Ala Lys
                275                 280                 285
Gly Leu Thr Ser Ala Tyr Ala Pro Leu Ser Gly Thr Ile Val Ser Asp
            290                 295                 300
Lys Val Trp Lys Val Leu Glu Gln Gly Thr Asp Glu Asn Gly Pro Ile
305                 310                 315                 320
Gly His Gly Trp Thr Tyr Ser Ala His Pro Ile Gly Ala Ala Ala Gly
                        325                 330                 335
Val Ala Asn Leu Lys Leu Ile Asp Glu Leu Gly Leu Val Lys Asn Ala
                340                 345                 350
Ala Glu Thr Gly Ala Tyr Leu Arg Ala Ala Met Lys Asp Ala Leu Ser
                355                 360                 365
Asp His Pro His Val Gly Asp Ile Arg Gly Glu Gly Met Leu Met Ala
        370                 375                 380
Val Glu Phe Val Lys Asp Arg Glu Ser Arg Thr Phe Tyr Asp Pro Ser
385                 390                 395                 400
Glu Lys Val Gly Pro Asn Leu Ala Ala Leu Ile Ser Glu Gly Val
                    405                 410                 415
Ile Ala Arg Ala Met Pro Glu Gly Asp Ile Leu Gly Tyr Ala Pro Pro
                420                 425                 430
Leu Cys Leu Thr Arg Glu Glu Ala Asp Gln Ile Val Ala Ala Thr Lys
            435                 440                 445
Lys Ala Val Ile Ala Val Leu Gly
        450                 455

<210> SEQ ID NO 10
<211> LENGTH: 457
<212> TYPE: PRT
<213> ORGANISM: Rugeria pomeroyi DSS-3

<400> SEQUENCE: 10

Met Leu Lys Asn Asp Gln Leu Asp Gln Trp Asp Arg Glu Asn Phe Phe
1               5                   10                  15
His Pro Ser Thr His Leu Ala Gln His Ala Arg Gly Asp Ser Ala Asn
                20                  25                  30
Arg Val Ile Lys Thr Ala Ser Gly Val Phe Ile Glu Asp Arg Asp Gly
            35                  40                  45
Asn Lys Leu Leu Asp Ala Phe Ala Gly Leu Tyr Cys Val Asn Val Gly
        50                  55                  60
Tyr Gly Arg Gln Glu Ile Ala Asp Ala Ile Ala Asp Gln Ala Arg Glu
65                  70                  75                  80
Leu Ala Tyr Tyr His Ser Tyr Val Gly His Gly Thr Glu Ala Ser Ile
                85                  90                  95
Thr Leu Ala Lys Met Ile Leu Asp Arg Ala Pro Ala Asn Met Ser Lys
                100                 105                 110
Val Tyr Phe Gly Leu Gly Gly Ser Asp Ala Asn Glu Thr Asn Val Lys
            115                 120                 125
Leu Ile Trp Tyr Tyr Asn Asn Ile Leu Gly Arg Pro Glu Lys Lys Lys
        130                 135                 140
```

-continued

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
            165                 170                 175

Asn Gln Val Ile His Thr Glu Ala Pro Tyr Tyr Phe Arg Arg Ala Asp
        180                 185                 190

Pro Asp Gln Ser Glu Ala Gln Phe Val Ala His Cys Ala Ala Glu Leu
    195                 200                 205

Glu Ala Leu Ile Glu Arg Glu Gly Ala Asp Thr Ile Ala Ala Phe Ile
210                 215                 220

Gly Glu Pro Val Leu Gly Thr Gly Ile Val Pro Pro Ala Gly
225                 230                 235                 240

Tyr Trp Glu Ala Ile Gln Ala Val Leu Arg Lys His Asp Ile Leu Leu
                245                 250                 255

Ile Ala Asp Glu Val Val Thr Gly Phe Gly Arg Leu Gly Thr Met Phe
            260                 265                 270

Gly Ser Asp His Tyr Gly Ile Glu Ala Asp Ile Ile Thr Ile Ala Lys
        275                 280                 285

Gly Leu Thr Ser Ala Tyr Ala Pro Leu Ser Gly Ser Ile Ile Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Arg Leu Asn Leu Val Gln Asn Ala
            340                 345                 350

Gly Glu Thr Gly Ala Tyr Leu Asn Ala Thr Met Thr Glu Ala Leu Ala
        355                 360                 365

Gly His Pro Asn Val Gly Glu Val Arg Gly Ala Gly Met Leu Cys Ala
    370                 375                 380

Val Glu Phe Val Lys Asp Lys Asp Ser Arg Leu Phe Asp Ala Ala
385                 390                 395                 400

Asp Lys Ile Gly Pro Gln Ile Ser Ala Lys Leu Leu Glu Gln Asp Lys
                405                 410                 415

Val Ile Ala Arg Ala Met Pro Gln Gly Asp Ile Leu Gly Phe Ala Pro
            420                 425                 430

Pro Phe Cys Leu Ser Arg Ala Glu Ala Asp Gln Val Val Asp Ala Thr
        435                 440                 445

Leu Arg Ala Val Arg Thr Val Leu Gly
    450                 455

<210> SEQ ID NO 11
<211> LENGTH: 456
<212> TYPE: PRT
<213> ORGANISM: Sagittula stellata E-37

<400> SEQUENCE: 11

Met Leu Thr Asn Asp Gln Leu Ser Gln Trp Asp Arg Glu Asn Phe Phe
1               5                   10                  15

His Pro Ser Thr His Leu Ala Gln His Ala Arg Gly Glu Thr Ala Thr
            20                  25                  30

Arg Val Ile Thr Thr Gly Gln Gly Cys His Ile Glu Asp Arg Asp Gly
        35                  40                  45

Thr Lys Leu Leu Asp Ala Phe Ala Gly Leu Tyr Cys Val Asn Val Gly
    50                  55                  60

Tyr Gly Arg Thr Glu Ile Ala Asp Ala Ile Ala Gln Ala Lys Glu
 65                  70                  75                  80

Leu Ala Tyr Tyr His Ala Tyr Val Gly His Gly Thr Glu Ala Ser Ile
                 85                  90                  95

Thr Leu Ser Lys Met Ile Leu Asp Arg Ala Pro Ala His Met Ser Lys
            100                 105                 110

Val Tyr Phe Gly Leu Ser Gly Ser Asp Ala Asn Glu Thr Asn Ile Lys
            115                 120                 125

Leu Ile Trp Tyr Tyr Asn Asn Ile Leu Gly Arg Pro Glu Lys Lys Lys
            130                 135                 140

Ile Ile Ser Arg Trp Arg Gly Tyr His Gly Ser Gly Leu Met Thr Gly
145                 150                 155                 160

Ser Leu Thr Gly Leu Glu Leu Phe His Lys Lys Phe Asp Leu Pro Leu
                165                 170                 175

Ala Gln Val Ile His Thr Glu Ala Pro Tyr Tyr Phe Arg Arg Pro Asp
            180                 185                 190

Leu Ala Met Ser Glu Glu Ala Phe Ser Ala Tyr Cys Ala Ala Glu Leu
            195                 200                 205

Glu Gln Leu Ile Glu Arg Glu Gly Ala Asp Thr Ile Ala Ala Phe Ile
210                 215                 220

Gly Glu Pro Val Leu Gly Thr Gly Gly Ile Val Pro Pro Lys Gly
225                 230                 235                 240

Tyr Trp Glu Ala Ile Gln Pro Ile Leu Glu Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Lys Pro Asp Leu Ile Thr Ile Ala Lys
            275                 280                 285

Gly Leu Thr Ser Ala Tyr Ala Pro Leu Ser Gly Ser Ile Val Gly Asp
            290                 295                 300

Lys Met Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Asp Met Asn Leu Val Ala Asn Ala
            340                 345                 350

Gly Glu Thr Gly Ala His Phe Arg Lys Ala Met Thr Asp Ala Leu Gly
            355                 360                 365

Asp His Ala Lys Val Gly Asp Ile Arg Gly Glu Gly Met Leu Cys Ala
            370                 375                 380

Val Glu Leu Val Asp Asp Lys Asp Asn Arg Thr Phe Phe Asp Pro Ser
385                 390                 395                 400

Gln Lys Val Gly Ala Gln Ile Ala Ser Ala Leu Leu Ser Lys Gly Val
                405                 410                 415

Ile Ala Arg Ala Met Pro Gln Gly Asp Ile Leu Gly Phe Ala Pro Pro
            420                 425                 430

Leu Cys Leu Thr Pro Ala Glu Ala Glu Glu Val Ala Thr Lys Thr Gly
            435                 440                 445

Glu Ala Val Arg Asp Val Leu Gly
450                 455

<210> SEQ ID NO 12
<211> LENGTH: 457

<212> TYPE: PRT
<213> ORGANISM: Artificial Sequence
<220> FEATURE:
<223> OTHER INFORMATION: mutant transaminase

<400> SEQUENCE: 12

```
Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Tyr Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
    370                 375                 380
```

```
Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
            405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
    450                 455

<210> SEQ ID NO 13
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 13

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
50                  55                  60

Tyr Gly Arg Gln Glu Ile Ala Glu Ala Ile Asp Gln Ala Arg Glu
65                  70                  75                  80

Leu Ala Tyr Tyr His Ser Tyr Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285
```

```
Gly Leu Thr Ser Ala Tyr Ala Pro Leu Ser Gly Ser Ile Val Ser Asp
        290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
450                 455

<210> SEQ ID NO 14
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 14

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Phe Cys Val Asn Val Gly
50                  55                  60

Tyr Gly Arg Gln Glu Ile Ala Glu Ala Ile Ala Asp Gln Ala Arg Glu
65                  70                  75                  80

Leu Ala Tyr Tyr His Ser Tyr Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190
```

Leu Asn Gln Thr Glu Gln Phe Val Ala His Cys Val Ala Glu Leu
            195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Thr Ile Ala Lys
            275                 280                 285

Gly Leu Thr Ser Ala Tyr Ala Pro Leu Ser Gly Ser Ile Val Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
    355                 360                 365

Gln His Ala Asn Val Gly Asp Val Arg Gly Glu Gly Leu Leu Cys Ala
            370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
    435                 440                 445

Leu Arg Ala Val Lys Ala Val Leu Gly
    450                 455

<210> SEQ ID NO 15
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 15

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Trp Cys Val Asn Val
    50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Tyr Val Gly His Gly Thr Glu Ala Ser
                85                  90                  95

```
Ile Thr Leu Ala Lys Met Ile Ile Asp Arg Ala Pro Lys Gly Met Ser
                100                 105                 110

Arg Val Tyr Phe Gly Leu Ser Gly Ser Asp Ala Asn Glu Thr Asn Ile
            115                 120                 125

Lys Leu Ile Trp Tyr Asn Asn Val Leu Gly Arg Pro Glu Lys Lys
        130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
210                 215                 220

Ile Gly Glu Pro Ile Leu Gly Ala Gly Gly Ile Val Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
        355                 360                 365

Gly Gly His Lys Asn Val Gly Glu Val Arg Gly Asp Gly Met Leu Ala
370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
        435                 440                 445

Ala Asp Ala Val Lys Ser Val Phe Ala Asn Leu
        450                 455
```

<210> SEQ ID NO 16
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 16

```
Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
            35                  40                  45

Gly Arg Lys Ser Ile Asp Ala Phe Ala Gly Leu Trp Cys Val Asn Val
50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Tyr Val Gly His Gly Thr Glu Ala Ser
                85                  90                  95

Ile Thr Leu Ala Lys Met Ile Ile Asp Arg Ala Pro Lys Gly Met Ser
                100                 105                 110

Arg Val Tyr Phe Gly Leu Ser Gly Ser Asp Ala Asn Glu Thr Asn Ile
            115                 120                 125

Lys Leu Ile Trp Tyr Tyr Asn Asn Val Leu Gly Arg Pro Glu Lys Lys
            130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
            195                 200                 205

Leu Glu Glu Met Ile Leu Ala Glu Gly Pro Glu Thr Ile Ala Ala Phe
210                 215                 220

Ile Gly Glu Pro Ile Leu Gly Gly Gly Ile Val Pro Pro Ala
225                 230                 235                 240

Gly Tyr Trp Glu Lys Ile Gln Ala Val Leu Lys Lys Tyr Asp Val Leu
            245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
            275                 280                 285

Lys Gly Leu Thr Ser Ala Tyr Ala Pro Leu Ser Gly Val Ile Val Ala
            290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
            355                 360                 365

Gly Gly His Lys Asn Val Gly Glu Val Arg Gly Asp Gly Met Leu Ala
            370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
            405                 410                 415

Val Ile Gly Arg Ala Met Pro Gln Gly Asp Ile Leu Gly Phe Ala Pro
```

```
                420                 425                 430
Pro Leu Cys Leu Thr Arg Glu Gln Ala Asp Ile Val Val Ser Lys Thr
            435                 440                 445
Ala Asp Ala Val Lys Ser Val Phe Ala Asn Leu
        450                 455

<210> SEQ ID NO 17
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 17

Met Leu Asn Gln Ser Asn Glu Leu Asn Ala Trp Asp Arg Asp His Phe
1               5                   10                  15
Phe His Pro Ser Thr His Met Gly Thr His Ala Arg Gly Glu Ser Pro
            20                  25                  30
Thr Arg Ile Met Ala Gly Gly Glu Gly Val Thr Val Trp Asp Asn Asn
        35                  40                  45
Gly Arg Lys Ser Ile Asp Ala Phe Ala Gly Leu Phe Cys Val Asn Val
    50                  55                  60
Gly Tyr Gly Arg Gln Lys Ile Ala Asp Ala Ile Ala Thr Gln Ala Lys
65                  70                  75                  80
Asn Leu Ala Tyr Tyr His Ala Tyr Val Gly His Gly Thr Glu Ala Ser
                85                  90                  95
Ile Thr Leu Ala Lys Met Ile Ile Asp Arg Ala Pro Lys Gly Met Ser
            100                 105                 110
Arg Val Tyr Phe Gly Leu Ser Gly Ser Asp Ala Asn Glu Thr Asn Ile
        115                 120                 125
Lys Leu Ile Trp Tyr Tyr Asn Asn Val Leu Gly Arg Pro Glu Lys Lys
    130                 135                 140
Lys Ile Ile Ser Arg Trp Arg Gly Tyr His Gly Ser Gly Val Met Thr
145                 150                 155                 160
Gly Ser Leu Thr Gly Leu Asp Leu Phe His Asn Ala Phe Asp Leu Pro
                165                 170                 175
Arg Ala Pro Val Leu His Thr Glu Ala Pro Tyr Tyr Phe Arg Arg Thr
            180                 185                 190
Asp Arg Ser Met Ser Glu Glu Gln Phe Ser Gln His Cys Ala Asp Lys
        195                 200                 205
Leu Glu Glu Met Ile Leu Ala Glu Gly Pro Glu Thr Ile Ala Ala Phe
    210                 215                 220
Ile Gly Glu Pro Ile Leu Gly Ala Gly Gly Ile Val Pro Pro Ala
225                 230                 235                 240
Gly Tyr Trp Glu Lys Ile Gln Ala Val Leu Lys Lys Tyr Asp Val Leu
                245                 250                 255
Leu Val Ala Asp Glu Val Val Thr Gly Phe Gly Arg Leu Gly Thr Met
            260                 265                 270
Phe Gly Ser Asp His Tyr Gly Ile Lys Pro Asp Leu Ile Thr Ile Ala
        275                 280                 285
Lys Gly Leu Thr Ser Ala Tyr Ala Pro Leu Ser Gly Val Ile Val Ala
    290                 295                 300
Asp Arg Val Trp Gln Val Leu Val Gln Gly Ser Asp Lys Leu Gly Ser
305                 310                 315                 320
Leu Gly His Gly Trp Thr Tyr Ser Ala His Pro Ile Cys Val Ala Ala
```

```
                    325                 330                 335
Gly Val Ala Asn Leu Glu Leu Ile Asp Glu Met Asp Leu Val Thr Asn
                340                 345                 350

Ala Gly Glu Thr Gly Ala Tyr Phe Arg Ala Glu Leu Ala Lys Ala Val
            355                 360                 365

Gly Gly His Lys Asn Val Gly Glu Val Arg Gly Asp Gly Met Leu Ala
        370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
        435                 440                 445

Ala Asp Ala Val Lys Ser Val Phe Ala Asn Leu
    450                 455
```

<210> SEQ ID NO 18
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 18

```
Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
                20                  25                  30

Arg Val Ile Lys Thr Ala Ser Gly Val Phe Ile Glu Asp Arg Asp Gly
            35                  40                  45

Thr Lys Leu Leu Asp Ala Phe Ala Gly Leu Trp Cys Val Asn Val Gly
        50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Gly Ile Val Pro Pro Pro Ala Gly
```

```
                225                 230                 235                 240
Tyr Trp Glu Ala Ile Gln Thr Val Leu Asn Lys His Asp Ile Leu Leu
                    245                 250                 255

Val Ala Asp Glu Val Val Thr Gly Phe Gly Arg Leu Gly Thr Met Phe
                260                 265                 270

Gly Ser Asp His Tyr Gly Leu Glu Pro Asp Ile Ile Thr Ile Ala Lys
                275                 280                 285

Gly Leu Thr Ser Ala Tyr Ala Pro Leu Ser Gly Ser Ile Val Ser Asp
            290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
                340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Glu Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
                420                 425                 430

Pro Phe Cys Leu Thr Arg Ala Glu Ala Asp Gln Val Val Glu Gly Thr
                435                 440                 445

Leu Arg Ala Val Lys Ala Val Leu Gly
            450                 455

<210> SEQ ID NO 19
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 19

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
                20                  25                  30

Arg Val Ile Lys Thr Ala Ser Gly Val Phe Ile Glu Asp Arg Asp Gly
            35                  40                  45

Thr Lys Leu Leu Asp Ala Phe Ala Gly Leu Trp Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Leu Val Gly His Gly Thr Glu Ala Ser Ile
                85                  90                  95

Thr Leu Ala Lys Met Ile Leu Asp Arg Ala Pro Lys Asn Met Ser Lys
                100                 105                 110

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
```

```
                130             135             140
Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
210                 215                 220

Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
        290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
450                 455

<210> SEQ ID NO 20
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 20

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
```

```
            35                  40                  45
Thr Lys Leu Leu Asp Ala Phe Ala Gly Leu Trp Cys Val Asn Val Gly
 50                  55                  60

Tyr Gly Arg Gln Glu Ile Ala Glu Ala Ile Ala Asp Gln Ala Arg Glu
 65                  70                  75                  80

Leu Ala Tyr Tyr His Ser Val Val Gly His Gly Thr Glu Ala Ser Ile
                 85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
            130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
                180                 185                 190

Leu Asn Gln Thr Glu Glu Gln Phe Val Ala His Cys Val Ala Glu Leu
            195                 200                 205

Glu Ala Leu Ile Glu Arg Glu Gly Ala Asp Thr Ile Ala Ala Phe Ile
210                 215                 220

Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
            275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Glu Gly Leu Leu Cys Ala
            370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
450                 455
```

<210> SEQ ID NO 21
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 21

```
Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Phe Cys Val Asn Val Gly
50                  55                  60

Tyr Gly Arg Gln Glu Ile Ala Glu Ala Ile Ala Asp Gln Ala Arg Glu
65                  70                  75                  80

Leu Ala Tyr Tyr His Ser Tyr Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
210                 215                 220

Gly Glu Pro Ile Leu Gly Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365
```

```
Gln His Ala Asn Val Gly Asp Val Arg Gly Glu Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
            405                 410                 415

Ile Ile Ala Arg Ala Met Pro Gln Gly Asp Ile Leu Gly Phe Ala Pro
                420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
    450                 455

<210> SEQ ID NO 22
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 22

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
50                  55                  60

Tyr Gly Arg Gln Glu Ile Ala Glu Ala Ile Ala Asp Gln Ala Arg Glu
65                  70                  75                  80

Leu Ala Tyr Tyr His Ser Tyr Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
210                 215                 220

Gly Glu Pro Ile Leu Gly Ala Gly Gly Phe Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270
```

```
Gly Ser Asp His Tyr Gly Leu Glu Pro Asp Ile Ile Thr Ile Ala Lys
            275                 280                 285

Gly Leu Thr Ser Ala Tyr Ala Pro Leu Ser Gly Ser Ile Val Ser Asp
        290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
    370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
    450                 455

<210> SEQ ID NO 23
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 23

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
                20                  25                  30

Arg Val Ile Lys Thr Ala Ser Gly Val Phe Ile Glu Asp Arg Asp Gly
            35                  40                  45

Thr Lys Leu Leu Asp Ala Phe Ala Gly Leu Trp Cys Val Asn Val Gly
        50                  55                  60

Tyr Gly Arg Gln Glu Ile Ala Glu Ala Ile Ala Asp Gln Ala Arg Glu
65                  70                  75                  80

Leu Ala Tyr Tyr His Ser Tyr Val Gly His Gly Thr Glu Ala Ser Ile
                85                  90                  95

Thr Leu Ala Lys Met Ile Leu Asp Arg Ala Pro Lys Asn Met Ser Lys
                100                 105                 110

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
        130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175
```

```
Glu Gln Val Ile His Thr Glu Ala Pro Tyr Tyr Phe Arg Arg Glu Asp
                180                 185                 190

Leu Asn Gln Thr Glu Glu Gln Phe Val Ala His Cys Val Ala Glu Leu
            195                 200                 205

Glu Ala Leu Ile Glu Arg Glu Gly Ala Asp Thr Ile Ala Ala Phe Ile
210                 215                 220

Gly Glu Pro Ile Leu Gly Ala Gly Met Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
    450                 455

<210> SEQ ID NO 24
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 24

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
                20                  25                  30

Thr Arg Ile Met Ala Gly Gly Glu Gly Val Thr Val Trp Asp Asn Asn
            35                  40                  45

Gly Arg Lys Ser Ile Asp Ala Phe Ala Gly Leu Trp Cys Val Asn Val
        50                  55                  60

Gly Tyr Gly Arg Gln Lys Ile Ala Asp Ala Ile Ala Thr Gln Ala Lys
65                  70                  75                  80
```

Asn Leu Ala Tyr Tyr His Ala Phe Val Gly His Gly Thr Glu Ala Ser
                85                  90                  95

Ile Thr Leu Ala Lys Met Ile Ile Asp Arg Ala Pro Lys Gly Met Ser
               100                 105                 110

Arg Val Tyr Phe Gly Leu Ser Gly Ser Asp Ala Asn Glu Thr Asn Ile
               115                 120                 125

Lys Leu Ile Trp Tyr Tyr Asn Asn Val Leu Gly Arg Pro Glu Lys Lys
    130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
               165                 170                 175

Arg Ala Pro Val Leu His Thr Glu Ala Pro Tyr Tyr Phe Arg Arg Thr
               180                 185                 190

Asp Arg Ser Met Ser Glu Glu Gln Phe Ser Gln His Cys Ala Asp Lys
               195                 200                 205

Leu Glu Glu Met Ile Leu Ala Glu Gly Pro Glu Thr Ile Ala Ala Phe
    210                 215                 220

Ile Gly Glu Pro Ile Leu Gly Ala Gly Gly Ile Val Pro Pro Pro Ala
225                 230                 235                 240

Gly Tyr Trp Glu Lys Ile Gln Ala Val Leu Lys Lys Tyr Asp Val Leu
               245                 250                 255

Leu Val Ala Asp Glu Val Val Thr Gly Phe Gly Arg Leu Gly Thr Met
               260                 265                 270

Phe Gly Ser Asp His Tyr Gly Ile Lys Pro Asp Leu Ile Thr Ile Ala
               275                 280                 285

Lys Gly Leu Thr Ser Ala Tyr Ala Pro Leu Ser Gly Val Ile Val Ala
    290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
               325                 330                 335

Gly Val Ala Asn Leu Glu Leu Ile Asp Glu Met Asp Leu Val Thr Asn
               340                 345                 350

Ala Gly Glu Thr Gly Ala Tyr Phe Arg Ala Glu Leu Ala Lys Ala Val
               355                 360                 365

Gly Gly His Lys Asn Val Gly Glu Val Arg Gly Asp Gly Met Leu Ala
    370                 375                 380

Ala Val Glu Phe Val Ala Asp Lys Asp Asp Arg Val Phe Phe Asp Ala
385                 390                 395                 400

Ser Gln Lys Ile Gly Pro Gln Val Ala Thr Ala Leu Ala Ala Ser Gly
               405                 410                 415

Val Ile Gly Arg Ala Met Pro Gln Gly Asp Ile Leu Gly Phe Ala Pro
               420                 425                 430

Pro Leu Cys Leu Thr Arg Glu Gln Ala Asp Ile Val Val Ser Lys Thr
               435                 440                 445

Ala Asp Ala Val Lys Ser Val Phe Ala Asn Leu
    450                 455

<210> SEQ ID NO 25
<211> LENGTH: 459
<212> TYPE: PRT
<213> ORGANISM: Artificial Sequence
<220> FEATURE:

<223> OTHER INFORMATION: Mutant Transaminase

<400> SEQUENCE: 25

```
Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Trp Cys Val Asn Val
50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Leu Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
            115                 120                 125

Lys Leu Ile Trp Tyr Tyr Asn Asn Val Leu Gly Arg Pro Glu Lys Lys
        130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
210                 215                 220

Ile Gly Glu Pro Ile Leu Gly Ala Gly Gly Ile Val Pro Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
        290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Glu Met Asp Leu Val Thr Asn
            340                 345                 350

Ala Gly Glu Thr Gly Ala Tyr Phe Arg Ala Glu Leu Ala Lys Ala Val
        355                 360                 365

Gly Gly His Lys Asn Val Gly Glu Val Arg Gly Asp Gly Met Leu Ala
        370                 375                 380

Ala Val Glu Phe Val Ala Asp Lys Asp Arg Val Phe Phe Asp Ala
385                 390                 395                 400
```

Ser Gln Lys Ile Gly Pro Gln Val Ala Thr Ala Leu Ala Ala Ser Gly
            405                 410                 415

Val Ile Gly Arg Ala Met Pro Gly Asp Ile Leu Gly Phe Ala Pro
        420                 425                 430

Pro Leu Cys Leu Thr Arg Glu Gln Ala Asp Ile Val Val Ser Lys Thr
            435                 440                 445

Ala Asp Ala Val Lys Ser Val Phe Ala Asn Leu
    450                 455

<210> SEQ ID NO 26
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 26

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Trp Cys Val Asn Val
50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Val Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Val Leu Gly Arg Pro Glu Lys Lys
130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
210                 215                 220

Ile Gly Glu Pro Ile Leu Gly Ala Gly Gly Ile Val Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
    290                 295                 300

```
Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
            325                 330                 335

Gly Val Ala Asn Leu Glu Leu Ile Asp Glu Met Asp Leu Val Thr Asn
        340                 345                 350

Ala Gly Glu Thr Gly Ala Tyr Phe Arg Ala Glu Leu Ala Lys Ala Val
            355                 360                 365

Gly Gly His Lys Asn Val Glu Val Arg Gly Asp Gly Met Leu Ala
        370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
            405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
            435                 440                 445

Ala Asp Ala Val Lys Ser Val Phe Ala Asn Leu
        450                 455
```

<210> SEQ ID NO 27
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 27

```
Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Phe Cys Val Asn Val
50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Tyr Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
            115                 120                 125

Lys Leu Ile Trp Tyr Tyr Asn Asn Val Leu Gly Arg Pro Glu Lys Lys
        130                 135                 140

Lys Ile Ile Ser Arg Trp Arg Gly Phe His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205
```

```
Leu Glu Glu Met Ile Leu Ala Glu Gly Pro Glu Thr Ile Ala Ala Phe
    210                 215                 220

Ile Gly Glu Pro Ile Leu Gly Gly Gly Ile Val Pro Pro Ala
225                 230                 235                 240

Gly Tyr Trp Glu Lys Ile Gln Ala Val Leu Lys Tyr Asp Val Leu
                245                 250                 255

Leu Val Ala Asp Glu Val Val Thr Gly Phe Gly Arg Leu Gly Thr Met
                260                 265                 270

Phe Gly Ser Asp His Tyr Gly Ile Lys Pro Asp Leu Ile Thr Ile Ala
            275                 280                 285

Lys Gly Leu Thr Ser Ala Tyr Ala Pro Leu Ser Gly Val Ile Val Ala
    290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
    355                 360                 365

Gly Gly His Lys Asn Val Gly Glu Val Arg Gly Asp Gly Met Leu Ala
370                 375                 380

Ala Val Glu Phe Val Ala Asp Lys Asp Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
                420                 425                 430

Pro Leu Cys Leu Thr Arg Glu Gln Ala Asp Ile Val Val Ser Lys Thr
            435                 440                 445

Ala Asp Ala Val Lys Ser Val Phe Ala Asn Leu
    450                 455
```

<210> SEQ ID NO 28
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 28

```
Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
                20                  25                  30

Thr Arg Ile Met Ala Gly Gly Glu Gly Val Thr Val Trp Asp Asn Asn
            35                  40                  45

Gly Arg Lys Ser Ile Asp Ala Phe Ala Gly Leu Trp Cys Val Asn Val
50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Tyr Val Gly His Gly Thr Glu Ala Ser
                85                  90                  95

Ile Thr Leu Ala Lys Met Ile Ile Asp Arg Ala Pro Lys Gly Met Ser
            100                 105                 110
```

Arg Val Tyr Phe Gly Leu Ser Gly Ser Asp Ala Asn Glu Thr Asn Ile
            115                 120                 125

Lys Leu Ile Trp Tyr Tyr Asn Asn Val Leu Gly Arg Pro Glu Lys Lys
    130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
    210                 215                 220

Ile Gly Glu Pro Ile Leu Gly Ala Gly Gly Phe Val Pro Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
    290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
        355                 360                 365

Gly Gly His Lys Asn Val Gly Glu Val Arg Gly Asp Gly Met Leu Ala
    370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
        435                 440                 445

Ala Asp Ala Val Lys Ser Val Phe Ala Asn Leu
    450                 455

<210> SEQ ID NO 29
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 29

Met Leu Asn Gln Ser Asn Glu Leu Asn Ala Trp Asp Arg Asp His Phe
1               5                   10                  15

-continued

```
Phe His Pro Ser Thr His Met Gly Thr His Ala Arg Gly Glu Ser Pro
             20                  25                  30

Thr Arg Ile Met Ala Gly Gly Glu Gly Val Thr Val Trp Asp Asn Asn
         35                  40                  45

Gly Arg Lys Ser Ile Asp Ala Phe Ala Gly Leu Trp Cys Val Asn Val
     50                  55                  60

Gly Tyr Gly Arg Gln Lys Ile Ala Asp Ala Ile Ala Thr Gln Ala Lys
 65                  70                  75                  80

Asn Leu Ala Tyr Tyr His Ala Tyr Val Gly His Gly Thr Glu Ala Ser
                 85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Val Leu Gly Arg Pro Glu Lys Lys
    130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Thr Ile Ala Ala Phe
    210                 215                 220

Ile Gly Glu Pro Ile Leu Gly Ala Gly Gly Met Val Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
    290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
        355                 360                 365

Gly Gly His Lys Asn Val Gly Val Arg Gly Asp Gly Met Leu Ala
    370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
```

```
                       435                 440                 445
Ala Asp Ala Val Lys Ser Val Phe Ala Asn Leu
    450                 455

<210> SEQ ID NO 30
<211> LENGTH: 457
<212> TYPE: PRT
<213> ORGANISM: Artificial Sequence
<220> FEATURE:
<223> OTHER INFORMATION: mutant transaminase

<400> SEQUENCE: 30

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Leu Asp Glu Leu Asn Leu Val Ser Asn Ala
```

```
                 340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Glu Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
    450                 455

<210> SEQ ID NO 31
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 31

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Trp Cys Val Asn Val
    50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Leu Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Val Leu Gly Arg Pro Glu Lys Lys
    130                 135                 140

Lys Ile Ile Ser Arg Trp Arg Gly Tyr His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
    210                 215                 220

Ile Gly Glu Pro Ile Leu Gly Ala Gly Gly Ile Val Pro Pro Ala
225                 230                 235                 240

Gly Tyr Trp Glu Lys Ile Gln Ala Val Leu Lys Lys Tyr Asp Val Leu
```

```
                   245                 250                 255
Leu Val Ala Asp Glu Val Val Thr Gly Phe Gly Arg Leu Gly Thr Met
            260                 265                 270
Phe Gly Ser Asp His Tyr Gly Ile Lys Pro Asp Leu Ile Thr Ile Ala
            275                 280                 285
Lys Gly Leu Thr Ser Ala Tyr Ala Pro Leu Ser Gly Val Ile Val Ala
            290                 295                 300
Asp Arg Val Trp Gln Val Leu Val Gln Gly Ser Asp Lys Leu Gly Ser
305                 310                 315                 320
Leu Gly His Gly Trp Thr Tyr Ser Ala His Pro Ile Cys Val Ala Ala
            325                 330                 335
Gly Val Ala Asn Leu Glu Leu Ile Asp Glu Met Asp Leu Val Thr Asn
            340                 345                 350
Ala Gly Glu Thr Gly Ala Tyr Phe Arg Ala Glu Leu Ala Lys Ala Val
            355                 360                 365
Gly Gly His Lys Asn Val Gly Glu Val Arg Gly Asp Gly Met Leu Ala
            370                 375                 380
Ala Val Glu Phe Val Ala Asp Lys Asp Asp Arg Val Phe Phe Asp Ala
385                 390                 395                 400
Ser Gln Lys Ile Gly Pro Gln Val Ala Thr Ala Leu Ala Ala Ser Gly
            405                 410                 415
Val Ile Gly Arg Ala Met Pro Gln Gly Asp Ile Leu Gly Phe Ala Pro
            420                 425                 430
Pro Leu Cys Leu Thr Arg Glu Gln Ala Asp Ile Val Val Ser Lys Thr
            435                 440                 445
Ala Asp Ala Val Lys Ser Val Phe Ala Asn Leu
450                 455

<210> SEQ ID NO 32
<211> LENGTH: 456
<212> TYPE: PRT
<213> ORGANISM: Artificial Sequence
<220> FEATURE:
<223> OTHER INFORMATION: mutant transaminase

<400> SEQUENCE: 32

Met Leu Lys Asn Asp Pro Leu Glu Gln Trp Asp Arg Asp His Phe Leu
1               5                   10                  15
His Pro Ser Thr His Leu Ala Glu Phe Ala Arg Gly Asn Val Ala His
            20                  25                  30
Arg Ile Val Ser Gly Gly Glu Gly Ser His Ile Val Asp Arg Asn Gly
            35                  40                  45
Thr Arg Leu Leu Asp Gly Phe Ala Gly Leu Trp Cys Val Asn Val Gly
            50                  55                  60
Tyr Gly Arg Arg Glu Ile Ala Asp Ala Ile Ala Lys Gln Ala Arg Glu
65                  70                  75                  80
Leu Ser Tyr Tyr His Ser Phe Val Gly His Gly Thr Glu Ala Ser Val
            85                  90                  95
Thr Leu Ala His Met Ile Leu Glu Arg Ala Pro Ala Asn Met Ser Lys
            100                 105                 110
Val Phe Phe Gly Leu Gly Gly Ser Asp Ala Asn Glu Thr Asn Ile Lys
            115                 120                 125
Leu Ile Trp Tyr Met Asn Asn Ile Leu Gly Arg Pro Gly Lys Lys Lys
            130                 135                 140
Ile Ile Ser Arg Trp Arg Gly Phe His Gly Ser Gly Leu Met Ser Gly
```

```
            145                 150                 155                 160
        Ser Leu Thr Gly Leu Pro Leu Phe His Lys Ala Phe Asp Leu Pro Leu
                        165                 170                 175

Ala Pro Ile Leu His Thr Glu Ala Pro Tyr Tyr Arg Arg Pro Asn
                    180                 185                 190

Ala Asp Met Ser Glu Glu Ala Phe Ser Ala Trp Cys Ala Ser Glu Leu
                        195                 200                 205

Glu Ala Met Ile Gln Arg Glu Gly Pro Asp Thr Ile Ala Ala Phe Trp
        210                 215                 220

Ala Glu Pro Val Leu Gly Ala Gly Ile Val Pro Pro Glu Gly
        225                 230                 235                 240

Tyr Trp Ala Ala Ile Gln Glu Val Leu Asp Arg His Asp Ile Leu Leu
                            245                 250                 255

Val Ala Asp Glu Val Ile Thr Gly Phe Gly Arg Leu Gly Thr Met Phe
                        260                 265                 270

Gly Ser Asp His Tyr Gly Met Lys Pro Asp Val Ile Thr Ile Ala Lys
                    275                 280                 285

Gly Leu Thr Ser Ala Tyr Ala Pro Leu Ser Gly Ser Val Leu Ser Glu
                290                 295                 300

Lys Val Trp Lys Val Leu Glu Gln Gly Thr Asp Glu Met Gly Ala Ile
        305                 310                 315                 320

Gly His Gly Trp Thr Tyr Ser Ala His Pro Ile Gly Ala Ala Ala Gly
                        325                 330                 335

Val Ala Asn Leu Lys Leu Ile Asp Glu Leu Gly Leu Ile Asp Asn Ala
                    340                 345                 350

Ala Glu Val Gly Ala His Leu Arg Ala Gly Met Arg Asp Ala Leu Gly
                355                 360                 365

Glu His Pro Asn Val Gly Asp Ile Arg Gly Glu Gly Met Leu Cys Ala
                370                 375                 380

Val Glu Leu Val Ser Asp Arg Glu Ser Lys Glu Gly Phe Asp Pro Ser
        385                 390                 395                 400

Arg Lys Val Thr Val Asn Ala Val Ala His Leu Met Glu Asn Gly Val
                        405                 410                 415

Ile Gly Arg Ala Met Pro His Ser Glu Thr Ile Gly Phe Ala Pro Pro
                    420                 425                 430

Phe Cys Leu Thr Arg Asp Glu Ala Asp Glu Ile Val Ala Lys Thr Ala
                    435                 440                 445

Ala Ala Val Lys Ala Val Leu Gly
            450                 455

<210> SEQ ID NO 33
<211> LENGTH: 460
<212> TYPE: PRT
<213> ORGANISM: Artificial Sequence
<220> FEATURE:
<223> OTHER INFORMATION: mutant transaminase

<400> SEQUENCE: 33

Met Leu Thr Asn Asp Gln Leu Ser Gln Trp Asp Gln Asp His Phe Phe
1               5                   10                  15

His Pro Ser Thr Ala Leu Gly Ala His Ala Arg Gly Glu Ala Pro Gly
                20                  25                  30

Met Val Val Gln Thr Ala Glu Gly Cys His Ile Thr Asp Arg Asn Gly
            35                  40                  45

Asn Arg Met Leu Asp Ala Phe Ala Gly Leu Trp Cys Val Asn Ile Gly
```

```
            50                  55                  60
Tyr Gly Arg Gln Glu Val Ala Glu Ala Ile Ala Ala Gln Ala Arg Glu
 65                  70                  75                  80

Leu Ala Tyr Tyr His Ser Phe Met Gly Asn Gly Thr Glu Ala Ser Ile
                     85                  90                  95

Thr Leu Ala Lys Met Val Thr Glu Arg Ala Pro Glu Gly Met Asn Arg
                    100                 105                 110

Val Tyr Phe Gly Gln Gly Gly Ser Asp Ala Asn Glu Thr Asn Ile Lys
                    115                 120                 125

Leu Val Trp Tyr Tyr Asn Asn Ile Leu Gly Arg Pro Glu Lys Lys Lys
                    130                 135                 140

Ile Val Ser Arg Trp Arg Gly Phe His Gly Ser Gly Leu Met Ser Gly
145                 150                 155                 160

Ser Leu Thr Gly Leu Ser Leu Phe His Arg Lys Phe Asp Leu Pro Leu
                    165                 170                 175

Asp Lys Val Leu His Thr Thr Ala Pro Tyr Tyr Phe Gln Arg Glu Asn
                    180                 185                 190

Val Ala Gln Ser Glu Gln Glu Phe Thr Ala Gln Cys Val Ala Asp Leu
                    195                 200                 205

Glu Glu Leu Ile Ala Arg Glu Gly Ala Asp Thr Ile Ala Ala Phe Ile
210                 215                 220

Ala Glu Pro Val Ile Gly Ala Gly Gly Ile Val Pro Pro Glu Gly
225                 230                 235                 240

Tyr Trp Asn Ala Ile Gln Pro Val Leu Lys Arg His Asp Ile Leu Leu
                    245                 250                 255

Ile Ala Asp Glu Val Ile Thr Gly Phe Gly Arg Leu Gly Ala Met Phe
                    260                 265                 270

Gly Ser Pro Leu Tyr Gly Ile Glu Pro Asp Ile Met Thr Ile Ala Lys
                    275                 280                 285

Gly Leu Thr Ser Ala Tyr Ala Pro Leu Ser Gly Ser Ile Val His Asp
                    290                 295                 300

Arg Val Trp Asp Val Leu Ala Arg Gly Thr Asp Glu Asn Gly Pro Leu
305                 310                 315                 320

Gly His Gly Trp Thr Tyr Ser Ala His Pro Ile Gly Ala Ala Ala Gly
                    325                 330                 335

Val Ala Asn Leu Thr Leu Leu Asp Thr Leu Gly Leu Val Asp Asn Ala
                    340                 345                 350

Ala Asp Val Gly Pro Tyr Leu Thr Ala Gln Met Arg Ala Ala Met Gln
                    355                 360                 365

Asp His Ala His Val Gly Asp Ile Arg Gly Val Gly Met Leu Thr Ala
                    370                 375                 380

Val Glu Leu Val Ala Asp Arg Asp Lys Gly Ser Gly Val Gly Ala Gly
385                 390                 395                 400

Phe Asp Pro Ala Ala Lys Ile Val Pro Gln Ile Ser Ala Ala Met Ala
                    405                 410                 415

Lys His Gly Val Ile Ala Arg Ala Met Pro Gln Ala Asp Ile Val Gly
                    420                 425                 430

Phe Ser Pro Pro Leu Cys Leu Thr Arg Ala Glu Ala Asp Thr Ile Val
                    435                 440                 445

Ser Val Thr Ala Glu Ala Val Ala Glu Val Leu Gly
450                 455                 460

<210> SEQ ID NO 34
```

<211> LENGTH: 464
<212> TYPE: PRT
<213> ORGANISM: Artificial Sequence
<220> FEATURE:
<223> OTHER INFORMATION: mutant transaminase

<400> SEQUENCE: 34

Met Leu Asp His Pro Ala Pro Ala Ser Asn Ala Phe Asp Ser Trp Asp
1               5                   10                  15

Arg Asp His Phe Phe His Pro Ser Thr His Met Gly Gln His Ala Arg
            20                  25                  30

Gly Glu Thr Pro Asn Arg Ile Ile Thr Gly Ala Glu Gly Val Tyr Ile
        35                  40                  45

Val Asp Arg Glu Gly Arg Arg Ser Leu Asp Ala Phe Gly Gly Leu Trp
    50                  55                  60

Cys Val Asn Val Gly Tyr Gly Arg Ser Lys Ile Thr Asp Ala Ile Ala
65                  70                  75                  80

Glu Gln Ala Ser Lys Leu Ala Tyr Tyr His Ala Phe Ala Gly His Gly
                85                  90                  95

Ser Glu Pro Ser Ile Arg Leu Ala Arg Met Val Ile Glu Arg Ala Pro
            100                 105                 110

Ala Gly Met Ser Arg Val Phe Phe Gly Leu Ser Gly Ser Asp Ala Asn
        115                 120                 125

Glu Thr Asn Ile Lys Leu Val Trp Tyr Ile Asn Asn Val Leu Gly Arg
    130                 135                 140

Pro Gln Lys Lys Lys Ile Ile Ser Arg Trp Arg Gly Phe His Gly Ser
145                 150                 155                 160

Gly Val Met Thr Gly Ser Leu Thr Gly Leu Ala Gly Phe His Lys Leu
                165                 170                 175

Phe Asp Leu Pro Arg Ala Pro Ile Leu His Thr Glu Ala Pro Tyr Tyr
            180                 185                 190

Phe Arg Arg Glu Asp Arg Ser Met Ser Glu Glu Gln Phe Ser Gln His
        195                 200                 205

Cys Ala Asp Arg Leu Glu Glu Met Ile Leu Thr Glu Gly Ala Asp Thr
    210                 215                 220

Ile Ala Ala Phe Ile Gly Glu Pro Val Leu Gly Ala Gly Gly Ile Val
225                 230                 235                 240

Pro Pro Pro Ala Gly Tyr Trp Pro Lys Ile Gln Ala Val Leu Lys Lys
                245                 250                 255

Tyr Asp Ile Met Leu Ile Ala Asp Glu Val Val Thr Gly Phe Gly Arg
            260                 265                 270

Leu Gly Ser Met Phe Gly Ser Asp His Tyr Gly Ile Glu Pro Asp Leu
        275                 280                 285

Ile Thr Ile Ala Lys Gly Leu Thr Ser Ala Tyr Ala Pro Leu Ser Gly
    290                 295                 300

Val Ile Val Ser Glu Lys Val Trp Arg Val Leu Glu Gln Gly Ser Asp
305                 310                 315                 320

Glu Phe Gly Pro Ile Gly His Gly Trp Thr Tyr Ser Ser His Pro Leu
                325                 330                 335

Cys Thr Ala Ala Gly Val Ala Asn Leu Glu Leu Val Asp Glu Leu Asp
            340                 345                 350

Leu Val Thr Asn Ala Arg Glu Thr Gly Ala Tyr Phe Asn Ala Ala Leu
        355                 360                 365

Lys Asp Ala Leu Ser Gly His Arg His Val Gly Glu Val Arg Gly Glu
    370                 375                 380

```
Gly Leu Leu Ala Ala Val Glu Leu Val Arg Asp Arg Asp Arg Thr
385                 390                 395                 400

Phe Phe Glu Ala Ser Glu Lys Val Gly Pro Arg Val Ala Ala Met
            405                 410                 415

Leu Glu Arg Gly Val Ile Ala Arg Ala Met Pro Gln Gly Asp Ile Leu
        420                 425                 430

Gly Phe Ala Pro Pro Leu Cys Leu Thr Arg Glu Glu Ala Asp Ile Val
        435                 440                 445

Val Asp Ala Thr Arg Gly Ala Val Glu Ala Val Cys Ala Thr Leu Gly
    450                 455                 460

<210> SEQ ID NO 35
<211> LENGTH: 457
<212> TYPE: PRT
<213> ORGANISM: Artificial Sequence
<220> FEATURE:
<223> OTHER INFORMATION: mutant transaminase

<400> SEQUENCE: 35

Met Leu Arg Asn Asp Gln Leu Ala Glu Trp Asp Arg Glu Asn Phe Phe
1               5                   10                  15

His Ala Ser Thr His Leu Ala Ala His Ala Arg Gly Asp Thr Pro Thr
            20                  25                  30

Arg Ile Ile Thr Gly Gly Glu Gly Val Tyr Ile Gln Asp Arg Asp Gly
        35                  40                  45

Ala Lys Ile Leu Asp Gly Phe Ala Gly Leu Trp Cys Val Asn Val Gly
    50                  55                  60

Tyr Gly Arg Arg Glu Ile Thr Asp Ala Ile Ala Ala Gln Val Ser Glu
65              70                  75                  80

Leu Ser Tyr Tyr His Ala Phe Ala Gly His Gly Thr Glu Ala Ser Val
            85                  90                  95

Thr Leu Ala Lys Met Val Leu Asp Arg Ala Pro Asp Asn Met Ser Lys
        100                 105                 110

Val Tyr Phe Gly Leu Gly Gly Ser Asp Ala Asn Glu Thr Asn Ile Lys
    115                 120                 125

Leu Ile Trp Tyr Tyr Asn Asn Ile Leu Gly Arg Pro Glu Lys Lys Lys
130                 135                 140

Ile Ile Ser Arg Trp Arg Gly Phe His Gly Ser Gly Leu Met Thr Gly
145                 150                 155                 160

Ser Leu Thr Gly Leu Gly Leu Phe His Ala Lys Phe Asp Leu Pro Met
            165                 170                 175

Asp Gly Val Leu His Thr Glu Ala Pro His Tyr Leu His Arg Ala Asp
        180                 185                 190

Arg Asn Gln Thr Glu Glu Gln Phe Ser Ala Tyr Cys Ala Ala Lys Leu
    195                 200                 205

Glu Glu Met Ile Leu Ala Glu Gly Pro Asp Thr Ile Ala Ala Phe Ile
210                 215                 220

Gly Glu Pro Ile Leu Gly Ala Gly Gly Ile Val Pro Pro Lys Gly
225                 230                 235                 240

Tyr Trp Ala Ala Ile Gln Ala Val Leu Arg Lys Tyr Asp Ile Leu Leu
            245                 250                 255

Val Val Asp Glu Val Val Thr Gly Phe Gly Arg Leu Gly Thr Met Phe
        260                 265                 270

Gly Ser Glu His Tyr Gly Leu Lys Ala Asp Leu Ile Thr Ile Ala Lys
    275                 280                 285
```

Gly Leu Thr Ser Ala Tyr Ala Pro Leu Ser Gly Ser Ile Val Ser Lys
        290                 295                 300

Lys Met Trp Ala Val Leu Glu Lys Gly Thr Asp Glu Asn Gly Ala Phe
305                 310                 315                 320

Gly His Gly Trp Thr Tyr Ser Ala His Pro Ile Gly Ala Ala Ala Gly
                    325                 330                 335

Val Ala Asn Leu Lys Leu Ile Asp Asp Leu Gly Leu Ile Ala Asn Ala
                340                 345                 350

Ser Glu Thr Gly Ala Tyr Leu Lys Ser Ala Leu Gln Ala Ala Leu Gly
            355                 360                 365

Asp His Pro Asn Val Ala Glu Ile Arg Gly Glu Gly Met Leu Ala Ala
        370                 375                 380

Val Glu Phe Cys Ala Asp Arg Asp Asp Leu Lys Gln Phe Asp Thr Ser
385                 390                 395                 400

Ala Thr Ile Gly Pro Arg Leu Ala Ala Glu Leu Leu Thr Arg Gly Val
                405                 410                 415

Ile Gly Arg Ala Met Pro Gln Ser Asp Thr Ile Gly Phe Ala Pro Pro
                420                 425                 430

Leu Cys Ile Thr Arg Ala Glu Val Asp Gln Ile Val Ala Ala Met Lys
                435                 440                 445

Gly Ala Val Asp Ala Val Leu Pro Ala
    450                 455

<210> SEQ ID NO 36
<211> LENGTH: 456
<212> TYPE: PRT
<213> ORGANISM: Artificial Sequence
<220> FEATURE:
<223> OTHER INFORMATION: mutant transaminase

<400> SEQUENCE: 36

Met Leu Thr Asn Asp Gln Leu Asp Arg Phe Asp Arg Glu Asn Phe Phe
1               5                   10                  15

His Pro Ser Thr His Leu Ala Gln His Ala Arg Gly Glu Ser Pro Ser
            20                  25                  30

Arg Ile Val Lys Thr Ala Lys Gly Val Phe Ile Glu Asp Arg Asp Gly
        35                  40                  45

Asn Lys Leu Leu Asp Gly Phe Gly Gly Leu Trp Cys Val Asn Val Gly
    50                  55                  60

Tyr Gly Gln Glu Ser Ile Ile Glu Ala Ile Ala Glu Gln Ala Lys Glu
65                  70                  75                  80

Leu Ala Tyr Tyr His Ala Phe Ala Gly His Gly Thr Glu Ala Ser Ile
                85                  90                  95

Asn Leu Ala Lys Met Val Ile Asp Arg Ala Pro Asp His Met Ser Lys
            100                 105                 110

Val Tyr Phe Gly Leu Ser Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Met Thr Gly
145                 150                 155                 160

Ser Leu Thr Gly Leu Ala Gly Phe Gln Arg Lys Phe Asp Leu Pro Leu
                165                 170                 175

Glu Arg Val Phe His Thr Thr Ala Pro Tyr Tyr Arg Arg Lys Asp
            180                 185                 190

Leu Ala Met Ser Glu Ala Asp Phe Val Ala His Cys Val Ala Glu Leu
            195                 200                 205

Glu Met Arg Ile Glu Arg Glu Gly Ala Asp Thr Ile Ala Ala Phe Ile
        210                 215                 220

Gly Glu Pro Val Leu Gly Ala Gly Ile Val Pro Pro Glu Gly
225                 230                 235                 240

Tyr Trp Lys Ala Ile Ser Ala Val Leu Glu Lys His Asp Ile Leu Leu
                245                 250                 255

Ile Ala Asp Glu Val Val Thr Gly Phe Gly Arg Leu Gly Ser Met Phe
            260                 265                 270

Gly Ser Asp His Tyr Gly Leu Lys Pro Asp Leu Ile Thr Ile Ala Lys
        275                 280                 285

Gly Leu Thr Ser Ala Tyr Ala Pro Leu Ser Gly Thr Ile Val Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Glu Leu Gly Leu Val Lys Asn Ala
            340                 345                 350

Ala Glu Thr Gly Ala Tyr Leu Arg Ala Ala Met Lys Asp Ala Leu Ser
        355                 360                 365

Asp His Pro His Val Gly Asp Ile Arg Gly Glu Gly Met Leu Met Ala
    370                 375                 380

Val Glu Phe Val Lys Asp Arg Glu Ser Arg Thr Phe Tyr Asp Pro Ser
385                 390                 395                 400

Glu Lys Val Gly Pro Asn Leu Ala Ala Leu Ile Ser Glu Gly Val
                405                 410                 415

Ile Ala Arg Ala Met Pro Glu Gly Asp Ile Leu Gly Tyr Ala Pro Pro
            420                 425                 430

Leu Cys Leu Thr Arg Glu Glu Ala Asp Gln Ile Val Ala Ala Thr Lys
        435                 440                 445

Lys Ala Val Ile Ala Val Leu Gly
    450                 455

<210> SEQ ID NO 37
<211> LENGTH: 457
<212> TYPE: PRT
<213> ORGANISM: Artificial Sequence
<220> FEATURE:
<223> OTHER INFORMATION: mutant transaminase

<400> SEQUENCE: 37

Met Leu Lys Asn Asp Gln Leu Asp Gln Trp Asp Arg Glu Asn Phe Phe
1               5                   10                  15

His Pro Ser Thr His Leu Ala Gln His Ala Arg Gly Asp Ser Ala Asn
            20                  25                  30

Arg Val Ile Lys Thr Ala Ser Gly Val Phe Ile Glu Asp Arg Asp Gly
        35                  40                  45

Asn Lys Leu Leu Asp Ala Phe Ala Gly Leu Trp Cys Val Asn Val Gly
    50                  55                  60

Tyr Gly Arg Gln Glu Ile Ala Asp Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Ala Asn Met Ser Lys
            100                 105                 110

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
            130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
            165                 170                 175

Asn Gln Val Ile His Thr Glu Ala Pro Tyr Tyr Phe Arg Arg Ala Asp
            180                 185                 190

Pro Asp Gln Ser Glu Ala Gln Phe Val Ala His Cys Ala Ala Glu Leu
            195                 200                 205

Glu Ala Leu Ile Glu Arg Glu Gly Ala Asp Thr Ile Ala Ala Phe Ile
            210                 215                 220

Gly Glu Pro Val Leu Gly Ala Gly Gly Ile Val Pro Pro Ala Gly
225                 230                 235                 240

Tyr Trp Glu Ala Ile Gln Ala Val Leu Arg Lys His Asp Ile Leu Leu
            245                 250                 255

Ile Ala Asp Glu Val Val Thr Gly Phe Gly Arg Leu Gly Thr Met Phe
            260                 265                 270

Gly Ser Asp His Tyr Gly Ile Glu Ala Asp Ile Ile Thr Ile Ala Lys
            275                 280                 285

Gly Leu Thr Ser Ala Tyr Ala Pro Leu Ser Gly Ser Ile Ile Ser Asp
            290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
            325                 330                 335

Val Ala Asn Leu Lys Leu Ile Asp Arg Leu Asn Leu Val Gln Asn Ala
            340                 345                 350

Gly Glu Thr Gly Ala Tyr Leu Asn Ala Thr Met Thr Glu Ala Leu Ala
            355                 360                 365

Gly His Pro Asn Val Gly Glu Val Arg Gly Ala Gly Met Leu Cys Ala
            370                 375                 380

Val Glu Phe Val Lys Asp Lys Asp Ser Arg Leu Phe Asp Ala Ala
385                 390                 395                 400

Asp Lys Ile Gly Pro Gln Ile Ser Ala Lys Leu Leu Glu Gln Asp Lys
            405                 410                 415

Val Ile Ala Arg Ala Met Pro Gln Gly Asp Ile Leu Gly Phe Ala Pro
            420                 425                 430

Pro Phe Cys Leu Ser Arg Ala Glu Ala Asp Gln Val Val Asp Ala Thr
            435                 440                 445

Leu Arg Ala Val Arg Thr Val Leu Gly
            450                 455

<210> SEQ ID NO 38
<211> LENGTH: 456
<212> TYPE: PRT
<213> ORGANISM: Artificial Sequence
<220> FEATURE:
<223> OTHER INFORMATION: mutant transaminase

<400> SEQUENCE: 38

```
Met Leu Thr Asn Asp Gln Leu Ser Gln Trp Asp Arg Glu Asn Phe Phe
1               5                   10                  15

His Pro Ser Thr His Leu Ala Gln His Ala Arg Gly Glu Thr Ala Thr
            20                  25                  30

Arg Val Ile Thr Thr Gly Gln Gly Cys His Ile Glu Asp Arg Asp Gly
        35                  40                  45

Thr Lys Leu Leu Asp Ala Phe Ala Gly Leu Trp Cys Val Asn Val Gly
    50                  55                  60

Tyr Gly Arg Thr Glu Ile Ala Asp Ala Ile Ala Ala Gln Ala Lys Glu
65                  70                  75                  80

Leu Ala Tyr Tyr His Ala Phe Val Gly His Gly Thr Glu Ala Ser Ile
                85                  90                  95

Thr Leu Ser Lys Met Ile Leu Asp Arg Ala Pro Ala His Met Ser Lys
            100                 105                 110

Val Tyr Phe Gly Leu Ser Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Met Thr Gly
145                 150                 155                 160

Ser Leu Thr Gly Leu Glu Leu Phe His Lys Lys Phe Asp Leu Pro Leu
                165                 170                 175

Ala Gln Val Ile His Thr Glu Ala Pro Tyr Tyr Phe Arg Arg Pro Asp
            180                 185                 190

Leu Ala Met Ser Glu Glu Ala Phe Ser Ala Tyr Cys Ala Ala Glu Leu
    195                 200                 205

Glu Gln Leu Ile Glu Arg Glu Gly Ala Asp Thr Ile Ala Ala Phe Ile
210                 215                 220

Gly Glu Pro Val Leu Gly Ala Gly Ile Val Pro Pro Lys Gly
225                 230                 235                 240

Tyr Trp Glu Ala Ile Gln Pro Ile Leu Glu Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Lys Pro Asp Leu Ile Thr Ile Ala Lys
        275                 280                 285

Gly Leu Thr Ser Ala Tyr Ala Pro Leu Ser Gly Ser Ile Val Gly Asp
    290                 295                 300

Lys Met Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Asp Met Asn Leu Val Ala Asn Ala
            340                 345                 350

Gly Glu Thr Gly Ala His Phe Arg Lys Ala Met Thr Asp Ala Leu Gly
        355                 360                 365

Asp His Ala Lys Val Gly Asp Ile Arg Gly Glu Gly Met Leu Cys Ala
    370                 375                 380

Val Glu Leu Val Asp Asp Lys Asp Asn Arg Thr Phe Phe Asp Pro Ser
385                 390                 395                 400

Gln Lys Val Gly Ala Gln Ile Ala Ser Ala Leu Leu Ser Lys Gly Val
                405                 410                 415
```

```
Ile Ala Arg Ala Met Pro Gln Gly Asp Ile Leu Gly Phe Ala Pro Pro
            420                 425                 430

Leu Cys Leu Thr Pro Ala Glu Ala Glu Val Ala Thr Lys Thr Gly
            435                 440                 445

Glu Ala Val Arg Asp Val Leu Gly
    450                 455

<210> SEQ ID NO 39
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 39

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
    50                  55                  60

Tyr Gly Arg Gln Glu Ile Ala Glu Ala Ile Ala Asp Gln Ala Arg Glu
65              70                  75                  80

Leu Ala Tyr Tyr His Ser Leu Val His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
    290                 295                 300

Lys Val Trp Lys Val Leu Glu Gln Gly Thr Asp Glu Asn Gly Pro Ile
305                 310                 315                 320
```

```
Gly His Gly Trp Thr Tyr Ser Ala His Pro Ile Gly Ala Ala Ala Gly
            325                 330                 335

Val Ala Asn Leu Lys Leu Leu Asp Glu Leu Asn Leu Val Ser Asn Ala
        340                 345                 350

Gly Glu Val Gly Ala Tyr Leu Asn Ala Thr Met Ala Glu Ala Leu Ser
        355                 360                 365

Gln His Ala Asn Val Gly Asp Val Arg Gly Glu Gly Leu Leu Cys Ala
    370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
            405                 410                 415

Ile Ile Ala Arg Ala Met Pro Gln Gly Asp Ile Leu Gly Phe Ala Pro
        420                 425                 430

Pro Phe Cys Leu Thr Arg Ala Glu Ala Asp Gln Val Val Glu Gly Thr
        435                 440                 445

Leu Arg Ala Val Lys Ala Val Leu Gly
    450                 455

<210> SEQ ID NO 40
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 40

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
            85                  90                  95

Thr Leu Ala Lys Met Ile Leu Asp Arg Ala Pro Lys Asn Met Ser Lys
        100                 105                 110

Val Tyr Phe Gly Leu Gly Gly Ser Asp Ala Asn Glu Thr Asn Val Lys
    115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
            165                 170                 175

Glu Gln Val Ile His Thr Glu Ala Pro Tyr Tyr Phe Arg Arg Glu Asp
        180                 185                 190

Leu Asn Gln Thr Glu Glu Gln Phe Val Ala His Cys Val Ala Glu Leu
    195                 200                 205

Glu Ala Leu Ile Glu Arg Glu Gly Ala Asp Thr Ile Ala Ala Phe Ile
    210                 215                 220
```

```
Gly Glu Pro Ile Leu Gly Ala Gly Gly Ile Val Pro Pro Ala Gly
225                 230                 235                 240

Tyr Trp Glu Ala Ile Gln Thr Val Leu Asn Lys His Asp Ile Leu Leu
            245                 250                 255

Val Ala Asp Glu Val Val Thr Gly Phe Gly Arg Leu Gly Thr Met Phe
        260                 265                 270

Gly Ser Asp His Tyr Gly Leu Glu Pro Asp Ile Ile Thr Ile Ala Lys
    275                 280                 285

Gly Leu Thr Ser Ala Tyr Ala Pro Leu Ser Gly Ser Ile Val Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
            325                 330                 335

Val Ala Asn Leu Lys Leu Leu Asp Glu Leu Asn Leu Val Ser Asn Ala
        340                 345                 350

Gly Glu Val Gly Ala Tyr Leu Asn Ala Thr Met Ala Glu Ala Leu Ser
    355                 360                 365

Gln His Ala Asn Val Gly Asp Val Arg Gly Glu Gly Leu Leu Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
            405                 410                 415

Ile Ile Ala Arg Ala Met His Gln Gly Asp Ile Leu Gly Phe Ala Pro
        420                 425                 430

Pro Phe Cys Leu Thr Arg Ala Glu Ala Asp Gln Val Val Glu Gly Thr
    435                 440                 445

Leu Arg Ala Val Lys Ala Val Leu Gly
450                 455
```

<210> SEQ ID NO 41
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 41

```
Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Trp Cys Val Asn Val
    50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Phe Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125
```

```
Lys Leu Ile Trp Tyr Tyr Asn Asn Val Leu Gly Arg Pro Glu Lys Lys
130                 135                 140

Lys Ile Ile Ser Arg Trp Arg Gly Phe His Gly Ser Gly Val Met Thr
145                 150                 155                 160

Gly Ser Leu Thr Gly Leu Asp Leu Phe His Asn Ala Phe Asp Leu Pro
            165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
            195                 200                 205

Leu Glu Glu Met Ile Leu Ala Glu Gly Pro Thr Ile Ala Ala Phe
210                 215                 220

Ile Gly Glu Pro Ile Leu Gly Ala Gly Gly Ile Val Pro Pro Ala
225                 230                 235                 240

Gly Tyr Trp Glu Lys Ile Gln Ala Val Leu Lys Tyr Asp Val Leu
            245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
            275                 280                 285

Lys Gly Leu Thr Ser Ala Tyr Ala Pro Leu Ser Gly Val Ile Val Ala
            290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
            355                 360                 365

Gly Gly His Lys Asn Val Gly Glu Val Arg Gly Asp Gly Met Leu Ala
            370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
            405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
            435                 440                 445

Ala Asp Ala Val Lys Ser Val Phe Ala Asn Leu
    450                 455

<210> SEQ ID NO 42
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 42

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
                20                  25                  30
```

```
Thr Arg Ile Met Ala Gly Gly Gly Val Thr Val Trp Asp Asn Asn
         35                  40                  45
Gly Arg Lys Ser Ile Asp Ala Phe Ala Gly Leu Trp Cys Val Asn Val
 50                  55                  60
Gly Tyr Gly Arg Gln Lys Ile Ala Asp Ala Ile Ala Thr Gln Ala Lys
 65                  70                  75                  80
Asn Leu Ala Tyr Tyr His Ala Phe Val Gly His Gly Thr Glu Ala Ser
                 85                  90                  95
Ile Thr Leu Ala Lys Met Ile Ile Asp Arg Ala Pro Lys Gly Met Ser
             100                 105                 110
Arg Val Tyr Phe Gly Leu Ser Gly Ser Asp Ala Asn Glu Thr Asn Ile
             115                 120                 125
Lys Leu Ile Trp Tyr Tyr Asn Asn Val Leu Gly Arg Pro Glu Lys Lys
     130                 135                 140
Lys Ile Ile Ser Arg Trp Arg Gly Tyr His Gly Ser Gly Val Met Thr
145                 150                 155                 160
Gly Ser Leu Thr Gly Leu Asp Leu Phe His Asn Ala Phe Asp Leu Pro
                 165                 170                 175
Arg Ala Pro Val Leu His Thr Glu Ala Pro Tyr Tyr Phe Arg Arg Thr
             180                 185                 190
Asp Arg Ser Met Ser Glu Glu Gln Phe Ser Gln His Cys Ala Asp Lys
             195                 200                 205
Leu Glu Glu Met Ile Leu Ala Glu Gly Pro Glu Thr Ile Ala Ala Phe
     210                 215                 220
Ile Gly Glu Pro Ile Leu Gly Ala Gly Gly Ile Val Pro Pro Ala
225                 230                 235                 240
Gly Tyr Trp Glu Lys Ile Gln Ala Val Leu Lys Lys Tyr Asp Val Leu
                 245                 250                 255
Leu Val Ala Asp Glu Val Val Thr Gly Phe Gly Arg Leu Gly Thr Met
             260                 265                 270
Phe Gly Ser Asp His Tyr Gly Ile Lys Pro Asp Leu Ile Thr Ile Ala
             275                 280                 285
Lys Gly Leu Thr Ser Ala Tyr Ala Pro Leu Ser Gly Val Ile Val Ala
     290                 295                 300
Asp Arg Val Trp Gln Val Leu Val Gln Gly Ser Asp Lys Leu Gly Ser
305                 310                 315                 320
Leu Gly His Gly Trp Thr Tyr Ser Ala His Pro Ile Cys Val Ala Ala
                 325                 330                 335
Gly Val Ala Asn Leu Glu Leu Ile Asp Glu Met Asp Leu Val Thr Asn
             340                 345                 350
Ala Gly Glu Thr Gly Ala Tyr Phe Arg Ala Glu Leu Ala Lys Ala Val
             355                 360                 365
Gly Gly His Lys Asn Val Gly Glu Val Arg Gly Asp Gly Met Leu Ala
     370                 375                 380
Ala Val Glu Phe Val Ala Asp Lys Asp Arg Val Phe Phe Asp Ala
385                 390                 395                 400
Ser Gln Lys Ile Gly Pro Gln Val Ala Thr Ala Leu Ala Ala Ser Gly
                 405                 410                 415
Val Ile Gly Arg Ala Met His Gln Asp Ile Leu Gly Phe Ala Pro
             420                 425                 430
Pro Leu Cys Leu Thr Arg Glu Gln Ala Asp Ile Val Val Ser Lys Thr
     435                 440                 445
Ala Asp Ala Val Lys Ser Val Phe Ala Asn Leu
```

<210> SEQ ID NO 43
<211> LENGTH: 457
<212> TYPE: PRT
<213> ORGANISM: Artificial Sequence
<220> FEATURE:
<223> OTHER INFORMATION: mutant transaminase

<400> SEQUENCE: 43

| Met | Leu | Lys | Asn | Asp | Gln | Leu | Asp | Gln | Trp | Asp | Arg | Asp | Asn | Phe | Phe |
|---|---|---|---|---|---|---|---|---|---|---|---|---|---|---|---|
| 1 | | | | 5 | | | | | 10 | | | | | 15 | |

| His | Pro | Ser | Thr | His | Leu | Ala | Gln | His | Ala | Arg | Gly | Glu | Ser | Ala | Asn |
| | | | 20 | | | | | 25 | | | | | 30 | | |

| Arg | Val | Ile | Lys | Thr | Ala | Ser | Gly | Val | Phe | Ile | Glu | Asp | Arg | Asp | Gly |
| | | | 35 | | | | 40 | | | | | 45 | | | |

| Thr | Lys | Leu | Leu | Asp | Ala | Phe | Ala | Gly | Leu | Trp | Cys | Val | Asn | Val | Gly |
| | 50 | | | | | 55 | | | | | 60 | | | | |

| Tyr | Gly | Arg | Gln | Glu | Ile | Ala | Glu | Ala | Ile | Ala | Asp | Gln | Ala | Arg | Glu |
| 65 | | | | | 70 | | | | | 75 | | | | | 80 |

| Leu | Ala | Tyr | Tyr | His | Ser | Phe | Val | Gly | His | Gly | Thr | Glu | Ala | Ser | Ile |
| | | | | 85 | | | | | 90 | | | | | 95 | |

| Thr | Leu | Ala | Lys | Met | Ile | Leu | Asp | Arg | Ala | Pro | Lys | Asn | Met | Ser | Lys |
| | | | 100 | | | | | 105 | | | | | 110 | | |

| Val | Tyr | Phe | Gly | Leu | Gly | Gly | Ser | Asp | Ala | Asn | Glu | Thr | Asn | Val | Lys |
| | | | 115 | | | | 120 | | | | | 125 | | | |

| Leu | Ile | Trp | Tyr | Tyr | Asn | Asn | Ile | Leu | Gly | Arg | Pro | Glu | Lys | Lys | Lys |
| | 130 | | | | | 135 | | | | | 140 | | | | |

| Ile | Ile | Ser | Arg | Trp | Arg | Gly | Phe | His | Gly | Ser | Gly | Leu | Val | Thr | Gly |
| 145 | | | | | 150 | | | | | 155 | | | | | 160 |

| Ser | Leu | Thr | Gly | Leu | Glu | Leu | Phe | His | Lys | Lys | Phe | Asp | Leu | Pro | Val |
| | | | | 165 | | | | | 170 | | | | | 175 | |

| Glu | Gln | Val | Ile | His | Thr | Glu | Ala | Pro | Tyr | Tyr | Phe | Arg | Arg | Glu | Asp |
| | | | 180 | | | | | 185 | | | | | 190 | | |

| Leu | Asn | Gln | Thr | Glu | Glu | Gln | Phe | Val | Ala | His | Cys | Val | Ala | Glu | Leu |
| | | | 195 | | | | 200 | | | | | 205 | | | |

| Glu | Ala | Leu | Ile | Glu | Arg | Glu | Gly | Ala | Asp | Thr | Ile | Ala | Ala | Phe | Ile |
| | 210 | | | | | 215 | | | | | 220 | | | | |

| Gly | Glu | Pro | Ile | Leu | Gly | Ala | Gly | Gly | Ile | Val | Pro | Pro | Ala | Gly |
| 225 | | | | | 230 | | | | | 235 | | | | | 240 |

| Tyr | Trp | Glu | Ala | Ile | Gln | Thr | Val | Leu | Asn | Lys | His | Asp | Ile | Leu | Leu |
| | | | | 245 | | | | | 250 | | | | | 255 | |

| Val | Ala | Asp | Glu | Val | Val | Thr | Gly | Phe | Gly | Arg | Leu | Gly | Thr | Met | Phe |
| | | | 260 | | | | | 265 | | | | | 270 | | |

| Gly | Ser | Asp | His | Tyr | Gly | Leu | Glu | Pro | Asp | Ile | Ile | Thr | Ile | Ala | Lys |
| | | | 275 | | | | 280 | | | | | 285 | | | |

| Gly | Leu | Thr | Ser | Ala | Tyr | Ala | Pro | Leu | Ser | Gly | Ser | Ile | Val | Ser | Asp |
| | 290 | | | | | 295 | | | | | 300 | | | | |

| Lys | Val | Trp | Lys | Val | Leu | Glu | Gln | Gly | Thr | Asp | Glu | Asn | Gly | Pro | Ile |
| 305 | | | | | 310 | | | | | 315 | | | | | 320 |

| Gly | His | Gly | Trp | Thr | Tyr | Ser | Ala | His | Pro | Ile | Gly | Ala | Ala | Ala | Gly |
| | | | | 325 | | | | | 330 | | | | | 335 | |

| Val | Ala | Asn | Leu | Lys | Leu | Leu | Asp | Glu | Leu | Asn | Leu | Val | Ser | Asn | Ala |
| | | | 340 | | | | | 345 | | | | | 350 | | |

| Gly | Glu | Val | Gly | Ala | Tyr | Leu | Asn | Ala | Thr | Met | Ala | Glu | Ala | Leu | Ser |

```
                355                 360                 365
Gln His Ala Asn Val Gly Asp Val Arg Gly Glu Gly Leu Leu Cys Ala
370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met His Gln Gly Asp Ile Leu Gly Phe Ala Pro
                420                 425                 430

Pro Phe Cys Leu Thr Arg Ala Glu Ala Asp Gln Val Val Glu Gly Thr
                435                 440                 445

Leu Arg Ala Val Lys Ala Val Leu Gly
450                 455

<210> SEQ ID NO 44
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 44

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
                20                  25                  30

Thr Arg Ile Met Ala Gly Gly Glu Gly Val Thr Val Trp Asp Asn Asn
            35                  40                  45

Gly Arg Lys Ser Ile Asp Ala Phe Ala Gly Leu Trp Cys Val Asn Val
    50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Phe Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Val Leu Gly Arg Pro Glu Lys Lys
    130                 135                 140

Lys Ile Ile Ser Arg Trp Arg Gly Phe His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
    210                 215                 220

Ile Gly Glu Pro Ile Leu Gly Ala Gly Gly Ile Val Pro Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
```

```
                260                 265                 270
Phe Gly Ser Asp His Tyr Gly Ile Lys Pro Asp Leu Ile Thr Ile Ala
            275                 280                 285
Lys Gly Leu Thr Ser Ala Tyr Ala Pro Leu Ser Gly Val Ile Val Ala
        290                 295                 300
Asp Arg Val Trp Gln Val Leu Val Gln Gly Ser Asp Lys Leu Gly Ser
305                 310                 315                 320
Leu Gly His Gly Trp Thr Tyr Ser Ala His Pro Ile Cys Val Ala Ala
                325                 330                 335
Gly Val Ala Asn Leu Glu Leu Ile Asp Glu Met Asp Leu Val Thr Asn
            340                 345                 350
Ala Gly Glu Thr Gly Ala Tyr Phe Arg Ala Glu Leu Ala Lys Ala Val
        355                 360                 365
Gly Gly His Lys Asn Val Gly Glu Val Arg Gly Asp Gly Met Leu Ala
        370                 375                 380
Ala Val Glu Phe Val Ala Asp Lys Asp Arg Val Phe Phe Asp Ala
385                 390                 395                 400
Ser Gln Lys Ile Gly Pro Gln Val Ala Thr Ala Leu Ala Ala Ser Gly
                405                 410                 415
Val Ile Gly Arg Ala Met His Gln Gly Asp Ile Leu Gly Phe Ala Pro
            420                 425                 430
Pro Leu Cys Leu Thr Arg Glu Gln Ala Asp Ile Val Val Ser Lys Thr
        435                 440                 445
Ala Asp Ala Val Lys Ser Val Phe Ala Asn Leu
    450                 455

<210> SEQ ID NO 45
<211> LENGTH: 456
<212> TYPE: PRT
<213> ORGANISM: Artificial Sequence
<220> FEATURE:
<223> OTHER INFORMATION: mutant transaminase

<400> SEQUENCE: 45

Met Leu Lys Asn Asp Pro Leu Glu Gln Trp Asp Arg Asp His Phe Leu
1               5                   10                  15
His Pro Ser Thr His Leu Ala Glu Phe Ala Arg Gly Asn Val Ala His
            20                  25                  30
Arg Ile Val Ser Gly Gly Glu Gly Ser His Ile Val Asp Arg Asn Gly
        35                  40                  45
Thr Arg Leu Leu Asp Gly Phe Ala Gly Leu Trp Cys Val Asn Val Gly
    50                  55                  60
Tyr Gly Arg Arg Glu Ile Ala Asp Ala Ile Ala Lys Gln Ala Arg Glu
65                  70                  75                  80
Leu Ser Tyr Tyr His Ser Phe Val Gly His Gly Thr Glu Ala Ser Val
                85                  90                  95
Thr Leu Ala His Met Ile Leu Glu Arg Ala Pro Ala Asn Met Ser Lys
            100                 105                 110
Val Phe Phe Gly Leu Gly Gly Ser Asp Ala Asn Glu Thr Asn Ile Lys
        115                 120                 125
Leu Ile Trp Tyr Met Asn Asn Ile Leu Gly Arg Pro Gly Lys Lys Lys
    130                 135                 140
Ile Ile Ser Arg Trp Arg Gly Phe His Gly Ser Gly Leu Met Ser Gly
145                 150                 155                 160
Ser Leu Thr Gly Leu Pro Leu Phe His Lys Ala Phe Asp Leu Pro Leu
```

```
                165                 170                 175
Ala Pro Ile Leu His Thr Glu Ala Pro Tyr Tyr Arg Arg Pro Asn
            180                 185                 190

Ala Asp Met Ser Glu Glu Ala Phe Ser Ala Trp Cys Ala Ser Glu Leu
        195                 200                 205

Glu Ala Met Ile Gln Arg Glu Gly Pro Asp Thr Ile Ala Ala Phe Trp
    210                 215                 220

Ala Glu Pro Val Leu Gly Ala Gly Ile Val Pro Pro Glu Gly
225                 230                 235                 240

Tyr Trp Ala Ala Ile Gln Glu Val Leu Asp Arg His Asp Ile Leu Leu
                245                 250                 255

Val Ala Asp Glu Val Ile Thr Gly Phe Gly Arg Leu Gly Thr Met Phe
            260                 265                 270

Gly Ser Asp His Tyr Gly Met Lys Pro Asp Val Ile Thr Ile Ala Lys
        275                 280                 285

Gly Leu Thr Ser Ala Tyr Ala Pro Leu Ser Gly Ser Val Leu Ser Glu
    290                 295                 300

Lys Val Trp Lys Val Leu Glu Gln Gly Thr Asp Glu Met Gly Ala Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Glu Leu Gly Leu Ile Asp Asn Ala
            340                 345                 350

Ala Glu Val Gly Ala His Leu Arg Ala Gly Met Arg Asp Ala Leu Gly
        355                 360                 365

Glu His Pro Asn Val Gly Asp Ile Arg Gly Glu Gly Met Leu Cys Ala
    370                 375                 380

Val Glu Leu Val Ser Asp Arg Glu Ser Lys Glu Gly Phe Asp Pro Ser
385                 390                 395                 400

Arg Lys Val Thr Val Asn Ala Val Ala His Leu Met Glu Asn Gly Val
                405                 410                 415

Ile Gly Arg Ala Met Pro His Ser Glu Thr Ile Gly Phe Ala Pro Pro
            420                 425                 430

Phe Cys Leu Thr Arg Asp Glu Ala Asp Glu Ile Val Ala Lys Thr Ala
        435                 440                 445

Ala Ala Val Lys Ala Val Leu Gly
    450                 455

<210> SEQ ID NO 46
<211> LENGTH: 460
<212> TYPE: PRT
<213> ORGANISM: Artificial Sequence
<220> FEATURE:
<223> OTHER INFORMATION: mutant transaminase

<400> SEQUENCE: 46

Met Leu Thr Asn Asp Gln Leu Ser Gln Trp Asp Gln Asp His Phe Phe
1               5                   10                  15

His Pro Ser Thr Ala Leu Gly Ala His Ala Arg Gly Glu Ala Pro Gly
            20                  25                  30

Met Val Val Gln Thr Ala Glu Gly Cys His Ile Thr Asp Arg Asn Gly
        35                  40                  45

Asn Arg Met Leu Asp Ala Phe Ala Gly Leu Trp Cys Val Asn Ile Gly
    50                  55                  60

Tyr Gly Arg Gln Glu Val Ala Glu Ala Ile Ala Ala Gln Ala Arg Glu
```

```
                65                  70                  75                  80
Leu Ala Tyr Tyr His Ser Phe Met Gly Asn Gly Thr Glu Ala Ser Ile
                    85                  90                  95

Thr Leu Ala Lys Met Val Thr Glu Arg Ala Pro Glu Gly Met Asn Arg
                100                 105                 110

Val Tyr Phe Gly Gln Gly Gly Ser Asp Ala Asn Glu Thr Asn Ile Lys
                115                 120                 125

Leu Val Trp Tyr Tyr Asn Asn Ile Leu Gly Arg Pro Glu Lys Lys Lys
            130                 135                 140

Ile Val Ser Arg Trp Arg Gly Phe His Gly Ser Gly Leu Met Ser Gly
145                 150                 155                 160

Ser Leu Thr Gly Leu Ser Leu Phe His Arg Lys Phe Asp Leu Pro Leu
                165                 170                 175

Asp Lys Val Leu His Thr Thr Ala Pro Tyr Tyr Phe Gln Arg Glu Asn
                180                 185                 190

Val Ala Gln Ser Glu Gln Glu Phe Thr Ala Gln Cys Val Ala Asp Leu
            195                 200                 205

Glu Glu Leu Ile Ala Arg Glu Gly Ala Asp Thr Ile Ala Ala Phe Ile
        210                 215                 220

Ala Glu Pro Val Ile Gly Ala Gly Gly Ile Val Pro Pro Glu Gly
225                 230                 235                 240

Tyr Trp Asn Ala Ile Gln Pro Val Leu Lys Arg His Asp Ile Leu Leu
                245                 250                 255

Ile Ala Asp Glu Val Ile Thr Gly Phe Gly Arg Leu Gly Ala Met Phe
            260                 265                 270

Gly Ser Pro Leu Tyr Gly Ile Glu Pro Asp Ile Met Thr Ile Ala Lys
        275                 280                 285

Gly Leu Thr Ser Ala Tyr Ala Pro Leu Ser Gly Ser Ile Val His Asp
        290                 295                 300

Arg Val Trp Asp Val Leu Ala Arg Gly Thr Asp Glu Asn Gly Pro Leu
305                 310                 315                 320

Gly His Gly Trp Thr Tyr Ser Ala His Pro Ile Gly Ala Ala Ala Gly
                325                 330                 335

Val Ala Asn Leu Thr Leu Leu Asp Thr Leu Gly Leu Val Asp Asn Ala
            340                 345                 350

Ala Asp Val Gly Pro Tyr Leu Thr Ala Gln Met Arg Ala Ala Met Gln
        355                 360                 365

Asp His Ala His Val Gly Asp Ile Arg Gly Val Gly Met Leu Thr Ala
        370                 375                 380

Val Glu Leu Val Ala Asp Arg Asp Lys Gly Ser Gly Val Gly Ala Gly
385                 390                 395                 400

Phe Asp Pro Ala Ala Lys Ile Val Pro Gln Ile Ser Ala Ala Met Ala
                405                 410                 415

Lys His Gly Val Ile Ala Arg Ala Met His Gln Ala Asp Ile Val Gly
            420                 425                 430

Phe Ser Pro Pro Leu Cys Leu Thr Arg Ala Glu Ala Asp Thr Ile Val
        435                 440                 445

Ser Val Thr Ala Glu Ala Val Ala Glu Val Leu Gly
        450                 455                 460

<210> SEQ ID NO 47
<211> LENGTH: 464
<212> TYPE: PRT
<213> ORGANISM: Artificial Sequence
```

<220> FEATURE:
<223> OTHER INFORMATION: mutant transaminase

<400> SEQUENCE: 47

```
Met Leu Asp His Pro Ala Pro Ala Ser Asn Ala Phe Asp Ser Trp Asp
1               5                   10                  15

Arg Asp His Phe Phe His Pro Ser Thr His Met Gly Gln His Ala Arg
            20                  25                  30

Gly Glu Thr Pro Asn Arg Ile Ile Thr Gly Ala Glu Gly Val Tyr Ile
        35                  40                  45

Val Asp Arg Glu Gly Arg Arg Ser Leu Asp Ala Phe Gly Gly Leu Trp
50                  55                  60

Cys Val Asn Val Gly Tyr Gly Arg Ser Lys Ile Thr Asp Ala Ile Ala
65                  70                  75                  80

Glu Gln Ala Ser Lys Leu Ala Tyr Tyr His Ala Phe Ala Gly His Gly
                85                  90                  95

Ser Glu Pro Ser Ile Arg Leu Ala Arg Met Val Ile Glu Arg Ala Pro
            100                 105                 110

Ala Gly Met Ser Arg Val Phe Phe Gly Leu Ser Gly Ser Asp Ala Asn
        115                 120                 125

Glu Thr Asn Ile Lys Leu Val Trp Tyr Ile Asn Asn Val Leu Gly Arg
130                 135                 140

Pro Gln Lys Lys Lys Ile Ile Ser Arg Trp Arg Gly Phe His Gly Ser
145                 150                 155                 160

Gly Val Met Thr Gly Ser Leu Thr Gly Leu Ala Gly Phe His Lys Leu
                165                 170                 175

Phe Asp Leu Pro Arg Ala Pro Ile Leu His Thr Glu Ala Pro Tyr Tyr
            180                 185                 190

Phe Arg Arg Glu Asp Arg Ser Met Ser Glu Gln Phe Ser Gln His
        195                 200                 205

Cys Ala Asp Arg Leu Glu Glu Met Ile Leu Thr Glu Gly Ala Asp Thr
210                 215                 220

Ile Ala Ala Phe Ile Gly Glu Pro Val Leu Gly Ala Gly Gly Ile Val
225                 230                 235                 240

Pro Pro Pro Ala Gly Tyr Trp Pro Lys Ile Gln Ala Val Leu Lys Lys
                245                 250                 255

Tyr Asp Ile Met Leu Ile Ala Asp Glu Val Val Thr Gly Phe Gly Arg
            260                 265                 270

Leu Gly Ser Met Phe Gly Ser Asp His Tyr Gly Ile Glu Pro Asp Leu
        275                 280                 285

Ile Thr Ile Ala Lys Gly Leu Thr Ser Ala Tyr Ala Pro Leu Ser Gly
290                 295                 300

Val Ile Val Ser Glu Lys Val Trp Arg Val Leu Glu Gln Gly Ser Asp
305                 310                 315                 320

Glu Phe Gly Pro Ile Gly His Gly Trp Thr Tyr Ser Ser His Pro Leu
                325                 330                 335

Cys Thr Ala Ala Gly Val Ala Asn Leu Glu Leu Val Asp Glu Leu Asp
            340                 345                 350

Leu Val Thr Asn Ala Arg Glu Thr Gly Ala Tyr Phe Asn Ala Ala Leu
        355                 360                 365

Lys Asp Ala Leu Ser Gly His Arg His Val Gly Glu Val Arg Gly Glu
370                 375                 380

Gly Leu Leu Ala Ala Val Glu Leu Val Arg Asp Arg Asp Asp Arg Thr
385                 390                 395                 400
```

```
Phe Phe Glu Ala Ser Glu Lys Val Gly Pro Arg Val Ala Ala Met
            405                 410                 415

Leu Glu Arg Gly Val Ile Ala Arg Ala Met His Gln Gly Asp Ile Leu
            420                 425                 430

Gly Phe Ala Pro Pro Leu Cys Leu Thr Arg Glu Glu Ala Asp Ile Val
            435                 440                 445

Val Asp Ala Thr Arg Gly Ala Val Glu Ala Val Cys Ala Thr Leu Gly
    450                 455                 460

<210> SEQ ID NO 48
<211> LENGTH: 457
<212> TYPE: PRT
<213> ORGANISM: Artificial Sequence
<220> FEATURE:
<223> OTHER INFORMATION: mutant transaminase

<400> SEQUENCE: 48

Met Leu Arg Asn Asp Gln Leu Ala Glu Trp Asp Arg Glu Asn Phe Phe
1               5                   10                  15

His Ala Ser Thr His Leu Ala Ala His Ala Arg Gly Asp Thr Pro Thr
            20                  25                  30

Arg Ile Ile Thr Gly Gly Gly Val Tyr Ile Gln Asp Arg Asp Gly
        35                  40                  45

Ala Lys Ile Leu Asp Gly Phe Ala Gly Leu Trp Cys Val Asn Val Gly
    50                  55                  60

Tyr Gly Arg Arg Glu Ile Thr Asp Ala Ile Ala Ala Gln Val Ser Glu
65              70                  75                  80

Leu Ser Tyr Tyr His Ala Phe Ala Gly His Gly Thr Glu Ala Ser Val
            85                  90                  95

Thr Leu Ala Lys Met Val Leu Asp Arg Ala Pro Asp Asn Met Ser Lys
            100                 105                 110

Val Tyr Phe Gly Leu Gly Gly Ser Asp Ala Asn Glu Thr Asn Ile Lys
            115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Met Thr Gly
145                 150                 155                 160

Ser Leu Thr Gly Leu Gly Leu Phe His Ala Lys Phe Asp Leu Pro Met
            165                 170                 175

Asp Gly Val Leu His Thr Glu Ala Pro His Tyr Leu His Arg Ala Asp
            180                 185                 190

Arg Asn Gln Thr Glu Glu Gln Phe Ser Ala Tyr Cys Ala Ala Lys Leu
        195                 200                 205

Glu Glu Met Ile Leu Ala Glu Gly Pro Asp Thr Ile Ala Ala Phe Ile
    210                 215                 220

Gly Glu Pro Ile Leu Gly Ala Gly Gly Ile Val Pro Pro Lys Gly
225                 230                 235                 240

Tyr Trp Ala Ala Ile Gln Ala Val Leu Arg Lys Tyr Asp Ile Leu Leu
            245                 250                 255

Val Val Asp Glu Val Val Thr Gly Phe Gly Arg Leu Gly Thr Met Phe
            260                 265                 270

Gly Ser Glu His Tyr Gly Leu Lys Ala Asp Leu Ile Thr Ile Ala Lys
        275                 280                 285

Gly Leu Thr Ser Ala Tyr Ala Pro Leu Ser Gly Ser Ile Val Ser Lys
    290                 295                 300
```

Lys Met Trp Ala Val Leu Glu Lys Gly Thr Asp Glu Asn Gly Ala Phe
305                 310                 315                 320

Gly His Gly Trp Thr Tyr Ser Ala His Pro Ile Gly Ala Ala Ala Gly
            325                 330                 335

Val Ala Asn Leu Lys Leu Ile Asp Asp Leu Gly Leu Ile Ala Asn Ala
            340                 345                 350

Ser Glu Thr Gly Ala Tyr Leu Lys Ser Ala Leu Gln Ala Ala Leu Gly
            355                 360                 365

Asp His Pro Asn Val Ala Glu Ile Arg Gly Glu Gly Met Leu Ala Ala
            370                 375                 380

Val Glu Phe Cys Ala Asp Arg Asp Leu Lys Gln Phe Asp Thr Ser
385                 390                 395                 400

Ala Thr Ile Gly Pro Arg Leu Ala Glu Leu Leu Thr Arg Gly Val
                    405                 410                 415

Ile Gly Arg Ala Met His Gln Ser Asp Thr Ile Gly Phe Ala Pro Pro
            420                 425                 430

Leu Cys Ile Thr Arg Ala Glu Val Asp Gln Ile Val Ala Ala Met Lys
            435                 440                 445

Gly Ala Val Asp Ala Val Leu Pro Ala
    450                 455

<210> SEQ ID NO 49
<211> LENGTH: 456
<212> TYPE: PRT
<213> ORGANISM: Artificial Sequence
<220> FEATURE:
<223> OTHER INFORMATION: mutant transaminase

<400> SEQUENCE: 49

Met Leu Thr Asn Asp Gln Leu Asp Arg Phe Asp Arg Glu Asn Phe Phe
1                   5                   10                  15

His Pro Ser Thr His Leu Ala Gln His Ala Arg Gly Glu Ser Pro Ser
                20                  25                  30

Arg Ile Val Lys Thr Ala Lys Gly Val Phe Ile Glu Asp Arg Asp Gly
            35                  40                  45

Asn Lys Leu Leu Asp Gly Phe Gly Gly Leu Trp Cys Val Asn Val Gly
        50                  55                  60

Tyr Gly Gln Glu Ser Ile Ile Glu Ala Ile Ala Glu Gln Ala Lys Glu
65                  70                  75                  80

Leu Ala Tyr Tyr His Ala Phe Ala Gly His Gly Thr Glu Ala Ser Ile
                85                  90                  95

Asn Leu Ala Lys Met Val Ile Asp Arg Ala Pro Asp His Met Ser Lys
            100                 105                 110

Val Tyr Phe Gly Leu Ser Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
        130                 135                 140

Ile Ile Ser Arg Trp Arg Gly Phe His Gly Ser Gly Leu Met Thr Gly
145                 150                 155                 160

Ser Leu Thr Gly Leu Ala Gly Phe Gln Arg Lys Phe Asp Leu Pro Leu
                165                 170                 175

Glu Arg Val Phe His Thr Thr Ala Pro Tyr Tyr Tyr Arg Arg Lys Asp
            180                 185                 190

Leu Ala Met Ser Glu Ala Asp Phe Val Ala His Cys Val Ala Glu Leu
        195                 200                 205

-continued

```
Glu Met Arg Ile Glu Arg Gly Ala Asp Thr Ile Ala Ala Phe Ile
    210                 215                 220

Gly Glu Pro Val Leu Gly Ala Gly Gly Ile Val Pro Pro Glu Gly
225                 230                 235                 240

Tyr Trp Lys Ala Ile Ser Ala Val Leu Glu Lys His Asp Ile Leu Leu
                245                 250                 255

Ile Ala Asp Glu Val Val Thr Gly Phe Gly Arg Leu Gly Ser Met Phe
                260                 265                 270

Gly Ser Asp His Tyr Gly Leu Lys Pro Asp Leu Ile Thr Ile Ala Lys
            275                 280                 285

Gly Leu Thr Ser Ala Tyr Ala Pro Leu Ser Gly Thr Ile Val Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Glu Leu Gly Leu Val Lys Asn Ala
            340                 345                 350

Ala Glu Thr Gly Ala Tyr Leu Arg Ala Ala Met Lys Asp Ala Leu Ser
    355                 360                 365

Asp His Pro His Val Gly Asp Ile Arg Gly Glu Gly Met Leu Met Ala
370                 375                 380

Val Glu Phe Val Lys Asp Arg Glu Ser Arg Thr Phe Tyr Asp Pro Ser
385                 390                 395                 400

Glu Lys Val Gly Pro Asn Leu Ala Ala Leu Ile Ser Glu Gly Val
                405                 410                 415

Ile Ala Arg Ala Met His Glu Gly Asp Ile Leu Gly Tyr Ala Pro Pro
            420                 425                 430

Leu Cys Leu Thr Arg Glu Glu Ala Asp Gln Ile Val Ala Ala Thr Lys
    435                 440                 445

Lys Ala Val Ile Ala Val Leu Gly
    450                 455
```

<210> SEQ ID NO 50
<211> LENGTH: 457
<212> TYPE: PRT
<213> ORGANISM: Artificial Sequence
<220> FEATURE:
<223> OTHER INFORMATION: mutant transaminase

<400> SEQUENCE: 50

```
Met Leu Lys Asn Asp Gln Leu Asp Gln Trp Asp Arg Glu Asn Phe Phe
1               5                   10                  15

His Pro Ser Thr His Leu Ala Gln His Ala Arg Gly Asp Ser Ala Asn
                20                  25                  30

Arg Val Ile Lys Thr Ala Ser Gly Val Phe Ile Glu Asp Arg Asp Gly
            35                  40                  45

Asn Lys Leu Leu Asp Ala Phe Ala Gly Leu Trp Cys Val Asn Val Gly
    50                  55                  60

Tyr Gly Arg Gln Glu Ile Ala Asp Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Ala Asn Met Ser Lys
                100                 105                 110
```

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
        130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
                165                 170                 175

Asn Gln Val Ile His Thr Glu Ala Pro Tyr Tyr Phe Arg Arg Ala Asp
            180                 185                 190

Pro Asp Gln Ser Glu Ala Gln Phe Val Ala His Cys Ala Ala Glu Leu
        195                 200                 205

Glu Ala Leu Ile Glu Arg Glu Gly Ala Asp Thr Ile Ala Ala Phe Ile
210                 215                 220

Gly Glu Pro Val Leu Gly Ala Gly Gly Ile Val Pro Pro Ala Gly
225                 230                 235                 240

Tyr Trp Glu Ala Ile Gln Ala Val Leu Arg Lys His Asp Ile Leu Leu
                245                 250                 255

Ile Ala Asp Glu Val Val Thr Gly Phe Gly Arg Leu Gly Thr Met Phe
            260                 265                 270

Gly Ser Asp His Tyr Gly Ile Glu Ala Asp Ile Ile Thr Ile Ala Lys
        275                 280                 285

Gly Leu Thr Ser Ala Tyr Ala Pro Leu Ser Gly Ser Ile Ile Ser Asp
290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Arg Leu Asn Leu Val Gln Asn Ala
            340                 345                 350

Gly Glu Thr Gly Ala Tyr Leu Asn Ala Thr Met Thr Glu Ala Leu Ala
        355                 360                 365

Gly His Pro Asn Val Gly Glu Val Arg Gly Ala Gly Met Leu Cys Ala
370                 375                 380

Val Glu Phe Val Lys Asp Lys Asp Ser Arg Leu Phe Phe Asp Ala Ala
385                 390                 395                 400

Asp Lys Ile Gly Pro Gln Ile Ser Ala Lys Leu Leu Glu Gln Asp Lys
                405                 410                 415

Val Ile Ala Arg Ala Met His Gln Gly Asp Ile Leu Gly Phe Ala Pro
            420                 425                 430

Pro Phe Cys Leu Ser Arg Ala Glu Ala Asp Gln Val Val Asp Ala Thr
        435                 440                 445

Leu Arg Ala Val Arg Thr Val Leu Gly
    450                 455

<210> SEQ ID NO 51
<211> LENGTH: 456
<212> TYPE: PRT
<213> ORGANISM: Artificial Sequence
<220> FEATURE:
<223> OTHER INFORMATION: mutant transaminase

<400> SEQUENCE: 51

Met Leu Thr Asn Asp Gln Leu Ser Gln Trp Asp Arg Glu Asn Phe Phe
1               5                   10                  15

His Pro Ser Thr His Leu Ala Gln His Ala Arg Gly Glu Thr Ala Thr
            20                  25                  30

Arg Val Ile Thr Thr Gly Gln Gly Cys His Ile Glu Asp Arg Asp Gly
            35                  40                  45

Thr Lys Leu Leu Asp Ala Phe Ala Gly Leu Trp Cys Val Asn Val Gly
    50                  55                  60

Tyr Gly Arg Thr Glu Ile Ala Asp Ala Ile Ala Gln Ala Lys Glu
65                  70                  75                  80

Leu Ala Tyr Tyr His Ala Phe Val Gly His Thr Glu Ala Ser Ile
                85                  90                  95

Thr Leu Ser Lys Met Ile Leu Asp Arg Ala Pro Ala His Met Ser Lys
            100                 105                 110

Val Tyr Phe Gly Leu Ser Gly Ser Asp Ala Asn Glu Thr Asn Ile Lys
            115                 120                 125

Leu Ile Trp Tyr Tyr Asn Asn Ile Leu Gly Arg Pro Glu Lys Lys Lys
            130                 135                 140

Ile Ile Ser Arg Trp Arg Gly Phe His Gly Ser Gly Leu Met Thr Gly
145                 150                 155                 160

Ser Leu Thr Gly Leu Glu Leu Phe His Lys Lys Phe Asp Leu Pro Leu
                165                 170                 175

Ala Gln Val Ile His Thr Glu Ala Pro Tyr Tyr Phe Arg Arg Pro Asp
            180                 185                 190

Leu Ala Met Ser Glu Glu Ala Phe Ser Ala Tyr Cys Ala Ala Glu Leu
            195                 200                 205

Glu Gln Leu Ile Glu Arg Glu Gly Ala Asp Thr Ile Ala Ala Phe Ile
            210                 215                 220

Gly Glu Pro Val Leu Gly Ala Gly Gly Ile Val Pro Pro Lys Gly
225                 230                 235                 240

Tyr Trp Glu Ala Ile Gln Pro Ile Leu Glu Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Lys Pro Asp Leu Ile Thr Ile Ala Lys
            275                 280                 285

Gly Leu Thr Ser Ala Tyr Ala Pro Leu Ser Gly Ser Ile Val Gly Asp
            290                 295                 300

Lys Met Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Asp Met Asn Leu Val Ala Asn Ala
            340                 345                 350

Gly Glu Thr Gly Ala His Phe Arg Lys Ala Met Thr Asp Ala Leu Gly
            355                 360                 365

Asp His Ala Lys Val Gly Asp Ile Arg Gly Glu Gly Met Leu Cys Ala
            370                 375                 380

Val Glu Leu Val Asp Asp Lys Asp Asn Arg Thr Phe Phe Asp Pro Ser
385                 390                 395                 400

Gln Lys Val Gly Ala Gln Ile Ala Ser Ala Leu Leu Ser Lys Gly Val
                405                 410                 415

Ile Ala Arg Ala Met His Gln Gly Asp Ile Leu Gly Phe Ala Pro Pro
            420                 425                 430

```
Leu Cys Leu Thr Pro Ala Glu Ala Glu Val Ala Thr Lys Thr Gly
            435                 440                 445

Glu Ala Val Arg Asp Val Leu Gly
            450                 455

<210> SEQ ID NO 52
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 52

Met Leu Lys Asn Asp Gln Leu Asp Gln Trp Asp Arg Asp Asn Phe Phe
 1               5                  10                  15

His Pro Ser Thr His Leu Ala Gln His Ala Arg Gly Glu Ser Ala Asn
                20                  25                  30

Arg Val Ile Lys Thr Ala Ser Gly Val Phe Ile Glu Asp Arg Asp Gly
             35                  40                  45

Thr Lys Leu Leu Asp Ala Phe Ala Gly Leu Trp Cys Val Asn Val Gly
     50                  55                  60

Tyr Gly Arg Gln Glu Ile Ala Glu Ala Ile Ala Asp Gln Ala Arg Glu
 65                  70                  75                  80

Leu Ala Tyr Tyr His Ser Phe Val Gly His Gly Thr Glu Ala Ser Ile
                 85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Gly Phe Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
    290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335
```

```
Val Ala Asn Leu Lys Leu Leu Asp Glu Leu Asn Leu Val Ser Asn Ala
                340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Glu Gly Leu Leu Cys Ala
    370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
                420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
            450                 455

<210> SEQ ID NO 53
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 53

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Trp Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Ala Gly Gly Met Val Pro Pro Ala Gly
225                 230                 235                 240
```

```
Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
            275                 280                 285

Gly Leu Thr Ser Ala Tyr Ala Pro Leu Ser Gly Ser Ile Val Ser Asp
        290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
            325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Glu Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
            420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
    450                 455

<210> SEQ ID NO 54
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 54

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
            20                  25                  30

Thr Arg Ile Met Ala Gly Gly Glu Gly Val Thr Val Trp Asp Asn Asn
        35                  40                  45

Gly Arg Lys Ser Ile Asp Ala Phe Ala Gly Leu Trp Cys Val Asn Val
    50                  55                  60

Gly Tyr Gly Arg Gln Lys Ile Ala Asp Ala Ile Ala Thr Gln Ala Lys
65                  70                  75                  80

Asn Leu Ala Tyr Tyr His Ala Phe Val Gly His Gly Thr Glu Ala Ser
                85                  90                  95

Ile Thr Leu Ala Lys Met Ile Ile Asp Arg Ala Pro Lys Gly Met Ser
            100                 105                 110

Arg Val Tyr Phe Gly Leu Ser Gly Ser Asp Ala Asn Glu Thr Asn Ile
        115                 120                 125

Lys Leu Ile Trp Tyr Tyr Asn Asn Val Leu Gly Arg Pro Glu Lys Lys
    130                 135                 140
```

Lys Ile Ile Ser Arg Trp Arg Gly Phe His Gly Ser Gly Val Met Thr
145                 150                 155                 160

Gly Ser Leu Thr Gly Leu Asp Leu Phe His Asn Ala Phe Asp Leu Pro
                165                 170                 175

Arg Ala Pro Val Leu His Thr Glu Ala Pro Tyr Tyr Phe Arg Arg Thr
            180                 185                 190

Asp Arg Ser Met Ser Glu Glu Gln Phe Ser Gln His Cys Ala Asp Lys
        195                 200                 205

Leu Glu Glu Met Ile Leu Ala Glu Gly Pro Glu Thr Ile Ala Ala Phe
    210                 215                 220

Ile Gly Glu Pro Ile Leu Gly Ala Gly Gly Phe Val Pro Pro Ala
225                 230                 235                 240

Gly Tyr Trp Glu Lys Ile Gln Ala Val Leu Lys Lys Tyr Asp Val Leu
                245                 250                 255

Leu Val Ala Asp Glu Val Val Thr Gly Phe Gly Arg Leu Gly Thr Met
            260                 265                 270

Phe Gly Ser Asp His Tyr Gly Ile Lys Pro Asp Leu Ile Thr Ile Ala
        275                 280                 285

Lys Gly Leu Thr Ser Ala Tyr Ala Pro Leu Ser Gly Val Ile Val Ala
    290                 295                 300

Asp Arg Val Trp Gln Val Leu Val Gln Gly Ser Asp Lys Leu Gly Ser
305                 310                 315                 320

Leu Gly His Gly Trp Thr Tyr Ser Ala His Pro Ile Cys Val Ala Ala
                325                 330                 335

Gly Val Ala Asn Leu Glu Leu Ile Asp Glu Met Asp Leu Val Thr Asn
            340                 345                 350

Ala Gly Glu Thr Gly Ala Tyr Phe Arg Ala Glu Leu Ala Lys Ala Val
        355                 360                 365

Gly Gly His Lys Asn Val Gly Glu Val Arg Gly Asp Gly Met Leu Ala
    370                 375                 380

Ala Val Glu Phe Val Ala Asp Lys Asp Arg Val Phe Phe Asp Ala
385                 390                 395                 400

Ser Gln Lys Ile Gly Pro Gln Val Ala Thr Ala Leu Ala Ala Ser Gly
                405                 410                 415

Val Ile Gly Arg Ala Met Pro Gln Gly Asp Ile Leu Gly Phe Ala Pro
            420                 425                 430

Pro Leu Cys Leu Thr Arg Glu Gln Ala Asp Ile Val Val Ser Lys Thr
        435                 440                 445

Ala Asp Ala Val Lys Ser Val Phe Ala Asn Leu
    450                 455

<210> SEQ ID NO 55
<211> LENGTH: 459
<212> TYPE: PRT
<213> ORGANISM: Artificial Sequence
<220> FEATURE:
<223> OTHER INFORMATION: Mutant Transaminase

<400> SEQUENCE: 55

Met Leu Asn Gln Ser Asn Glu Leu Asn Ala Trp Asp Arg Asp His Phe
1               5                   10                  15

Phe His Pro Ser Thr His Met Gly Thr His Ala Arg Gly Glu Ser Pro
                20                  25                  30

Thr Arg Ile Met Ala Gly Gly Glu Gly Val Thr Val Trp Asp Asn Asn
            35                  40                  45

-continued

```
Gly Arg Lys Ser Ile Asp Ala Phe Ala Gly Leu Trp Cys Val Asn Val
 50                  55                  60
Gly Tyr Gly Arg Gln Lys Ile Ala Asp Ala Ile Ala Thr Gln Ala Lys
 65                  70                  75                  80
Asn Leu Ala Tyr Tyr His Ala Phe Val Gly His Gly Thr Glu Ala Ser
                     85                  90                  95
Ile Thr Leu Ala Lys Met Ile Ile Asp Arg Ala Pro Lys Gly Met Ser
                100                 105                 110
Arg Val Tyr Phe Gly Leu Ser Gly Ser Asp Ala Asn Glu Thr Asn Ile
                115                 120                 125
Lys Leu Ile Trp Tyr Tyr Asn Asn Val Leu Gly Arg Pro Glu Lys Lys
130                 135                 140
Lys Ile Ile Ser Arg Trp Arg Gly Phe His Gly Ser Gly Val Met Thr
145                 150                 155                 160
Gly Ser Leu Thr Gly Leu Asp Leu Phe His Asn Ala Phe Asp Leu Pro
                165                 170                 175
Arg Ala Pro Val Leu His Thr Glu Ala Pro Tyr Tyr Phe Arg Arg Thr
                180                 185                 190
Asp Arg Ser Met Ser Glu Glu Gln Phe Ser Gln His Cys Ala Asp Lys
                195                 200                 205
Leu Glu Glu Met Ile Leu Ala Glu Gly Pro Glu Thr Ile Ala Ala Phe
210                 215                 220
Ile Gly Glu Pro Ile Leu Gly Ala Gly Gly Met Val Pro Pro Pro Ala
225                 230                 235                 240
Gly Tyr Trp Glu Lys Ile Gln Ala Val Leu Lys Lys Tyr Asp Val Leu
                245                 250                 255
Leu Val Ala Asp Glu Val Val Thr Gly Phe Gly Arg Leu Gly Thr Met
                260                 265                 270
Phe Gly Ser Asp His Tyr Gly Ile Lys Pro Asp Leu Ile Thr Ile Ala
                275                 280                 285
Lys Gly Leu Thr Ser Ala Tyr Ala Pro Leu Ser Gly Val Ile Val Ala
                290                 295                 300
Asp Arg Val Trp Gln Val Leu Val Gln Gly Ser Asp Lys Leu Gly Ser
305                 310                 315                 320
Leu Gly His Gly Trp Thr Tyr Ser Ala His Pro Ile Cys Val Ala Ala
                325                 330                 335
Gly Val Ala Asn Leu Glu Leu Ile Asp Glu Met Asp Leu Val Thr Asn
                340                 345                 350
Ala Gly Glu Thr Gly Ala Tyr Phe Arg Ala Glu Leu Ala Lys Ala Val
                355                 360                 365
Gly Gly His Lys Asn Val Gly Glu Val Arg Gly Asp Gly Met Leu Ala
                370                 375                 380
Ala Val Glu Phe Val Ala Asp Lys Asp Asp Arg Val Phe Phe Asp Ala
385                 390                 395                 400
Ser Gln Lys Ile Gly Pro Gln Val Ala Thr Ala Leu Ala Ala Ser Gly
                405                 410                 415
Val Ile Gly Arg Ala Met Pro Gln Gly Asp Ile Leu Gly Phe Ala Pro
                420                 425                 430
Pro Leu Cys Leu Thr Arg Glu Gln Ala Asp Ile Val Val Ser Lys Thr
                435                 440                 445
Ala Asp Ala Val Lys Ser Val Phe Ala Asn Leu
450                 455
```

```
<210> SEQ ID NO 56
<211> LENGTH: 7
<212> TYPE: PRT
<213> ORGANISM: Artificial Sequence
<220> FEATURE:
<223> OTHER INFORMATION: tag

<400> SEQUENCE: 56

Ser His His His His His His
1               5

<210> SEQ ID NO 57
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 57

Met Leu Lys Asn Asp Gln Leu Asp Gln Trp Asp Arg Asp Asn Phe Phe
1               5                   10                  15

His Pro Ser Thr His Leu Ala Gln His Ala Arg Gly Glu Ser Ala Asn
            20                  25                  30

Arg Val Ile Lys Thr Ala Ser Gly Val Phe Ile Glu Asp Arg Asp Gly
        35                  40                  45

Thr Lys Leu Leu Asp Ala Phe Ala Gly Leu Phe Cys Val Asn Val Gly
    50                  55                  60

Tyr Gly Arg Gln Glu Ile Ala Glu Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Lys Asn Met Ser Lys
            100                 105                 110

Val Tyr Phe Gly Leu Gly Gly Ser Asp Ala Asn Glu Thr Asn Val Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Tyr His Gly Ser Gly Leu Val Thr Gly
145                 150                 155                 160

Ser Leu Thr Gly Leu Glu Leu Phe His Lys Lys Phe Asp Leu Pro Val
                165                 170                 175

Glu Gln Val Ile His Thr Glu Ala Pro Tyr Tyr Phe Arg Arg Glu Asp
            180                 185                 190

Leu Asn Gln Thr Glu Glu Gln Phe Val Ala His Cys Val Ala Glu Leu
        195                 200                 205

Glu Ala Leu Ile Glu Arg Glu Gly Ala Asp Thr Ile Ala Ala Phe Ile
    210                 215                 220

Gly Glu Pro Ile Leu Gly Gly Gly Ile Val Pro Pro Ala Gly
225                 230                 235                 240

Tyr Trp Glu Ala Ile Gln Thr Val Leu Asn Lys His Asp Ile Leu Leu
                245                 250                 255

Val Ala Asp Glu Val Val Thr Gly Phe Gly Arg Leu Gly Thr Met Phe
            260                 265                 270

Gly Ser Asp His Tyr Gly Leu Glu Pro Asp Ile Ile Thr Ile Ala Lys
        275                 280                 285

Gly Leu Thr Ser Ala Tyr Ala Pro Leu Ser Gly Ser Ile Val Ser Asp
    290                 295                 300
```

```
Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
            325                 330                 335

Val Ala Asn Leu Lys Leu Leu Asp Glu Leu Asn Leu Val Ser Asn Ala
            340                 345                 350

Gly Glu Val Gly Ala Tyr Leu Asn Ala Thr Met Ala Glu Ala Leu Ser
            355                 360                 365

Gln His Ala Asn Val Gly Asp Val Arg Gly Gly Leu Leu Cys Ala
        370                 375                 380

Val Glu Phe Val Lys Asp Arg Asp Ser Arg Thr Phe Phe Asp Ala Ala
385                 390                 395                 400

Asp Lys Ile Gly Pro Gln Ile Ser Ala Lys Leu Leu Glu Gln Asp Lys
                405                 410                 415

Ile Ile Ala Arg Ala Met Pro Gln Gly Asp Ile Leu Gly Phe Ala Pro
                420                 425                 430

Pro Phe Cys Leu Thr Arg Ala Glu Ala Asp Gln Val Val Glu Gly Thr
            435                 440                 445

Leu Arg Ala Val Lys Ala Val Leu Gly
    450                 455

<210> SEQ ID NO 58
<211> LENGTH: 456
<212> TYPE: PRT
<213> ORGANISM: Artificial Sequence
<220> FEATURE:
<223> OTHER INFORMATION: Mutant Transaminase

<400> SEQUENCE: 58

Met Leu Lys Asn Asp Pro Leu Glu Gln Trp Asp Arg Asp His Phe Leu
1               5                   10                  15

His Pro Ser Thr His Leu Ala Glu Phe Ala Arg Gly Asn Val Ala His
            20                  25                  30

Arg Ile Val Ser Gly Gly Glu Gly Ser His Ile Val Asp Arg Asn Gly
        35                  40                  45

Thr Arg Leu Leu Asp Gly Phe Ala Gly Leu Trp Cys Val Asn Val Gly
50                  55                  60

Tyr Gly Arg Arg Glu Ile Ala Asp Ala Ile Ala Lys Gln Ala Arg Glu
65                  70                  75                  80

Leu Ser Tyr Tyr His Ser Phe Val Gly His Gly Thr Glu Ala Ser Val
                85                  90                  95

Thr Leu Ala His Met Ile Leu Glu Arg Ala Pro Ala Asn Met Ser Lys
            100                 105                 110

Val Phe Phe Gly Leu Gly Gly Ser Asp Ala Asn Glu Thr Asn Ile Lys
        115                 120                 125

Leu Ile Trp Tyr Met Asn Asn Ile Leu Gly Arg Pro Gly Lys Lys Lys
130                 135                 140

Ile Ile Ser Arg Trp Arg Gly Phe His Gly Ser Gly Leu Met Ser Gly
145                 150                 155                 160

Ser Leu Thr Gly Leu Pro Leu Phe His Lys Ala Phe Asp Leu Pro Leu
                165                 170                 175

Ala Pro Ile Leu His Thr Glu Ala Pro Tyr Tyr Arg Arg Pro Asn
            180                 185                 190

Ala Asp Met Ser Glu Glu Ala Phe Ser Ala Trp Cys Ala Ser Glu Leu
        195                 200                 205
```

```
Glu Ala Met Ile Gln Arg Glu Gly Pro Asp Thr Ile Ala Ala Phe Trp
            210                 215                 220

Ala Glu Pro Val Leu Gly Ala Gly Met Val Pro Pro Glu Gly
225                 230                 235                 240

Tyr Trp Ala Ala Ile Gln Glu Val Leu Asp Arg His Asp Ile Leu Leu
                245                 250                 255

Val Ala Asp Glu Val Ile Thr Gly Phe Gly Arg Leu Gly Thr Met Phe
                260                 265                 270

Gly Ser Asp His Tyr Gly Met Lys Pro Asp Val Ile Thr Ile Ala Lys
            275                 280                 285

Gly Leu Thr Ser Ala Tyr Ala Pro Leu Ser Gly Ser Val Leu Ser Glu
            290                 295                 300

Lys Val Trp Lys Val Leu Glu Gln Gly Thr Asp Glu Met Gly Ala Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Glu Leu Gly Leu Ile Asp Asn Ala
            340                 345                 350

Ala Glu Val Gly Ala His Leu Arg Ala Gly Met Arg Asp Ala Leu Gly
            355                 360                 365

Glu His Pro Asn Val Gly Asp Ile Arg Gly Glu Gly Met Leu Cys Ala
            370                 375                 380

Val Glu Leu Val Ser Asp Arg Glu Ser Lys Glu Gly Phe Asp Pro Ser
385                 390                 395                 400

Arg Lys Val Thr Val Asn Ala Val Ala His Leu Met Glu Asn Gly Val
                405                 410                 415

Ile Gly Arg Ala Met Pro His Ser Glu Thr Ile Gly Phe Ala Pro Pro
            420                 425                 430

Phe Cys Leu Thr Arg Asp Glu Ala Asp Glu Ile Val Ala Lys Thr Ala
            435                 440                 445

Ala Ala Val Lys Ala Val Leu Gly
    450                 455

<210> SEQ ID NO 59
<211> LENGTH: 460
<212> TYPE: PRT
<213> ORGANISM: Artificial Sequence
<220> FEATURE:
<223> OTHER INFORMATION: Mutant Transaminase

<400> SEQUENCE: 59

Met Leu Thr Asn Asp Gln Leu Ser Gln Trp Asp Gln Asp His Phe Phe
1               5                   10                  15

His Pro Ser Thr Ala Leu Gly Ala His Ala Arg Gly Glu Ala Pro Gly
                20                  25                  30

Met Val Val Gln Thr Ala Glu Gly Cys His Ile Thr Asp Arg Asn Gly
            35                  40                  45

Asn Arg Met Leu Asp Ala Phe Ala Gly Leu Trp Cys Val Asn Ile Gly
        50                  55                  60

Tyr Gly Arg Gln Glu Val Ala Glu Ala Ile Ala Ala Gln Ala Arg Glu
65                  70                  75                  80

Leu Ala Tyr Tyr His Ser Phe Met Gly Asn Gly Thr Glu Ala Ser Ile
                85                  90                  95

Thr Leu Ala Lys Met Val Thr Glu Arg Ala Pro Glu Gly Met Asn Arg
                100                 105                 110
```

-continued

```
Val Tyr Phe Gly Gln Gly Gly Ser Asp Ala Asn Glu Thr Asn Ile Lys
            115                 120                 125
Leu Val Trp Tyr Tyr Asn Asn Ile Leu Gly Arg Pro Glu Lys Lys Lys
130                 135                 140
Ile Val Ser Arg Trp Arg Gly Phe His Gly Ser Gly Leu Met Ser Gly
145                 150                 155                 160
Ser Leu Thr Gly Leu Ser Leu Phe His Arg Lys Phe Asp Leu Pro Leu
                165                 170                 175
Asp Lys Val Leu His Thr Thr Ala Pro Tyr Tyr Phe Gln Arg Glu Asn
            180                 185                 190
Val Ala Gln Ser Glu Gln Glu Phe Thr Ala Gln Cys Val Ala Asp Leu
        195                 200                 205
Glu Glu Leu Ile Ala Arg Glu Gly Ala Asp Thr Ile Ala Ala Phe Ile
210                 215                 220
Ala Glu Pro Val Ile Gly Ala Gly Gly Met Val Pro Pro Glu Gly
225                 230                 235                 240
Tyr Trp Asn Ala Ile Gln Pro Val Leu Lys Arg His Asp Ile Leu Leu
                245                 250                 255
Ile Ala Asp Glu Val Ile Thr Gly Phe Gly Arg Leu Gly Ala Met Phe
            260                 265                 270
Gly Ser Pro Leu Tyr Gly Ile Glu Pro Asp Ile Met Thr Ile Ala Lys
        275                 280                 285
Gly Leu Thr Ser Ala Tyr Ala Pro Leu Ser Gly Ser Ile Val His Asp
    290                 295                 300
Arg Val Trp Asp Val Leu Ala Arg Gly Thr Asp Glu Asn Gly Pro Leu
305                 310                 315                 320
Gly His Gly Trp Thr Tyr Ser Ala His Pro Ile Gly Ala Ala Ala Gly
                325                 330                 335
Val Ala Asn Leu Thr Leu Leu Asp Thr Leu Gly Leu Val Asp Asn Ala
            340                 345                 350
Ala Asp Val Gly Pro Tyr Leu Thr Ala Gln Met Arg Ala Ala Met Gln
        355                 360                 365
Asp His Ala His Val Gly Asp Ile Arg Gly Val Gly Met Leu Thr Ala
    370                 375                 380
Val Glu Leu Val Ala Asp Arg Asp Lys Gly Ser Gly Val Gly Ala Gly
385                 390                 395                 400
Phe Asp Pro Ala Ala Lys Ile Val Pro Gln Ile Ser Ala Ala Met Ala
                405                 410                 415
Lys His Gly Val Ile Ala Arg Ala Met Pro Gln Ala Asp Ile Val Gly
            420                 425                 430
Phe Ser Pro Pro Leu Cys Leu Thr Arg Ala Glu Ala Asp Thr Ile Val
        435                 440                 445
Ser Val Thr Ala Glu Ala Val Ala Glu Val Leu Gly
    450                 455                 460
```

<210> SEQ ID NO 60
<211> LENGTH: 464
<212> TYPE: PRT
<213> ORGANISM: Artificial Sequence
<220> FEATURE:
<223> OTHER INFORMATION: Mutant Transaminase

<400> SEQUENCE: 60

```
Met Leu Asp His Pro Ala Pro Ala Ser Asn Ala Phe Asp Ser Trp Asp
1               5                   10                  15
```

```
Arg Asp His Phe Phe His Pro Ser Thr His Met Gly Gln His Ala Arg
            20                  25                  30
Gly Glu Thr Pro Asn Arg Ile Ile Thr Gly Ala Glu Gly Val Tyr Ile
        35                  40                  45
Val Asp Arg Glu Gly Arg Arg Ser Leu Asp Ala Phe Gly Gly Leu Trp
50                  55                  60
Cys Val Asn Val Gly Tyr Gly Arg Ser Lys Ile Thr Asp Ala Ile Ala
65                  70                  75                  80
Glu Gln Ala Ser Lys Leu Ala Tyr Tyr His Ala Phe Ala Gly His Gly
                85                  90                  95
Ser Glu Pro Ser Ile Arg Leu Ala Arg Met Val Ile Glu Arg Ala Pro
            100                 105                 110
Ala Gly Met Ser Arg Val Phe Phe Gly Leu Ser Gly Ser Asp Ala Asn
        115                 120                 125
Glu Thr Asn Ile Lys Leu Val Trp Tyr Ile Asn Asn Val Leu Gly Arg
130                 135                 140
Pro Gln Lys Lys Lys Ile Ile Ser Arg Trp Arg Gly Phe His Gly Ser
145                 150                 155                 160
Gly Val Met Thr Gly Ser Leu Thr Gly Leu Ala Gly Phe His Lys Leu
                165                 170                 175
Phe Asp Leu Pro Arg Ala Pro Ile Leu His Thr Glu Ala Pro Tyr Tyr
            180                 185                 190
Phe Arg Arg Glu Asp Arg Ser Met Ser Glu Glu Gln Phe Ser Gln His
        195                 200                 205
Cys Ala Asp Arg Leu Glu Glu Met Ile Leu Thr Glu Gly Ala Asp Thr
210                 215                 220
Ile Ala Ala Phe Ile Gly Glu Pro Val Leu Gly Ala Gly Gly Met Val
225                 230                 235                 240
Pro Pro Pro Ala Gly Tyr Trp Pro Lys Ile Gln Ala Val Leu Lys Lys
                245                 250                 255
Tyr Asp Ile Met Leu Ile Ala Asp Glu Val Thr Gly Phe Gly Arg
            260                 265                 270
Leu Gly Ser Met Phe Gly Ser Asp His Tyr Gly Ile Glu Pro Asp Leu
        275                 280                 285
Ile Thr Ile Ala Lys Gly Leu Thr Ser Ala Tyr Ala Pro Leu Ser Gly
290                 295                 300
Val Ile Val Ser Glu Lys Val Trp Arg Val Leu Gln Gly Ser Asp
305                 310                 315                 320
Glu Phe Gly Pro Ile Gly His Gly Trp Thr Tyr Ser Ser His Pro Leu
                325                 330                 335
Cys Thr Ala Ala Gly Val Ala Asn Leu Glu Leu Val Asp Glu Leu Asp
            340                 345                 350
Leu Val Thr Asn Ala Arg Glu Thr Gly Ala Tyr Phe Asn Ala Ala Leu
        355                 360                 365
Lys Asp Ala Leu Ser Gly His Arg His Val Gly Glu Val Arg Gly Glu
370                 375                 380
Gly Leu Leu Ala Ala Val Glu Leu Val Arg Asp Arg Asp Arg Thr
385                 390                 395                 400
Phe Phe Glu Ala Ser Glu Lys Val Gly Pro Arg Val Ala Ala Ala Met
                405                 410                 415
Leu Glu Arg Gly Val Ile Ala Arg Ala Met Pro Gln Gly Asp Ile Leu
            420                 425                 430
Gly Phe Ala Pro Pro Leu Cys Leu Thr Arg Glu Glu Ala Asp Ile Val
```

```
            435                 440                 445
Val Asp Ala Thr Arg Gly Ala Val Glu Ala Val Cys Ala Thr Leu Gly
    450                 455                 460
```

<210> SEQ ID NO 61
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 61

```
Met Leu Arg Asn Asp Gln Leu Ala Glu Trp Asp Arg Glu Asn Phe Phe
1               5                   10                  15

His Ala Ser Thr His Leu Ala Ala His Ala Arg Gly Asp Thr Pro Thr
            20                  25                  30

Arg Ile Ile Thr Gly Gly Glu Gly Val Tyr Ile Gln Asp Arg Asp Gly
        35                  40                  45

Ala Lys Ile Leu Asp Gly Phe Ala Gly Leu Trp Cys Val Asn Val Gly
    50                  55                  60

Tyr Gly Arg Arg Glu Ile Thr Asp Ala Ile Ala Ala Gln Val Ser Glu
65                  70                  75                  80

Leu Ser Tyr Tyr His Ala Phe Ala Gly His Gly Thr Glu Ala Ser Val
                85                  90                  95

Thr Leu Ala Lys Met Val Leu Asp Arg Ala Pro Asp Asn Met Ser Lys
            100                 105                 110

Val Tyr Phe Gly Leu Gly Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Met Thr Gly
145                 150                 155                 160

Ser Leu Thr Gly Leu Gly Leu Phe His Ala Lys Phe Asp Leu Pro Met
                165                 170                 175

Asp Gly Val Leu His Thr Glu Ala Pro His Tyr Leu His Arg Ala Asp
            180                 185                 190

Arg Asn Gln Thr Glu Glu Gln Phe Ser Ala Tyr Cys Ala Ala Lys Leu
        195                 200                 205

Glu Glu Met Ile Leu Ala Glu Gly Pro Asp Thr Ile Ala Ala Phe Ile
    210                 215                 220

Gly Glu Pro Ile Leu Gly Ala Gly Gly Met Val Pro Pro Lys Gly
225                 230                 235                 240

Tyr Trp Ala Ala Ile Gln Ala Val Leu Arg Lys Tyr Asp Ile Leu Leu
                245                 250                 255

Val Val Asp Glu Val Val Thr Gly Phe Gly Arg Leu Gly Thr Met Phe
            260                 265                 270

Gly Ser Glu His Tyr Gly Leu Lys Ala Asp Leu Ile Thr Ile Ala Lys
        275                 280                 285

Gly Leu Thr Ser Ala Tyr Ala Pro Leu Ser Gly Ser Ile Val Ser Lys
    290                 295                 300

Lys Met Trp Ala Val Leu Glu Lys Gly Thr Asp Glu Asn Gly Ala Phe
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Asp Leu Gly Leu Ile Ala Asn Ala
```

```
                340               345                350
Ser Glu Thr Gly Ala Tyr Leu Lys Ser Ala Leu Gln Ala Ala Leu Gly
            355                 360                 365

Asp His Pro Asn Val Ala Glu Ile Arg Gly Glu Gly Met Leu Ala Ala
        370                 375                 380

Val Glu Phe Cys Ala Asp Arg Asp Leu Lys Gln Phe Asp Thr Ser
385                 390                 395                 400

Ala Thr Ile Gly Pro Arg Leu Ala Ala Glu Leu Leu Thr Arg Gly Val
                405                 410                 415

Ile Gly Arg Ala Met Pro Gln Ser Asp Thr Ile Gly Phe Ala Pro Pro
            420                 425                 430

Leu Cys Ile Thr Arg Ala Glu Val Asp Gln Ile Val Ala Ala Met Lys
            435                 440                 445

Gly Ala Val Asp Ala Val Leu Pro Ala
            450                 455

<210> SEQ ID NO 62
<211> LENGTH: 456
<212> TYPE: PRT
<213> ORGANISM: Artificial Sequence
<220> FEATURE:
<223> OTHER INFORMATION: Mutant Transaminase

<400> SEQUENCE: 62

Met Leu Thr Asn Asp Gln Leu Asp Arg Phe Asp Arg Glu Asn Phe Phe
1               5                   10                  15

His Pro Ser Thr His Leu Ala Gln His Ala Arg Gly Glu Ser Pro Ser
            20                  25                  30

Arg Ile Val Lys Thr Ala Lys Gly Val Phe Ile Glu Asp Arg Asp Gly
        35                  40                  45

Asn Lys Leu Leu Asp Gly Phe Gly Gly Leu Trp Cys Val Asn Val Gly
    50                  55                  60

Tyr Gly Gln Glu Ser Ile Ile Glu Ala Ile Ala Glu Gln Ala Lys Glu
65                  70                  75                  80

Leu Ala Tyr Tyr His Ala Phe Ala Gly His Gly Thr Glu Ala Ser Ile
                85                  90                  95

Asn Leu Ala Lys Met Val Ile Asp Arg Ala Pro Asp His Met Ser Lys
            100                 105                 110

Val Tyr Phe Gly Leu Ser Gly Ser Asp Ala Asn Glu Thr Asn Ile Lys
        115                 120                 125

Leu Ile Trp Tyr Tyr Asn Asn Ile Leu Gly Arg Pro Glu Lys Lys Lys
    130                 135                 140

Ile Ile Ser Arg Trp Arg Gly Phe His Gly Ser Gly Leu Met Thr Gly
145                 150                 155                 160

Ser Leu Thr Gly Leu Ala Gly Phe Gln Arg Lys Phe Asp Leu Pro Leu
                165                 170                 175

Glu Arg Val Phe His Thr Thr Ala Pro Tyr Tyr Arg Lys Asp
            180                 185                 190

Leu Ala Met Ser Glu Ala Asp Phe Val Ala His Cys Val Ala Glu Leu
            195                 200                 205

Glu Met Arg Ile Glu Arg Gly Ala Asp Thr Ile Ala Ala Phe Ile
            210                 215                 220

Gly Glu Pro Val Leu Gly Ala Gly Gly Met Val Pro Pro Glu Gly
225                 230                 235                 240

Tyr Trp Lys Ala Ile Ser Ala Val Leu Glu Lys His Asp Ile Leu Leu
```

```
                245                 250                 255
Ile Ala Asp Glu Val Val Thr Gly Phe Gly Arg Leu Gly Ser Met Phe
            260                 265                 270

Gly Ser Asp His Tyr Gly Leu Lys Pro Asp Leu Ile Thr Ile Ala Lys
            275                 280                 285

Gly Leu Thr Ser Ala Tyr Ala Pro Leu Ser Gly Thr Ile Val Ser Asp
            290                 295                 300

Lys Val Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Glu Leu Gly Leu Val Lys Asn Ala
            340                 345                 350

Ala Glu Thr Gly Ala Tyr Leu Arg Ala Ala Met Lys Asp Ala Leu Ser
            355                 360                 365

Asp His Pro His Val Gly Asp Ile Arg Gly Glu Gly Met Leu Met Ala
            370                 375                 380

Val Glu Phe Val Lys Asp Arg Glu Ser Arg Thr Phe Tyr Asp Pro Ser
385                 390                 395                 400

Glu Lys Val Gly Pro Asn Leu Ala Ala Leu Ile Ser Glu Gly Val
                405                 410                 415

Ile Ala Arg Ala Met Pro Glu Gly Asp Ile Leu Gly Tyr Ala Pro Pro
                420                 425                 430

Leu Cys Leu Thr Arg Glu Glu Ala Asp Gln Ile Val Ala Ala Thr Lys
                435                 440                 445

Lys Ala Val Ile Ala Val Leu Gly
450                 455

<210> SEQ ID NO 63
<211> LENGTH: 457
<212> TYPE: PRT
<213> ORGANISM: Artificial Sequence
<220> FEATURE:
<223> OTHER INFORMATION: Mutant Transaminase

<400> SEQUENCE: 63

Met Leu Lys Asn Asp Gln Leu Asp Gln Trp Asp Arg Glu Asn Phe Phe
1               5                   10                  15

His Pro Ser Thr His Leu Ala Gln His Ala Arg Gly Asp Ser Ala Asn
                20                  25                  30

Arg Val Ile Lys Thr Ala Ser Gly Val Phe Ile Glu Asp Arg Asp Gly
            35                  40                  45

Asn Lys Leu Leu Asp Ala Phe Ala Gly Leu Trp Cys Val Asn Val Gly
        50                  55                  60

Tyr Gly Arg Gln Glu Ile Ala Asp Ala Ile Ala Asp Gln Ala Arg Glu
65                  70                  75                  80

Leu Ala Tyr Tyr His Ser Phe Val Gly His Gly Thr Glu Ala Ser Ile
                85                  90                  95

Thr Leu Ala Lys Met Ile Leu Asp Arg Ala Pro Ala Asn Met Ser Lys
            100                 105                 110

Val Tyr Phe Gly Leu Gly Gly Ser Asp Ala Asn Glu Thr Asn Val Lys
            115                 120                 125

Leu Ile Trp Tyr Tyr Asn Asn Ile Leu Gly Arg Pro Glu Lys Lys Lys
        130                 135                 140

Ile Ile Ser Arg Trp Arg Gly Phe His Gly Ser Gly Leu Val Thr Gly
```

```
            145                 150                 155                 160
    Ser Leu Thr Gly Leu Glu Leu Phe His Lys Lys Phe Asp Leu Pro Val
                    165                 170                 175

Asn Gln Val Ile His Thr Glu Ala Pro Tyr Tyr Phe Arg Arg Ala Asp
                    180                 185                 190

Pro Asp Gln Ser Glu Ala Gln Phe Val Ala His Cys Ala Ala Glu Leu
                    195                 200                 205

Glu Ala Leu Ile Glu Arg Glu Gly Ala Asp Thr Ile Ala Ala Phe Ile
                    210                 215                 220

Gly Glu Pro Val Leu Gly Ala Gly Gly Met Val Pro Pro Ala Gly
    225                 230                 235                 240

Tyr Trp Glu Ala Ile Gln Ala Val Leu Arg Lys His Asp Ile Leu Leu
                    245                 250                 255

Ile Ala Asp Glu Val Val Thr Gly Phe Gly Arg Leu Gly Thr Met Phe
                    260                 265                 270

Gly Ser Asp His Tyr Gly Ile Glu Ala Asp Ile Ile Thr Ile Ala Lys
                    275                 280                 285

Gly Leu Thr Ser Ala Tyr Ala Pro Leu Ser Gly Ser Ile Ile Ser Asp
                    290                 295                 300

Lys Val Trp Lys Val Leu Glu Gln Gly Thr Asp Glu Asn Gly Pro Ile
    305                 310                 315                 320

Gly His Gly Trp Thr Tyr Ser Ala His Pro Ile Gly Ala Ala Ala Gly
                    325                 330                 335

Val Ala Asn Leu Lys Leu Ile Asp Arg Leu Asn Leu Val Gln Asn Ala
                    340                 345                 350

Gly Glu Thr Gly Ala Tyr Leu Asn Ala Thr Met Thr Glu Ala Leu Ala
                    355                 360                 365

Gly His Pro Asn Val Gly Glu Val Arg Gly Ala Gly Met Leu Cys Ala
                    370                 375                 380

Val Glu Phe Val Lys Asp Lys Asp Ser Arg Leu Phe Phe Asp Ala Ala
    385                 390                 395                 400

Asp Lys Ile Gly Pro Gln Ile Ser Ala Lys Leu Leu Glu Gln Asp Lys
                    405                 410                 415

Val Ile Ala Arg Ala Met Pro Gln Gly Asp Ile Leu Gly Phe Ala Pro
                    420                 425                 430

Pro Phe Cys Leu Ser Arg Ala Glu Ala Asp Gln Val Val Asp Ala Thr
                    435                 440                 445

Leu Arg Ala Val Arg Thr Val Leu Gly
        450                 455

<210> SEQ ID NO 64
<211> LENGTH: 456
<212> TYPE: PRT
<213> ORGANISM: Artificial Sequence
<220> FEATURE:
<223> OTHER INFORMATION: Mutant Transaminase

<400> SEQUENCE: 64

Met Leu Thr Asn Asp Gln Leu Ser Gln Trp Asp Arg Glu Asn Phe Phe
1               5                   10                  15

His Pro Ser Thr His Leu Ala Gln His Ala Arg Gly Glu Thr Ala Thr
                20                  25                  30

Arg Val Ile Thr Thr Gly Gln Gly Cys His Ile Glu Asp Arg Asp Gly
            35                  40                  45

Thr Lys Leu Leu Asp Ala Phe Ala Gly Leu Trp Cys Val Asn Val Gly
```

```
                50              55              60
Tyr Gly Arg Thr Glu Ile Ala Asp Ala Ile Ala Ala Gln Ala Lys Glu
 65                      70                  75                  80

Leu Ala Tyr Tyr His Ala Phe Val Gly His Gly Thr Glu Ala Ser Ile
                         85                  90                  95

Thr Leu Ser Lys Met Ile Leu Asp Arg Ala Pro Ala His Met Ser Lys
                    100                 105                 110

Val Tyr Phe Gly Leu Ser Gly Ser Asp Ala Asn Glu Thr Asn Ile Lys
                115                 120                 125

Leu Ile Trp Tyr Tyr Asn Asn Ile Leu Gly Arg Pro Glu Lys Lys Lys
            130                 135                 140

Ile Ile Ser Arg Trp Arg Gly Phe His Gly Ser Gly Leu Met Thr Gly
145                 150                 155                 160

Ser Leu Thr Gly Leu Glu Leu Phe His Lys Phe Asp Leu Pro Leu
                165                 170                 175

Ala Gln Val Ile His Thr Glu Ala Pro Tyr Tyr Phe Arg Arg Pro Asp
                180                 185                 190

Leu Ala Met Ser Glu Glu Ala Phe Ser Ala Tyr Cys Ala Ala Glu Leu
                195                 200                 205

Glu Gln Leu Ile Glu Arg Glu Gly Ala Asp Thr Ile Ala Ala Phe Ile
210                 215                 220

Gly Glu Pro Val Leu Gly Ala Gly Gly Met Val Pro Pro Lys Gly
225                 230                 235                 240

Tyr Trp Glu Ala Ile Gln Pro Ile Leu Glu Lys His Asp Ile Leu Leu
                245                 250                 255

Val Ala Asp Glu Val Val Thr Gly Phe Gly Arg Leu Gly Thr Met Phe
                260                 265                 270

Gly Ser Asp His Tyr Gly Leu Lys Pro Asp Leu Ile Thr Ile Ala Lys
                275                 280                 285

Gly Leu Thr Ser Ala Tyr Ala Pro Leu Ser Gly Ser Ile Val Gly Asp
                290                 295                 300

Lys Met Trp Lys Val Leu Glu Gln Gly Thr Asp Glu Asn Gly Pro Ile
305                 310                 315                 320

Gly His Gly Trp Thr Tyr Ser Ala His Pro Ile Gly Ala Ala Ala Gly
                325                 330                 335

Val Ala Asn Leu Lys Leu Ile Asp Asp Met Asn Leu Val Ala Asn Ala
                340                 345                 350

Gly Glu Thr Gly Ala His Phe Arg Lys Ala Met Thr Asp Ala Leu Gly
                355                 360                 365

Asp His Ala Lys Val Gly Asp Ile Arg Gly Glu Gly Met Leu Cys Ala
                370                 375                 380

Val Glu Leu Val Asp Asp Lys Asp Asn Arg Thr Phe Phe Asp Pro Ser
385                 390                 395                 400

Gln Lys Val Gly Ala Gln Ile Ala Ser Ala Leu Leu Ser Lys Gly Val
                405                 410                 415

Ile Ala Arg Ala Met Pro Gln Gly Asp Ile Leu Gly Phe Ala Pro Pro
                420                 425                 430

Leu Cys Leu Thr Pro Ala Glu Ala Glu Glu Val Ala Thr Lys Thr Gly
                435                 440                 445

Glu Ala Val Arg Asp Val Leu Gly
                450                 455
```

MUTANT TRANSAMINASES AS WELL AS METHODS AND USES RELATING THERETO

CROSS REFERENCE TO RELATED APPLICATIONS

This application claims priority to European Application No. 15001113.8 filed Apr. 16, 2015, the disclosure of which is incorporated hereby reference in its entirety.

SEQUENCE LISTING

This application contains a Sequence Listing submitted via EFS-Web and hereby incorporated by reference in its entirety. Said ASCII copy, created on Apr. 12, 2016, is named SeqListing_P32802.txt, and is 248,762 bytes in size.

Scheme 1:

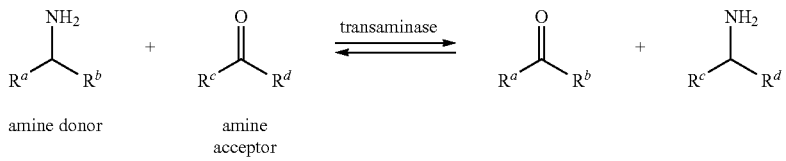

amine donor  amine acceptor

The present invention relates to a mutant transaminase with increased transaminase activity relative to the wild-type transaminase, a fusion protein comprising the transaminase, a polynucleotide coding for the transaminase, a host cell comprising the polynucleotide, mutant transaminase and/or fusion protein, a method of producing an amine with the mutant transaminase or fusion protein and the use of the mutant transaminase or fusion protein for the production of an amine.

Transaminases (also referred to as aminotransferases) catalyze a transamination reaction, i.e. the transfer of an amino group from an amine donor to an amine acceptor, particularly the amination of a ketone along with the deamination of an amine, wherein the $NH_2$ group on one molecule or domain is exchanged with the =O group on the other molecule or domain (cf. Scheme 1).

Amine compounds such as chiral amines are significant building blocks for pharmaceutical, agrochemical or chemical industry. In many of these applications, it is of significant importance that only one optically pure form is used. Chemical synthesis has been established for the production of such compounds (for instance asymmetric hydrogenation using transition metals) however, these chemical processes are far from being perfect with respect to yield, purity and waste generation. Transaminase-catalyzed production of amines is an often advantageous alternative to classical methods, therefor alternative or improved transaminases are of interest in the field.

The production of chiral amines via enzyme-mediated transamination is beneficial compared to established chemical asymmetric synthesis, as it was nicely presented in the production of the drug sitagliptin by using an engineered (R)-selective transaminase (Savile et al., 2010; US 2015/0037869). In this case, an initially inactive amine transaminase (ATA) towards the desired substrate was extensively engineered via directed evolution methods. Further mutants of transaminases are described in the art (Steffen-Munsberg et al., 2013; Nobili et al., 2015 Deszcz et al., 2015). Also other enzymes can be used for the production of optically pure chiral amines and amino acids, such as mono amine oxidases, imine reductases, amino acid dehydrogenases, ammonia lyases or amino mutases. Although transaminases can be used for the kinetic resolution of racemic amines, the asymmetric synthesis from keto acids, ketones or aldehydes is of most importance, as they can potentially lead to a theoretical 100% conversion, compared to only 50% theoretical yield in the kinetic resolution mode (cf. Scheme 1 illustrating synthesis as well as kinetic resolution).

The residues $R^a$, $R^b$, $R^c$ and $R^d$ have been applied for illustrative purpose only and shall represent common organic residues.

However, the directed evolution approaches do not provide us with an insight for the molecular reasons e.g. with respect to the acceptance of the bulkier substrates. The high enantioselectivity of transaminases fueled the theory of the big and small binding pocket, however, enlarging the small binding pocket to accommodate bulky substrates is a target not easily attained, as illustrated by the fact that by far most of the successful examples found in literature are transaminases converting methylketones.

The target of the present invention was to design mutant transaminases with increased transaminase activity relative to the wild-type transaminase. Preferably, they should be capable of accepting a wide spectrum of substrates, particularly bulky substrates, especially while maintaining stereoselectivity, as well as to use iso-propylamine as amine donor. Accordingly, an increased activity is of particular relevance for bulky substrates (an exemplified selection is depicted in Schemes 2 and 3, see below) as well as for the amine donor iso-propylamine. These stereoselective transaminases can be used for the asymmetric synthesis of chiral amines from the respective ketones as well as for kinetic resolution.

Surprisingly, it has been found that a mutant transaminase comprising an amino acid sequence that is at least 65% identical to the amino acid sequence of SEQ ID NO: 1 (*Ruegeria* sp. TM1040 transaminase; referred to as 3FCR) and having at least two amino acid substitutions relative to the wild-type transaminase, wherein the amino acid at the position corresponding to position 59 of SEQ ID NO: 1 is substituted with Trp or Phe (Trp59 or Phe59, respectively) and the amino acid at the position corresponding to position 231 of SEQ ID NO: 1 is substituted with Ala or Gly (Ala231 or Gly231, respectively) shows an increased transaminase activity relative to the wild-type transaminase.

As shown in the Examples, several amino acid residues in transaminases were identified whose substitution increases the transaminase activity of the mutant transaminase relative to the respective wild-type transaminase. Particularly, it could be shown that a double mutant of 3FCR, namely 3FCR with the substitution of Tyr with Trp at position 59 (Y59W) and the substitution of Thr with Ala at position 231 (T231A) of SEQ ID NO:1 (referred to as Y59W/T231A), had an increased activity towards substrates accepted by the wild-type (amines 3a and 4a as shown in Scheme 2), but also a low activity (~5 mU/mg) was determined towards amine 1a (see Tables 3 and 4). The results obtained with mutants of transaminase 3FCR could be confirmed with mutants of the transaminase of *Mesorhizobium loti* maff303099 (referred to as 3GJU) (see Table 3). Moreover, 3FCR mutants with the additional substitution of Tyr with Phe at position 87 and/or the additional substitution of Tyr with Phe at position 152 of SEQ ID NO:1 (referred to as Y87F and Y152F) had an increased activity towards substrates with two aromatic rings (i.e. amines 1a, 3a and 4a) (see Y59W/Y87F/T231A and Y59W/Y87F/Y152F/T231A in Table 4). At the same time mutation Y152F increased the stability of the mutant significantly (FIG. 1). An even higher increase in activity and the range of substrates accepted could be obtained by the further substitution of Pro with His at position 423 of SEQ ID NO: 1 (referred to as P423H) in transaminases of 3FCR (see Tables 3 and 4). It could be shown that mutants with substitutions Y59W, Y87F, Y152F, T231A and P423H are particularly active on bulky substrates (such as amines 1a, 3a and 4a). Again, the results obtained with mutants of transaminase 3FCR could be confirmed with mutants of 3GJU (see Table 3). Moreover, mutant transaminases of ATA-3, ATA-5, ATA-6, ATA-7, ATA-8 and ATA-9 with mutations Y59W/Y87F/Y152F/T231A were shown to be active towards amines 1a, 3a, 4a and 6a (see Table 5). Please note that the wild-type sequences ATA-3 to ATA-9 have sequence identities to wild-type 3FCR in the range of from 65-70% to approximately 90%. Thus, it can be concluded that the concept of the present invention can be transferred to all transaminase having a sequence identity to the sequence of 3FCR (SEQ ID NO: 1) of 65% or more. Additionally, 3FCR and 3GJU mutants which have an aliphatic hydrophobic amino acid in the position 87, such as Leu or Val (Y87L or Y87V, respectively), were found to have increased activity and were particularly effective for the acceptance of tertiary carbon substituents such as amine 2a (see Table 6). Mutants that have a phenylalanine in position 59 (Y59F) and/or a glycine in position 231 (T231G) show increased activity towards bicyclic compounds such as amine 5a (see Table 7). Moreover, 3FCR mutants with the substitution of Ile with Phe or Met at position 234 (referred to as I234F and I234M, respectively) had an increased activity towards amine 5a (see Table 7) and the amine donor iso-propylamine (see Table 8). Maintained stereoselectivity and suitability of the mutants in asymmetric synthesis and kinetic resolution was proven in Examples 5 to 11 (see Tables 9 to 10).

Accordingly, in a first aspect the present invention provides a mutant transaminase with increased transaminase activity relative to the wild-type transaminase, wherein the mutant transaminase comprises an amino acid sequence that is at least 65% identical to the amino acid sequence of SEQ ID NO: 1 (*Ruegeria* sp. TM1040 transaminase; referred to as 3FCR) and wherein the mutant transaminase has at least two amino acid substitutions relative to the wild-type transaminase, wherein the amino acid at the position corresponding to position 59 of SEQ ID NO: 1 is substituted with Trp or Phe (Trp59 or Phe59, respectively) and the amino acid at the position corresponding to position 231 of SEQ ID NO: 1 is substituted with Ala or Gly (Ala231 or Gly 231, respectively).

The term "transaminase" (classified as EC 2.6.1.XX by the Enzyme Commission of the International Union of Biochemistry; known also as aminotransferases) generally means an enzyme that catalyses the transfer of an amine group from an amine donor to the carbonyl group of an amine acceptor (transamination). Transaminases are pyridoxal-5'-phosphate dependent (PLP-dependent) enzymes. As seen in Scheme 1, the amine donor provides the amino group to the amine acceptor—so that the desired amine is synthesized—and a corresponding ketone is formed. As transaminases often posses a high stereoselectivity, the transamination reaction can provide the desired amine by asymmetric reduction and/or the remaining amine donor by resolution via oxidative deamination as enantiomerically enriched amine. ω-Transaminases (ω-TAs) are of particular interest in the present invention, as they are able to convert ketones without adjacent carboxylic function into chiral amines—in contrast to amino acid transaminases known for the synthesis of α-amino acids from α-keto acids. Note that the term amine transaminase (ATA) is preferred over ω-TA, as these enzymes were named for their ability to synthesize, e.g., L-lysine from the corresponding ε-aldehyde. (S)-selective ATAs have been already known since more than a decade (Coffen et al, 1994). The transaminase of the present invention may be either non-selective or selective, such as (S)-selective or (R)-selective, especially a (S)-selective transaminase. Suitable examples of these transaminases are also given in Table 1.

The term "wild-type transaminase" relates to a transaminase as it typically occurs in nature. Examples of naturally occurring wild-type transaminases are given below, in Table 1 and as SEQ ID NOs: 1, 3, and 5 to 11 (amino acid sequences). If one or more mutations are introduced a mutant transaminase is obtained. Therefore, the term "mutant transaminase" relates to a transaminase whose amino acid sequence is different from the wild-type sequence. With respect to the mutant transaminase of the present invention it is noted that the mutant is functionally active. This means that the mutant has maintained its biological function, i.e. its enzymatic activity of a transaminase. In accordance with the present invention, the transaminase activity of the mutant is increased relative to the transaminase activity of the wild-type. The wild-type transaminase corresponding to a mutant is that wild-type transaminase which differs from the mutant by a minimal number of mutations. Exemplary wild-type transaminases which may be mutated according to the present invention are listed in the following:

Aminotransferase (*Ruegeria* sp. TM1040) (GI: 499859271; referred to as 3FCR; SEQ ID NO: 1)
Transaminase (*Mesorhizobium loti* maff303099) (GI: 499217058; referred to as 3GJU; SEQ ID NO: 3)
Transaminase (*Oceanicola granulosus*) (GI: 494465841; referred to as ATA-3; SEQ ID NO: 5)
Transaminase (*Jannaschia* Sp CCS1) (GI: 499773242; referred to as ATA-4; SEQ ID NO: 6)
Transaminase (Xanthobacteraceae) (GI: 517199618; referred to as ATA-5; SEQ ID NO: 7)
Rhodobacteraceae bacterium RB2150_13166) (GI: 126705951; referred to as ATA-6; SEQ ID NO: 8)
Transaminase (*Martelella mediterranea* DSM 17316) (GI:516720233; referred to as ATA-7; SEQ ID NO: 9)
Transaminase (*Rugeria pomeroyi* DSS-3) (GI:56677770; referred to as ATA-8; SEQ ID NO: 10)
Transaminase (*Sagittula stellata* E-37) (GI:126711082; referred to as ATA-9; SEQ ID NO: 11)

Particularly preferred wild-type transaminases in which the mutations described herein may be introduced in accordance with the present invention are those specified in SEQ ID NO: 1, 3 and 5 to 11, particularly in SEQ ID NO: 1 and 3, especially SEQ ID NO: 1.

According to the present invention, the mutant transaminase has increased transaminase activity relative to the respective wild-type transaminase without mutation. Enzyme activity is a measure of the activity of enzyme. The SI unit for enzyme activity is katal (1 katal=1 mol s$^{-1}$) A more practical and commonly used value is enzyme unit (U)=1 µmol min$^{-1}$. 1 U corresponds to 16.67 nanokatals. One U is defined as the amount of the enzyme that catalyzes the conversion of 1 micro mole of substrate per minute. The conditions when measuring the activity are usually standardized: one usually takes a temperature of 25° C. or 30° C. (as in the Examples) and the pH value and substrate concentration that yields the maximal substrate conversion rate. The specific activity of an enzyme is the activity of an enzyme per milligram of total protein (expressed in µmol min$^{-1}$ mg$^{-1}$). It is the amount of product formed by an enzyme in a given amount of time under given conditions per milligram of total protein. Specific activity is equal to the rate of reaction multiplied by the volume of reaction divided by the mass of total protein. The SI unit is katal kg$^{-1}$, but a more practical unit is µmol min$^{-1}$ mg$^{-1}$. Specific activity is a measure of enzyme processivity, at a specific (usually saturating) substrate concentration, and is usually constant for a pure enzyme. If the molecular weight of the enzyme is known, the turnover number, or µmol product sec$^{-1}$ µmol$^{-1}$ of active enzyme, can be calculated from the specific activity. The turnover number can be visualized as the number of times each enzyme molecule carries out its catalytic cycle per second.

The activity may be determined in an enzyme assay measuring either the consumption of substrate or production of product over time. A large number of different methods of measuring the concentrations of substrates and products exist and many enzymes can be assayed in several different ways as known to the person skilled in the art. In the present invention, the transaminase in question is incubated with as suitable amine donor and a suitable amine acceptor under conditions and for a time conducive to the transamination.

Enzyme assays can be split into two groups according to their sampling method: continuous assays, where the assay gives a continuous reading of activity, and discontinuous assays, where samples are taken, the reaction stopped and then the concentration of substrates/products determined.

In a preferred embodiment, the transaminase of the present invention is stereoselective, such as (S)-selective or (R)-selective, particularly (S)-selective. "Stereoselectivity" refers to the preferential formation in a chemical or enzymatic reaction of one stereoisomer over another. Stereoselectivity can be partial, where the formation of one stereoisomer is favored over the other, or it may be complete where only one stereoisomer is formed. When the stereoisomers are enantiomers, the stereoselectivity is referred to as enantioselectivity. It is commonly reported in the art (typically as a percentage) as the enantiomeric excess (e.e.) calculated therefrom according to the formula [major enantiomer−minor enantiomer]/[major enantiomer+minor enantiomer]. Alternatively, the enantiomeric ratio or er (S:R) may be used to characterize stereoselectivity. The enantiomeric ratio is the ratio of the percent of one enantiomer (e.g. the (S)-enantiomer) in a mixture of enantiomers to that of the other enantiomer (e.g. the (R)-enantiomer). Where the stereoisomers are diastereoisomers, the stereoselectivity is referred to as diastereoselectivity, the fraction (typically reported as a percentage) of one diastereomer in a mixture of two diastereomers, commonly alternatively reported as the diastereomeric excess (d.e.). Enantiomeric excess and diastereomeric excess are types of stereomeric excess.

Enantiomerically enriched in this context stands for an enantiomeric ratio of the desired chiral amine relative to the undesired chiral amine of more than 50:50, preferably at least 70:30, even more preferably at least 95:5, most preferably at least 99.5:0.5 or likewise for an enantiomeric excess greater than 0%, preferably at least 40%, even more preferably at least 90%, most preferably of at least 99%.

Surprisingly, it was found that the mutations as defined herein in the context of the present invention, which are introduced in wild-type transaminases, increase the transaminase activity of the enzyme relative to the wild-type enzyme. As detailed herein, this is of particular interest for the production of amines, particularly for the production of enantiomerically enriched chiral amines either by method
a) a kinetic resolution of a racemic amine in the presence of an amine acceptor and a mutant transaminase or the fusion protein
or by method
b) an asymmetric transamination of a prochiral ketone in the presence of an amine donor and a mutant transaminase or the fusion protein,
wherein the mutant transaminase or the fusion protein is stereoselective.

Particularly, the activity for selected compounds, e.g. bulky substrates, which increases the spectrum of substrates accepted by the transaminase, and/or the amine donor isopropylamine is increased. This is important in the present invention, as it allows for broader industrial applicability especially in the transaminase-mediated production of amines such as chiral amines.

It was found that the transaminase showed increased activity, particularly on bulky substrates. Illustrative examples for bulky (racemic) amines according to method a) are shown in Scheme 2 below.

Scheme 2:

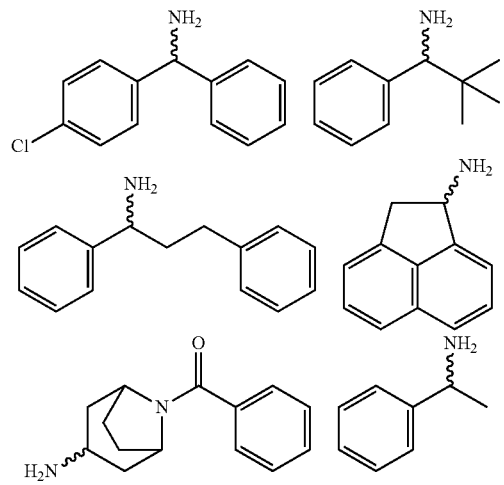

Their chemical names are 1-(4-chlorophenyl)-1-phenyl-1-aminomethane (1a), 2,2-dimethyl-1-phenyl-1-amino propane (2a), 1,3-diphenyl-1-aminopropane (3a), 1,2-dihydroacenaphthylen-1-amine (4a), 3-amino-8-benzoyl-8-azabicyclo[3.2.1]octane (5a) and 1-phenylethylamine (6a).

Illustrative examples for bulky prochiral ketones according to method b) are shown in Scheme 3 below.

Scheme 3:

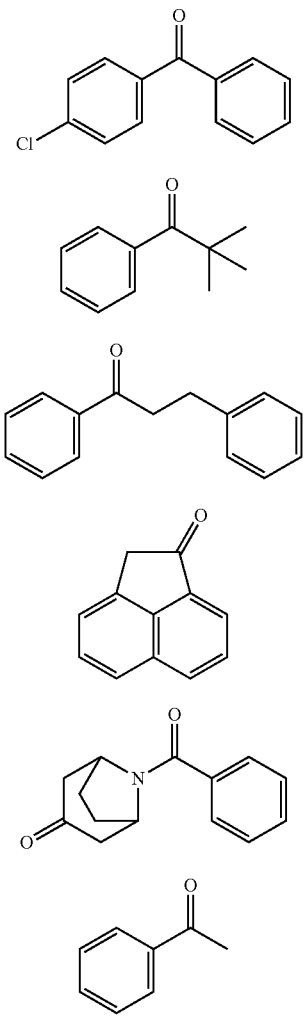

Their chemical names are (4-chlorophenyl)-phenyl-methanone (1 b), 2,2-dimethyl-1-phenyl-propan-1-one (2b) 1,3-diphenylpropan-1-one (3b), 2H-acenaphthylen-1-one (4b), 8-benzoyl-8-azabicyclo[3.2.1]octan-3-one (5b) and 1-phenylethanone (6b).

There are various methods of determining enzyme activity well-known in the art. These include without limitation spectrometric assays, fluorometric assays, calorimetric assays, chemiluminescence assays, assays involving light scattering, radiometric assays, and chromatographic assays. Assays are usually performed under well controlled conditions including e.g. pH value, temperature, salt, buffers, and substrate concentration. Suitable tests for studying transaminase activity of an enzyme are well-known to the skilled person. A suitable test is described by Schätzle et al., in Analytical Chemistry (2009). This direct photometric assay is based on the significant difference in the absorption spectrum of the amine and its corresponding ketone. In general, the absorption spectrum of the conjugated aromatic ketones is distinct due to the electron delocalization of their benzoyl moiety, which is not existent in the corresponding amines. This difference is mirrored in a difference in the absorption spectrum, and the production of ketone can be monitored at the wavelength of the highest absorption difference between the ketone and the amine, which can be easily determined from someone trained in the art. This assay is particularly suitable for substrates 1, 2, 3, 4 and 6 [i.e. amines 1a, 2a, 3a, 4a and 6a (see Scheme 2) or ketones 1 b, 2b, 3b, 4b and 6b (see Scheme 3)]. For substrates, for which the aforementioned assay may not be suitable, like substrate 5a/b or iso-propylamine, a suitable test was developed in order to screen amine donors; its principle was described by Weiß et al. in Analytical Chemistry (2014). In this test, glyoxylate is used as amine acceptor. The transaminase uses a desired amine donor to produce glycine by the amination of glyoxylate, and the glycine is subsequently oxidized by a glycine oxidase, producing also hydrogen peroxide. The hydrogen peroxide is used by horseradish peroxidase to oxidize phenol to 1,4-benzoquinone, which spontaneously reacts with 4-aminoantipyrine with a condensation reaction to form the quinone imine dye, which is detectable in visible wavelength (498 nm). The phenol can be substituted by vanillic acid, which undergoes an oxidative decarboxylation and oxidation mediated by the horseradish peroxidase to 2-methoxy-1,4-benzoquinone. Apart from these two tests, standard chromatographic methods known to the person trained in the field, such as high performance liquid chromatography (HPLC), gas chromatography (GC), supercritical fluid chromatography (SFC) and capillary electrophoresis were also used.

Furthermore, an exemplary test is also described in the Examples (see section B2) and particularly suitable substrates are substrates 1 to 5 [as amines 1a to 5a (see Scheme 2) or ketones 1 b to 5b (see Scheme 3)] or the amine donor iso-propylamine (2-propylamine).

Moreover, the person skilled in the art knows statistical procedures to assess whether or not one value is increased relative to another such as Student's t-test or chi-square test. It is evident for the skilled person that any background signal has to be subtracted when analyzing the data. In specific embodiments, the increase in enzyme activity is at least about 10%. In other embodiments, the increase is at least 20%, 30%, 40%, 50% or 100%, especially 150%, 200%, 250%, or 300%. Percentage increase in activity may be determined as [activity (mutant)/activity (wild-type)−1]* 100.

In accordance with the present invention the mutant transaminase comprises an amino acid sequence that is at least 65% identical to the amino acid sequence of SEQ ID NO: 1.

The term "SEQ ID NO: 1" as referred to herein denotes the amino acid sequence as shown in SEQ ID NO: 1 and represents the amino acid sequence of a wild-type aminotransferase from *Ruegeria* sp. TM1040 (referred to as 3FCR). In particular, the term "SEQ ID NO.: 1" refers to the amino acid sequence as set forth below: (please note that preferred substitution sites according to the present invention are indicated by bold/underline and specified by position numbers):

```
                                           (SEQ ID NO: 1)
         10         20         30         40
MLKNDQLDQW DRDNFFHPST HLAQHARGES ANRVIKTASG
```

-continued

```
         50         60         70         80
VFIEDRDGTK LLDAFAGLYC VNVGYGRQEI AEAIADQARE
                   59

90        100        110        120
LAYYHSYVGH GTEASITLAK MILDRAPKNM SKVYFGLGGS
       87

130        140        150        160
DANETNVKLI WYYNNILGRP EKKKIISRWR GYHGSGLVTG
                                152

170        180        190        200
SLTGLELFHK KFDLPVEQVI HTEAPYYFRR EDLNQTEEQF 210        220        230        240
VAHCVAELEA LIEREGADTI AAFIGEPILG TGGIVPPPAG
                                231  234

250        260        270        280
YWEAIQTVLN KHDILLVADE VVTGFGRLGT MFGSDHYGLE 290        300        310        320
PDIITIAKGL TSAYAPLSGS IVSDKVWKVL EQGTDENGPI 330        340        350        360
GHGWTYSAHP IGAAAGVANL KLLDELNLVS NAGEVGAYLN 370        380        390        400
ATMAEALSQH ANVGDVRGEG LLCAVEFVKD RDSRTFFDAA 410        420        430        440
DKIGPQISAK LLEQDKIIAR AMPQGDILGF APPFCLTRAE
                               423

450
ADQVVEGTLR AVKAVLG
```

The term "at least 65% identical" or "at least 65% sequence identity" as used herein means that the sequence of the mutant transaminase according to the present invention has an amino acid sequence characterized in that, within a stretch of 100 amino acids, at least 65 amino acids residues are identical to the sequence of the corresponding wild-type sequence. Sequence identity according to the present invention can, e.g., be determined by methods of sequence alignment in form of sequence comparison. Methods of sequence alignment are well known in the art and include various programs and alignment algorithms which have been described in, e.g., Pearson and Lipman (1988). Moreover, the NCBI Basic Local Alignment Search Tool (BLAST) is available from several sources, including the National Center for Biotechnology Information (NCBI, Bethesda, Md.) and on the internet, for use in connection with the sequence analysis programs blastp, blastn, blastx, tblastn and tblastx. Percentage of identity of mutants according to the present invention relative to the amino acid sequence of SEQ ID NO: 1 is typically characterized using the NCBI Blast blastp with standard settings. Alternatively, sequence identity may be determined using the software GENEious with standard settings. In the present invention, alignment results presented are derived from the Software Geneious (version R8), using the global alignment protocol with free end gaps as alignment type, and Blosum62 as a cost matrix. Identity of wild-type proteins towards to the SEQ ID NO: 1 (3FCR), without tags included have been determined for 3GJU as 71.3%, for ATA-3 as 72.2%, ATA-4 as 70.7%, for ATA-5 as 69.6%, for ATA-6 as 71.8%, for ATA-7 as 77.9%, for ATA-8 as 90.8%, and for ATA-9 as 80.3%.

In accordance with the present invention, the mutant transaminase has at least two amino acid substitutions relative to the wild-type transaminase, wherein the amino acid at the position corresponding to position 59 of SEQ ID NO: 1 is substituted with Trp or Phe (Trp59 or Phe59, respectively) and the amino acid at the position corresponding to position 231 of SEQ ID NO: 1 is substituted with Ala or Gly (Ala231 or Gly231, respectively).

In a preferred embodiment, the mutant transaminase of the present invention has one or more further mutations, namely:
the amino acid at the position corresponding to position 87 of SEQ ID NO: 1 is substituted with a hydrophobic amino acid (HYaa87), particularly wherein the hydrophobic amino acid is Leu (Leu87) or Val (Val87) or Phe (Phe87); and/or
the amino acid at the position corresponding to position 152 of SEQ ID NO: 1 is substituted with Phe (Phe152), and/or
the amino acid at the position corresponding to position 234 of SEQ ID NO: 1 is substituted with Phe (Phe234) or Met (M234), and/or
the amino acid at the position corresponding to position 423 of SEQ ID NO: 1 is substituted with His (His423).

Figure 4:
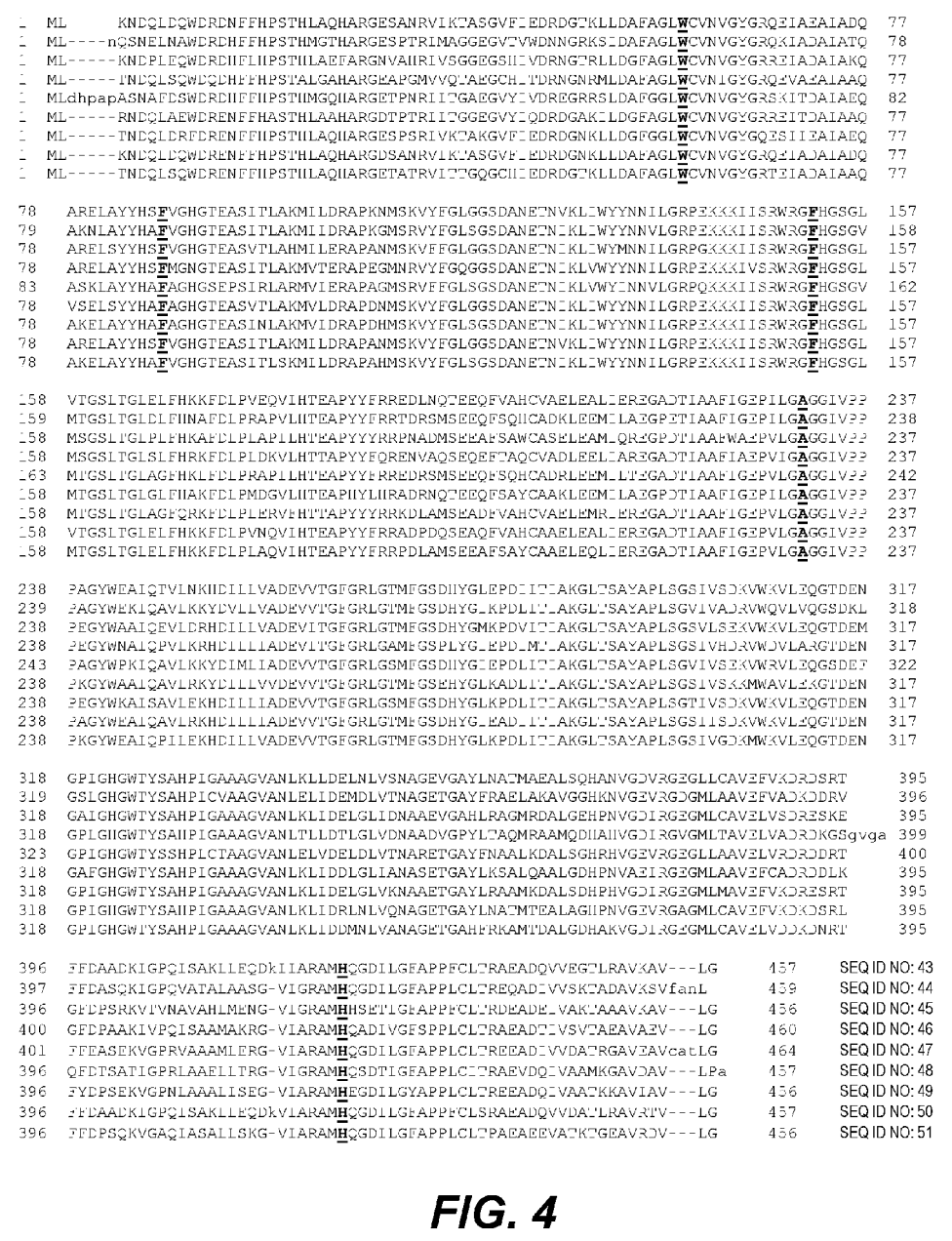

Positions of mutations are identified in the present invention with reference to SEQ ID NO: 1, i.e. the amino acid sequence of *Ruegeria* sp. TM1040 transaminase (referred to as 3FCR). The corresponding mutation sites of transaminases other than 3FCR can be identified by performing an amino acid alignment as detailed above (e.g. by using BLAST; Basic Local Alignment Search Tool available at http://blast.ncbi.nlm.nih.gov/Blast.cgi?PROGRAM=blastp&PAGE_TYPE=BlastSearch&LINK_LOC=blasthome with standard settings) or by comparison of the structures, if available, and identifying the corresponding amino acid. Examples of corresponding positions are indicated in FIGS. 2 to 4 and in the following Table:

| Transaminase | Position | | | | | |
|---|---|---|---|---|---|---|
| 3FCR | 59 | 87 | 152 | 231 | 234 | 423 |
| 3GJU | 60 | 88 | 153 | 232 | 235 | 423 |
| ATA-3 | 59 | 87 | 152 | 231 | 234 | 422 |
| ATA-4 | 59 | 87 | 152 | 231 | 234 | 426 |
| ATA-5 | 64 | 92 | 157 | 236 | 239 | 427 |
| ATA-6 | 59 | 87 | 152 | 231 | 234 | 422 |
| ATA-7 | 59 | 87 | 152 | 231 | 234 | 422 |
| ATA-8 | 59 | 87 | 152 | 231 | 234 | 423 |
| ATA-9 | 59 | 87 | 152 | 231 | 234 | 422 |

In one embodiment of the present invention, the mutant transaminase according to the present invention may comprise one or more amino acid deletion(s), particularly small (e.g. up to 10 amino acids) N- and/or C-terminal deletions.

In one embodiment, the sequence of the mutant transaminase according to the present invention may comprise, in addition to the substitutions specified herein one or more additional amino acid substitution(s), particularly one or more conservative amino acid substitutions. "Conservative amino acid substitution" refers to a substitution of a residue with a different residue having a similar side chain, and thus typically involves substitution of the amino acid in the polypeptide with amino acids within the same or similar defined class of amino acids. By way of example and not limitation, an amino acid with an aliphatic side chain may be substituted with another aliphatic amino acid, e.g., alanine, valine, leucine, and isoleucine; an amino acid with hydroxyl side chain is substituted with another amino acid with a hydroxyl side chain, e.g., serine and threonine; an amino acid having aromatic side chains is substituted with another amino acid having an aromatic side chain, e.g., phenylalanine, tyrosine, tryptophan, and histidine; an amino acid with a basic side chain is substituted with another amino acid with a basic side chain, e.g., lysine and arginine; an amino acid with an acidic side chain is substituted with another amino acid with an acidic side chain, e.g., aspartic acid or glutamic acid; and a hydrophobic or hydrophilic amino acid is replaced with another hydrophobic or hydrophilic amino acid, respectively. Examples of conservative amino acid substitutions include those listed below:

| Original Residue | Conservative Substitutions |
| --- | --- |
| Ala, Leu, Val, Ile | Other aliphatic (Ala, Leu, Val, Ile) |
|  | Other non-polar (Ala, Leu, Val, Ile, Gly, Met) |
| Gly, Met | Other non-polar (Ala, Leu, Val, Ile, Gly, Met) |
| Asp, Glu | Other acidic (Asp, Glu) |
| Lys, Arg | Other basic (Lys, Arg) |
| Asn, Gln, Ser, Thr | Other polar (Asn, Gln, Ser, Thr) |
| His, Tyr, Trp, Phe | Other aromatic (His, Tyr, Trp, Phe) |
| Cys, Pro | None |

In one embodiment of the present invention, the mutant transaminase according to the present invention may comprise one or more amino acid addition(s), particularly small (e.g. up to 10 amino acids) internal amino acid additions.

In another embodiment, the sequence of the mutant transaminase according to the present invention may comprise, in addition to the substitutions specified herein a combination of one or more deletion(s), substitution(s) or addition(s) as defined above.

Yet, in another preferred embodiment, the mutant transaminase of the present invention has at least the mutations
  Trp59 and Ala231, or
  Trp59, Phe87 and Ala231; or
  Trp59, Leu87 and Ala231; or
  Trp59, Val87 and Ala231; or
  Trp59, Phe87, Ala231 and His423; or
  Trp59, Phe87, Phe152 and Ala231; or
  Trp59, Leu87, Phe152 and Ala231; or
  Trp59, Val87, Phe152 and Ala231; or
  Trp59, Phe87, Phe152, Ala231 and His423, or
  Trp59 and Gly231; or
  Trp59, Phe87 and Gly231; or
  Trp59, Leu87 and Gly231; or
  Trp59, Val87 and Gly231; or
  Trp59, Phe87, Phe152 and Gly231; or
  Trp59, Phe87, Phe152, Gly231 and His423; or
  Phe59, and Ala231; or
  Phe59, Phe87, and Gly231; or
  Trp59, Ala231 and Phe234; or
  Trp59, Ala231 and Met234; or
  Trp59, Phe87, Ala231 and Phe234; or
  Trp59, Leu87, Ala231 and Phe234; or
  Trp59, Val87, Ala231 and Phe234; or
  Trp59, Phe87, Phe152, Ala231 and Phe234; or
  Trp59, Phe87, Phe152, Ala231, Phe234 and His423, or
  Trp59, Gly231 and Phe234; or
  Trp59, Phe87, Gly231 and Phe234; or
  Trp59, Leu87, Gly231 and Phe234; or
  Trp59, Val87, Gly231 and Phe234; or
  Trp59, Phe87, Phe152, Gly231 and Phe234; or
  Trp59, Phe87, Phe152, Gly231, Phe234 and His423; or
  Phe59, Phe87, Gly231 and Phe234, or
  Trp59, Ala231 and Met234; or
  Trp59, Phe87, Ala231 and Met234; or
  Trp59, Leu87, Ala231 and Met234; or
  Trp59, Val87, Ala231 and Met234; or
  Trp59, Phe87, Phe152, Ala231 and Met234; or
  Trp59, Phe87, Phe152, Ala231, Met234 and His423, or
  Trp59, Gly231 and Met234; or
  Trp59, Phe87, Gly231 and Met234; or
  Trp59, Leu87, Gly231 and Met234; or
  Trp59, Val87, Gly231 and Met234; or
  Trp59, Phe87, Phe152, Gly231 and Met234; or
  Trp59, Phe87, Phe152, Gly231, Met234 and His423; or
  Phe59, Phe87, Gly231 and Met234.

More preferably, the mutant transaminase of the present invention differs from the corresponding wild-type transaminase only by the following mutations
  Trp59 and Ala231, or
  Trp59, Phe87 and Ala231; or
  Trp59, Leu87 and Ala231; or
  Trp59, Val87 and Ala231; or
  Trp59, Phe87, Ala231 and His423; or
  Trp59, Phe87, Phe152 and Ala231; or
  Trp59, Leu87, Phe152 and Ala231; or
  Trp59, Val87, Phe152 and Ala231; or
  Trp59, Phe87, Phe152, Ala231 and His423, or
  Trp59 and Gly231; or
  Trp59, Phe87 and Gly231; or
  Trp59, Leu87 and Gly231; or
  Trp59, Val87 and Gly231; or
  Trp59, Phe87, Phe152 and Gly231; or
  Trp59, Phe87, Phe152, Gly231 and His423; or
  Phe59, and Ala231; or
  Phe59, Phe87, and Gly231; or
  Trp59, Ala231 and Phe234; or
  Trp59, Ala231 and Met234; or
  Trp59, Phe87, Ala231 and Phe234; or
  Trp59, Leu87, Ala231 and Phe234; or
  Trp59, Val87, Ala231 and Phe234; or
  Trp59, Phe87, Phe152, Ala231 and Phe234; or
  Trp59, Phe87, Phe152, Ala231, Phe234 and His423, or
  Trp59, Gly231 and Phe234; or
  Trp59, Phe87, Gly231 and Phe234; or
  Trp59, Leu87, Gly231 and Phe234; or
  Trp59, Val87, Gly231 and Phe234; or
  Trp59, Phe87, Phe152, Gly231 and Phe234; or
  Trp59, Phe87, Phe152, Gly231, Phe234 and His423; or
  Phe59, Phe87, Gly231 and Phe234, or
  Trp59, Ala231 and Met234; or
  Trp59, Phe87, Ala231 and Met234; or
  Trp59, Leu87, Ala231 and Met234; or
  Trp59, Val87, Ala231 and Met234; or
  Trp59, Phe87, Phe152, Ala231 and Met234; or
  Trp59, Phe87, Phe152, Ala231, Met234 and His423, or
  Trp59, Gly231 and Met234; or
  Trp59, Phe87, Gly231 and Met234; or
  Trp59, Leu87, Gly231 and Met234; or
  Trp59, Val87, Gly231 and Met234; or
  Trp59, Phe87, Phe152, Gly231 and Met234; or
  Trp59, Phe87, Phe152, Gly231, Met234 and His423; or
  Phe59, Phe87, Gly231 and Met234.

In an even more preferred embodiment, the mutant transaminase of the present invention has at least the mutations
  Trp59, Phe87, Phe152 and Ala231, or
  Trp59, Phe87, Phe152, Ala231 and Met234, or
  Trp59, Phe87, Phe152, Ala231 and H423, or
  Phe59, Phe87 and Gly231.

More preferably, the mutant transaminase of the present invention differs from the corresponding wild-type transaminase only by the following mutations Trp59, Phe87, Phe152 and Ala231, or
Trp59, Phe87, Phe152, Ala231 and Met234, or
Trp59, Phe87, Phe152, Ala231 and H423, or
Phe59, Phe87 and Gly231.

Preferred and specific amino acid sequences of mutant transaminase are those comprising or consisting of the sequence as defined in any of SEQ ID NO: 30 to 38, 43 to 51, 53, 55 and 58-64 (see FIGS. 3, 4 and 5) and 57 (see below section "SEQUENCES").

As detailed above, the mutant transaminase of the present invention comprises an amino acid sequence that is at least 65% identical to the amino acid sequence of SEQ ID NO: 1. In a preferred embodiment, the mutant transaminase comprises an amino acid sequence that is at least 70%, 75%, 80%, 85%, 90%, 95%, 96%, 97%, 98% or 99% identical to the amino acid sequence of SEQ ID NO: 1. Sequence identity may be determined as described above. In a preferred embodiment of the present invention, the mutant transaminase comprises an amino acid sequence that is at least 90%, 95%, 96%, 97%, 98%, or 99% identical to the amino acid sequence selected from the group consisting of SEQ ID NOs: 1, 3 and 5 to 11.

In accordance with the present invention, the mutant transaminase has an increased transaminase activity relative to the corresponding wild type enzyme. As detailed above, this is of particular interest with bulky substrates as well as the amine donor iso-propylamine. Accordingly, increased activity for bulky substrates/iso-propylamine is preferred in the context of the present invention. Suitable bulky test substrates for determining whether activity for these is increased are substrates 1 to 5 include those shown in Scheme 2, namely 1-(4-chlorophenyl)-1-phenyl-1-aminomethane (1a), 2,2-dimethyl-1-phenyl-1-amino propane (2a), 1,3-diphenyl-1-aminopropane (3a), 1,2-dihydroacenaphthylen-1-amine (4a), and 3-amino-8-benzoyl-8-azabicyclo[3.2.1]octane (5a) as well as those shown in Scheme 3 (4-chlorophenyl)-phenyl-methanone (1b), 2,2-dimethyl-1-phenyl-propan-1-one (2b) 1,3-diphenylpropan-1-one (3b), 2H-acenaphthylen-1-one (4b), and 8-benzoyl-8-azabicyclo [3.2.1]octan-3-one (5b). The skilled person will understand that an increase in activity is already present if the activity with respect to at least one of substrate or iso-propylamine, particularly at least one of substrate 1 to 5 or iso-propylamine, is increased.

Accordingly, in a preferred embodiment of the present invention, the mutant transaminase has increased transaminase activity for transamination of at least one compound selected from the group consisting of (1-(4-chlorophenyl)-1-phenyl-1-aminomethane (1a), 2,2-dimethyl-1-phenyl-1-amino propane (2a), 1,3-diphenyl-1-aminopropane (3a), 1,2-dihydroacenaphthylen-1-amine (4a), and 3-amino-8-benzoyl-8-azabicyclo[3.2.1]octane (5a), 3(4-chlorophenyl)-phenyl-methanone (1 b), 2,2-dimethyl-1-phenyl-propan-1-one (2b) 1,3-diphenylpropan-1-one (3b), 2H-acenaphthylen-1-one (4b), 8-benzoyl-8-azabicyclo[3.2.1]octan-3-one (5b) and iso-propylamine.

In a preferred embodiment, the mutant transaminase has an at least 2-fold increased transaminase activity relative to the corresponding wild type enzyme, preferably an at least 2.5-fold increased transaminase activity, preferably an at least 3-fold increased transaminase activity, more preferably an at least 3.5-fold increased transaminase activity, and most preferably an at least 4-fold increased transaminase activity, particularly for at least one compound selected from the group consisting of 1-(4-chlorophenyl)-1-phenyl-1-aminomethane (1a), 2,2-dimethyl-1-phenyl-1-amino propane (2a), 1,3-diphenyl-1-aminopropane (3a), 1,2-dihydroacenaphthylen-1-amine (4a), and 3-amino-8-benzoyl-8-azabicyclo[3.2.1]octane (5a), 3(4-chlorophenyl)-phenyl-methanone (1 b), 2,2-dimethyl-1-phenyl-propan-1-one (2b) 1,3-diphenylpropan-1-one (3b), 2H-acenaphthylen-1-one (4b), 8-benzoyl-8-azabicyclo[3.2.1]octan-3-one (5b) and iso-propylamine.

In a further aspect, the present invention relates to a fusion protein comprising the transaminase of the present invention.

Fusion proteins are proteins created by joining of two or more originally separate proteins or peptides. This procedure results in a polypeptide with functional properties derived from each of the original proteins. Accordingly, depending on the intended use of the transaminase it may be combined with a further peptide or protein into a fusion protein. The proteins may be fused via a linker or spacer, which increases the likelihood that that the proteins fold independently and behave as expected. Especially in the case where the linkers enable protein purification, linkers in protein or peptide fusions are sometimes engineered with cleavage sites for proteases or chemical agents that enable the liberation of the two separate proteins. Di- or multimeric fusion proteins can be manufactured through genetic engineering by fusion to the original proteins of peptide domains that induce artificial protein di- or multimerization (e.g., streptavidin or leucine zippers). Fusion proteins can also be manufactured with toxins or antibodies attached to them. Other fusions include the addition the addition of signal sequences, such a lipidation signal, sequence, a secretion signal sequence, a glycosylation signal sequence, a translocation signal peptide etc.

Preferably, the fusion protein of the present invention comprises a tag. Tags are attached to proteins for various purposes, e.g. in order to ease purification, to assist in the proper folding in proteins, to prevent precipitation of the protein, to alter chromatographic properties, to modify the protein or to mark or label the protein.

A number of (affinity) tags or (affinity) markers are known at present. These are usually divided into 3 classes according to their size: small tags have a maximum of 12 amino acids, medium-sized ones have a maximum of 60 and large ones have more than 60. The small tags include the Arg-tag, the His-tag, the Strep-tag, the Flag-tag, the T7-tag, the V5-peptide-tag and the c-Myc-tag, the medium-sized ones include the S-tag, the HAT-tag, the calmodulin-binding peptide, the chitin-binding peptide and some cellulose-binding domains. The latter can contain up to 189 amino acids and are then regarded, like the GST- and MBP-tag, as large affinity tags. In order to produce especially pure proteins, so-called double tags or tandem tags were developed. In this case the proteins are purified in two separate chromatography steps, in each case utilizing the affinity of a first and then of a second tag. Examples of such double or tandem tags are the GST-His-tag (glutathione-S-transferase fused to a polyhistidine-tag), the 6×His-Strep-tag (6 histidine residues fused to a Strep-tag (see below)), the 6×His-tag100-tag (6 histidine residues fused to a 12-amino-acid protein of mammalian MAP-kinase 2), 8×His-HA-tag (8 histidine residues fused to a haemagglutinin-epitope-tag), His-MBP (His-tag fused to a maltose-binding protein, FLAG-HA-tag (FLAG-tag fused to a hemagglutinin-epitope-tag), and the FLAG-Strep-tag. Most of these tags have been specifically developed for the purification of proteins produced by prokaryotic cells. Suitable tags are given in the description and include the one SEQ ID NO: 56 (SHHHHHH).

In a further aspect, the present invention relates to a nucleic acid encoding the transaminase of the present invention.

The term "nucleic acid" as used herein generally relates to any nucleotide molecule which encodes the mutant transaminase of the invention and which may be of variable length. Examples of a nucleic acid of the invention include, but are not limited to, plasmids, vectors, or any kind of DNA and/or RNA fragment(s) which can be isolated by standard molecular biology procedures, including, e.g. ion-exchange chromatography. A nucleic acid of the invention may be used for transfection or transduction of a particular cell or organism.

Nucleic acid molecule of the present invention may be in the form of RNA, such as mRNA or cRNA, or in the form of DNA, including, for instance, cDNA and genomic DNA e.g. obtained by cloning or produced by chemical synthetic techniques or by a combination thereof. The DNA may be triple-stranded, double-stranded or single-stranded. Single-stranded DNA may be the coding strand, also known as the sense strand, or it may be the non-coding strand, also referred to as the anti-sense strand. Nucleic acid molecule as used herein also refers to, among other, single- and double-stranded DNA, DNA that is a mixture of single- and double-stranded RNA, and RNA that is a mixture of single- and double-stranded regions, hybrid molecules comprising DNA and RNA that may be single-stranded or, more typically, double-stranded, or triple-stranded, or a mixture of single- and double-stranded regions. In addition, nucleic acid molecule as used herein refers to triple-stranded regions comprising RNA or DNA or both RNA and DNA.

Additionally, the nucleic acid may contain one or more modified bases. Such nucleic acids may also contain modifications e.g. in the ribose-phosphate backbone to increase stability and half life of such molecules in physiological environments. Thus, DNAs or RNAs with backbones modified for stability or for other reasons are "nucleic acid molecule" as that feature is intended herein. Moreover, DNAs or RNAs comprising unusual bases, such as inosine, or modified bases, such as tritylated bases, to name just two examples, are nucleic acid molecule within the context of the present invention. It will be appreciated that a great variety of modifications have been made to DNA and RNA that serve many useful purposes known to those of skill in the art. The term nucleic acid molecule as it is employed herein embraces such chemically, enzymatically or metabolically modified forms of nucleic acid molecule, as well as the chemical forms of DNA and RNA characteristic of viruses and cells, including simple and complex cells, inter alia.

Furthermore, the nucleic acid molecule encoding the mutant transaminase of the invention can be functionally linked, using standard techniques such as standard cloning techniques, to any desired sequence, such as a regulatory sequence, leader sequence, heterologous marker sequence or a heterologous coding sequence to create a fusion protein.

The nucleic acid of the invention may be originally formed in vitro or in a cell in culture, in general, by the manipulation of nucleic acids by endonucleases and/or exonucleases and/or polymerases and/or ligases and/or recombinases or other methods known to the skilled practitioner to produce the nucleic acids.

The nucleic acid of the invention may be comprised in an expression vector, wherein the nucleic acid is operably linked to a promoter sequence capable of promoting the expression of the nucleic acid in a host cell.

As used herein, the term "expression vector" generally refers to any kind of nucleic acid molecule that can be used to express a protein of interest in a cell (see also above details on the nucleic acids of the present invention). In particular, the expression vector of the invention can be any plasmid or vector known to the person skilled in the art which is suitable for expressing a protein in a particular host cell including, but not limited to, mammalian cells, bacterial cell, and yeast cells. An expression construct of the present invention may also be a nucleic acid which encodes a transaminase of the invention, and which is used for subsequent cloning into a respective vector to ensure expression. Plasmids and vectors for protein expression are well known in the art, and can be commercially purchased from diverse suppliers including, e.g., Promega (Madison, Wis., USA), Qiagen (Hilden, Germany), Invitrogen (Carlsbad, Calif., USA), or MoBiTec (Germany). Methods of protein expression are well known to the person skilled in the art and are, e.g., described in Sambrook et al., 2000 (Molecular Cloning: A laboratory manual, Third Edition).

The vector may additionally include nucleic acid sequences that permit it to replicate in the host cell, such as an origin of replication, one or more therapeutic genes and/or selectable marker genes and other genetic elements known in the art such as regulatory elements directing transcription, translation and/or secretion of the encoded protein. The vector may be used to transduce, transform or infect a cell, thereby causing the cell to express nucleic acids and/or proteins other than those native to the cell. The vector optionally includes materials to aid in achieving entry of the nucleic acid into the cell, such as a viral particle, liposome, protein coating or the like. Numerous types of appropriate expression vectors are known in the art for protein expression, by standard molecular biology techniques. Such vectors are selected from among conventional vector types including insects, e.g., baculovirus expression, or yeast, fungal, bacterial or viral expression systems. Other appropriate expression vectors, of which numerous types are known in the art, can also be used for this purpose. Methods for obtaining such expression vectors are well-known (see, e.g. Sambrook et al, supra).

As detailed above, the nucleic acid which encodes a mutant transaminase of the invention is operably linked to sequence which is suitable for driving the expression of a protein in a host cell, in order to ensure expression of the protein. However, it is encompassed within the present invention that the claimed expression construct may represent an intermediate product, which is subsequently cloned into a suitable expression vector to ensure expression of the protein. The expression vector of the present invention may further comprise all kind of nucleic acid sequences, including, but not limited to, polyadenylation signals, splice donor and splice acceptor signals, intervening sequences, transcriptional enhancer sequences, translational enhancer sequences, drug resistance gene(s) or alike. Optionally, the drug resistance gene may be operably linked to an internal ribosome entry site (IRES), which might be either cell cycle-specific or cell cycle-independent.

The term "operably linked" as used herein generally means that the gene elements are arranged as such that they function in concert for their intended purposes, e.g. in that transcription is initiated by the promoter and proceeds through the DNA sequence encoding the protein of the present invention. That is, RNA polymerase transcribes the sequence encoding the fusion protein into mRNA, which in then spliced and translated into a protein.

The term "promoter sequence" as used in the context of the present invention generally refers to any kind of regulatory DNA sequence operably linked to a downstream coding sequence, wherein said promoter is capable of binding RNA polymerase and initiating transcription of the encoded open reading frame in a cell, thereby driving the expression of said downstream coding sequence. The promoter sequence of the present invention can be any kind of promoter sequence known to the person skilled in the art, including, but not limited to, constitutive promoters, inducible promoters, cell cycle-specific promoters, and cell type-specific promoters.

Another aspect of the present invention relates to a host cell comprising the transaminase of the present invention, the fusion protein of the present invention, or the polynucleotide or expression vector of the present invention. In one embodiment of the present invention, a host cell having transaminase activity is used in the context of the present invention. Particularly, a cell optionally lysed or otherwise permeabilized is used for transamination, e.g. in the methods and uses of the present invention. A "host cell" of the present invention can be any kind of organism suitable for application in recombinant DNA technology, and includes, but is not limited to, all sorts of bacterial and yeast strain which are suitable for expressing one or more recombinant protein(s). Examples of host cells include, for example, various *Bacillus subtilis* or *E. coli* strains. A variety of *E. coli* bacterial host cells are known to a person skilled in the art and include, but are not limited to, strains such as DH5-alpha, HB101, MV1190, JM109, JM101, or XL-1 blue which can be commercially purchased from diverse suppliers including, e.g., Stratagene (CA, USA), Promega (WI, USA) or Qiagen (Hilden, Germany). A particularly suitable host cell is also described in the Examples, namely *E. coli* BL21 (DE3) cells. *Bacillus subtilis* strains which can be used as a host cell include, e.g., 1012 wild type: leuA8 metB5 trpC2 hsdRM1 and 168 Marburg: trpC2 (Trp-), which are, e.g., commercially available from MoBiTec (Germany).

The cultivation of host cells according to the invention is a routine procedure known to the skilled person. That is, a nucleic acid encoding a mutant transaminase of the invention can be introduced into a suitable host cell(s) to produce the respective protein by recombinant means. These host cells can by any kind of suitable cells, preferably bacterial cells such as *E. coli*, which can be cultivated in culture. At a first step, this approach may include the cloning of the respective gene into a suitable plasmid vector. Plasmid vectors are widely used for gene cloning, and can be easily introduced, i.e. transfected, into bacterial cells which have been made transiently permeable to DNA. After the protein has been expressed in the respective host cell, the cells can be harvested and serve as the starting material for the preparation of a cell extract containing the protein of interest. A cell extract containing the protein of interest is obtained by lysis of the cells. Methods of preparing a cell extract by means of either chemical or mechanical cell lysis are well known to the person skilled in the art, and include, but are not limited to, e.g. hypotonic salt treatment, homogenization, or ultrasonification.

In a further aspect, the present invention provides a method of producing an amine comprising reacting an amine acceptor with the mutant transaminase of the present invention or the fusion protein of the present invention in the presence of an amine donor.

The reaction of the present invention follows in principle the scheme presented in Scheme 1 (see above). The scheme illustrates that an amino group is transferred from the amine donor to the amine acceptor. The amine donor may be any molecule comprising a transferable amino group which is accepted by the mutant transaminase or fusion protein of the present invention. The amine acceptor may be any molecule to which the amino group may be transferred by the mutant transaminase or fusion protein of the present invention. In general, the amino group ($NH_2$) will be transferred by the transaminase from a primary amine (amine donor) to a carbonyl group (C=O) (amine acceptor). The terms "amine acceptor" and "amino acceptor" on the one hand as well as "amine donor" and "amino donor" on the other hand are used interchangeably.

In a preferred embodiment an enantiomerically enriched chiral amine is produced and
the method is either
a) a kinetic resolution of a racemic amine in the presence of an amine acceptor and a mutant transaminase or the fusion protein or
b) an asymmetric transamination of a prochiral ketone in the presence of an amine donor and a mutant transaminase or the fusion protein,
wherein the mutant transaminase or the fusion protein is stereoselective.

It is hereby understood that the mutant transaminase or fusion protein might be applied as solution, lyophilisate, immobilized or whole cell catalyst.

Method a)

In this method, referred to as kinetic resolution, the enantiomers of the racemic amine react with different reaction rates with the stereoselective transaminase or fusion protein (optionally in a host cell), resulting in an enantiomerically enriched composition of the less reactive enantiomer. Accordingly, the racemic mixture of amines is enantiomerically enriched for the desired enantiomer.

The racemic amine may have the formula

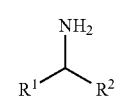

I wherein
$R^1$ or $R^2$ independently of each other represent optionally substituted alkyl, aryl carbocyclyl or heterocyclyl; or
$R^1$ and $R^2$ together with the carbon atom they are attached to form an optionally substituted mono- or poly-cyclic carbocyclic or heterocyclic ring.

In a preferred embodiment
$R^1$ is optionally substituted $C_{1-12}$-alkyl or aryl;
$R^2$ is optionally substituted aryl or heterocyclyl; or
$R^1$ and $R^2$ together with the carbon atom they are attached to form an optionally substituted mono- or poly-cyclic carbocyclic or heterocyclic ring, wherein optional substituents are selected from $C_{1-12}$-alkyl, $C_{1-12}$-alkoxy, aryl, aryloxy, halogen, hydroxyl or cyano.

In a further preferred embodiment
$R^1$ is optionally substituted $C_{1-7}$-alkyl or phenyl;
$R^2$ is optionally substituted phenyl; or
$R^1$ and $R^2$ together with the carbon atom they are attached to form an optionally substituted mono- or poly-cyclic carbocyclic or heterocyclic ring, wherein optional substituents are selected from $C_{1-7}$-alkyl, $C_{1-7}$-alkoxy, phenyl, phenyloxy, chlorine hydroxyl or cyano.

Illustrative examples of amines are shown in Scheme 2 (above).

Suitable amine acceptors for the kinetic resolution in method a) can be selected from ketones and keto carboxylic acids. Preferably, keto carboxylic acids such as the 2-keto carboxylic acids like 2-ketoglutaric acid, glyoxylic acid, pyruvic acid, oxaloacetic acid, and the like, as well as suitable salts thereof are used. Mostly used and therefore most preferred are the conjugate bases of the 2-keto carboxylic acids such as 2-ketoglutarate, pyruvate, glyoxylate or oxaloate.

The kinetic resolution of the racemic amine with the mutant transaminase or fusion protein is expediently effected in an aqueous medium, suitably containing a physiological buffer such as the CHES buffer at a pH in the range from 5 to 11, in particular from 7.5 to 10 in a temperature range from 10° to 50° C., preferably from 20° C. to 40° C.

The molar ratio of racemic amine to amine acceptor is, as a rule, selected in a molar ratio from 1.1 to 10, in particular from 1.1 to 2.5, when a 2-keto carboxylic acid is used as amine acceptor. When using ketones as amine acceptors the molar ratio can be significantly increased.

Method b)

Method b requires an asymmetric transamination of a prochiral ketone in the presence of an amine donor and a stereoselective mutant transaminase or the fusion protein (optionally in a host cell).

The prochiral ketone may have the formula

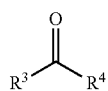

II $R^3$ or $R^4$ independently of each other represent optionally substituted alkyl, aryl, carbocyclyl or heterocyclyl; or
$R^3$ and $R^4$ together with the carbon atom they are attached to form an optionally substituted mono- or poly-cyclic carbocyclic or heterocyclic ring.

In a preferred embodiment
$R^3$ is optionally substituted $C_{1-12}$-alkyl or aryl;
$R^4$ is optionally substituted aryl or heterocyclyl; or
$R^3$ and $R^4$ together with the carbon atom they are attached to form an optionally substituted mono- or poly-cyclic carbocyclic or heterocyclic ring, wherein optional substituents are selected from $C_{1-12}$-alkyl, $C_{1-12}$-alkoxy, aryl, aryloxy, halogen, hydroxyl or cyano.

In a further preferred embodiment
$R^3$ is optionally substituted $C_{1-7}$-alkyl or phenyl;
$R^4$ is optionally substituted phenyl; or
$R^3$ and $R^4$ together with the carbon atom they are attached to form an optionally substituted mono- or poly-cyclic carbocyclic or heterocyclic ring, wherein optional substituents are selected from $C_{1-7}$-alkyl, $C_{1-7}$-alkoxy, phenyl, phenyloxy, chlorine hydroxyl or cyano.

Illustrative examples for prochiral ketones are shown in Scheme 3 (above).

Suitable amine donors may in general be selected from achiral or chiral amines or amino acids. Typical amines are primary aliphatic amines such as iso-propylamine, 1-phenylethylamine, 2-amino-4-phenylbutane, o-xylylene diamine or amino acids such as the alpha amino acids glycine, glutamic acid or alanine. Preferred amine donors are iso-propylamine and L-alanine.

In a preferred embodiment of the present invention, the amine acceptor and the amine donor are reacted with the mutant transaminase or fusion protein using a system that favors the equilibrium towards the desired enantiomerically enriched chiral amine.

Various biocatalytic strategies were employed to shift the equilibrium of the asymmetric transamination by removing the formed co-product, e.g. pyruvate, by a second enzyme, e.g., lactate dehydrogenase, pyruvate decarboxylase, or recycling/removing via alanine dehydrogenase.

As multi enzymes systems are applied, the reaction conditions need to satisfy the requirements of all the involved enzymes. Expediently the reaction takes place in an aqueous medium, suitably containing a physiological buffer such as the CHES buffer at a pH in the range from 5 to 11, in particular from 7.5 to 10 in a temperature range from 10° to 50° C., preferably from 20° C. to 40° C.

The molar ratio of the prochiral ketone and the amine donor is dependent on the second enzyme used and the individual reaction conditions. As a rule the molar ratio prochiral ketone and the amine donor can be selected in a range from 1:100 to 1:5, in particular from 1:50 to 1:10.

Applying a large excess of iso-propylamine as the preferred amine donor shifts the equilibrium in the asymmetric transamination to the formation of the target amine especially in combination with in-situ removal of the formed acetone, its corresponding ketone. The addition of organic co-solvents, water miscible and immiscible, or other specific additives might improve the reaction.

The terms as used herein for the racemic amine of formula I and for the prochiral ketone of formula II have the following meaning.

The term "halogen" denotes fluoro, chloro, bromo, or iodo, particularly chlorine.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, iso-propyl, n-butyl, iso-butyl, sec-butyl, or tert-butyl.

The term "alkoxy" refers to an alkyl group as defined above which is attached to an oxygen radical. Examples of alkoxy include methoxy, ethoxy, iso-propoxy, n-butoxy, iso-butoxy, sec-butoxy, or tert-butoxy.

The term "aryl" denotes a monovalent aromatic carbocyclic mono- or bicyclic ring system comprising 6 to 10 carbon ring atoms. Examples of aryl moieties include phenyl and naphthyl.

The term "aryloxy" denotes an aryl group as defined above which is attached to an oxygen radical. A suitable example is phenoxy or naphthyloxy.

The term "mono- or poly-cyclic ring" refers to a compound featuring one or more closed rings of atoms, primarily carbon. These ring substructures include cycloalkanes, aromatics, and other ring types. Though "poly" literally means "many", it also includes bicyclic, tricyclic, tetracyclic, etc.

The term "carbocyclic" refers to a saturated, partially unsaturated or unsaturated cyclic compound in which all of the ring members are carbon atoms, such as cyclohexane, decaline or 1,2-dihydronaphthalene. The compound may be aromatic or non-aromatic. Simple aromatic rings consist only of a conjugated planar ring system. Typical simple aromatic compounds are benzene, indole, and cyclotetradecaheptaene. Polycyclic aromatic hydrocarbons contain only carbon and hydrogen and are composed of multiple aromatic rings. Examples include naphthalene, anthracene and phenanthrene.

The term "heterocyclyl" refers to a saturated, partially unsaturated or unsaturated 5 to 6 membered monocyclic ring or 8 to 10 membered bicyclic ring which can comprise 1, 2 or 3 heteroatoms selected from nitrogen, oxygen and/or sulphur. The ring system may be aromatic or non-aromatic. Typical heterocyclyl residues are pyridinyl, piperidinyl, pyrrolidyl, pyrimidinyl, furanyl, pyranyl, benzoimidazolyl, quinolinyl or isoquinolinyl.

Optional substituents as used herein for the racemic amine of formula I and for the prochiral ketone of formula II can be selected from alkyl, alkoxy, aryl, aryloxy, halogen, hydroxyl or cyano. The preferences and examples as outlined above apply for the substituents as well.

In another aspect the present invention relates to the use of a mutant transaminase of to the present invention or the fusion protein of the present invention for the transamination of a ketone, particularly for the synthesis of a chiral amine having an asymmetric carbon atom bound to the transferred amino group.

With respect to the use of the present invention it is referred to the terms, examples and specific embodiments used in the context of the other aspects of the present disclosure, which are also applicable to this aspect. Particularly, the mutant transaminase or fusion protein according to the present invention may be used as detailed with respect to the methods of the present invention.

Unless defined otherwise, all technical and scientific terms and any acronyms used herein have the same meanings as commonly understood by one of ordinary skill in the art in the field of the invention. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The invention is not limited to the particular methodology, protocols, and reagents described herein because they may vary. Although any methods and materials similar or equivalent to those described herein can be used in the practice of the present invention, the preferred methods, and materials are described herein. Further, the terminology used herein is for the purpose of describing particular embodiments only and is not intended to limit the scope of the present invention.

As used herein and in the appended claims, the singular forms "a", "an", and "the" include plural reference unless the context clearly dictates otherwise. Similarly, the words "comprise", "contain" and "encompass" are to be interpreted inclusively rather than exclusively. Similarly, the word "or" is intended to include "and" unless the context clearly indicates otherwise. The term "plurality" refers to two or more.

The following Figures and Examples are intended to illustrate various embodiments of the invention. As such, the specific modifications discussed are not to be construed as limitations on the scope of the invention. It will be apparent to the person skilled in the art that various equivalents, changes, and modifications may be made without departing from the scope of the invention, and it is thus to be understood that such equivalent embodiments are to be included herein.

FIGURES

FIG. 1: Thermal stability of 3FCR variants at 25° C. in HEPES buffer (50 mM) pH 7.5; 3FCR Y59W/T231A (open circle), 3FCR Y59W/Y87F/T231A (filled circle), 3FCR Y59W/Y87F/Y152F/T231A (triangle), 3FCR Y59W/Y87F/Y152F/T231A/P423H (square). Activity was evaluated in kinetic resolution mode as described in paragraph B2, using 6a as amine donor, and the activity prior to the incubation was defined as 100%.

FIG. 2: Sequence alignment of preferred wild-type transaminases 3FCR, 3GJU, ATA-3, ATA-4, ATA5, ATA-6, ATA-7, ATA-8 and ATA-9. Sites for mutations Trp59, Phe87, Phe152, Ala231, Met234 and His423 according to the present invention are indicated in each transaminase by underline.

FIG. 3: Sequence alignment of preferred specific mutant transaminases 3FCR, 3GJU, ATA-3, ATA-4, ATA5, ATA-6, ATA-7, ATA-8 and ATA-9 (each having 4 amino acids substituted as indicated). Mutations Trp59 (Y59W), Phe87 (Y87F), Phe152 (Y152F) and Ala231 (T231A) according to the present invention are indicated in each transaminase by underline.

FIG. 4: Sequence alignment of preferred specific mutant transaminases 3FCR, 3GJU, ATA-3, ATA-4, ATA5, ATA-6, ATA-7, ATA-8 and ATA-9 (each having 5 amino acids substituted as indicated). Mutations Trp59 (Y59W), Phe87 (Y87F), Phe152 (Y152F), Ala231 (T231A) and His423 (P423H) according to the present invention are indicated in each transaminase by underline.

FIG. 5: Sequence alignment of preferred specific mutant transaminases 3FCR, 3GJU, ATA-3, ATA-4, ATA5, ATA-6, ATA-7, ATA-8 and ATA-9 (each having 5 amino acids substituted as indicated). Mutations Trp59 (Y59W), Phe87 (Y87F), Phe152 (Y152F), Ala231 (T231A) and Met234 (I234M) according to the present invention are indicated in each transaminase by underline.

EXAMPLES

General Procedures
A Biocatalyst Production
A1 Transaminase Gene Acquisition and Construction of Expression Vectors Transaminase (TA) open reading frames were designed and synthesized for expression in *Escherichia coli* (*E. coli*), based on the reported amino acid sequence of the transaminase (NCBI GI codes provided in Table 1), and the codon optimization algorithm of GenScript (Piscataway, U.S.A.), OptimumGene™. A C-terminal histidine tag, with a stop codon in the end was added in all cases, in order to facilitate the purification of the expressed TA, through a metal affinity chromatography (see respective paragraph). Restriction sites for the subsequent cloning in the vector of interest, pET22b, were added in the nucleotide sequence; NdeI restriction in the 5' end, and the BamHI restriction sequence in the 3' end. The starting codon (ATG) was incorporated in the restriction site of NdeI, so that there is only one methionine coded. The vector contains the bla coding sequence (beta-lactamase) for ampicillin resistance. According to the cloning strategy, the expression is under the control of a lac promoter. Resulting plasmids were transformed into *E. coli* BL21 (DE3) using standard methods. Sequences of the codon optimized genes and encoded polypeptides are provided in section "SEQUENCES".

The mutants used in the present invention were prepared with a modified version of the QuikChange® PCR method.

Primers were designed with mismatches that provide the desired mutations. For each reaction, we used Pfu buffer, 0.2 mM dNTPs, 0.2 ng/μL parental plasmid, 0.2 μM of each primer, 2% (w/w) DMSO and 0.2 μL of Pfu Plus! polymerase. The amplification was performed as follows:
a) 95° C., 5 min;
b) 20 cycles: 95° C., 45 sec; 60° C., 45 sec; 72° C., 7 min;
c) 72° C., 14 min The PCR product was digested by DpnI (20 μL/mL) for 2 h at 37° C. and then the restriction enzyme was deactivated by heating at 80° C. for 20 min. The digested PCR product was transformed into E. coli TOP-10 cells using standard methods. Plasmid isolation was performed from the clones transformed with the PCR product and the correct sequence was confirmed by DNA sequencing. The isolated plasmid with the correct mutations was transformed into E. coli BL21 (DE3) cells, using standard methods.

TABLE 1

Transaminases that were used in the present invention, and the NCBI gene identifier code (GI) of the wild type sequence.

| Name | Species | NCBI (GI) |
|---|---|---|
| 3FCR | Ruegeria sp. TM1040 | 499859271 |
| 3GJU | Mesorhizobium loti maff303099 | 499217058 |
| ATA-3 | Oceanicola granulosus | 494465841 |
| ATA-5 | Xanthobacteraceae | 517199618 |
| ATA-6 | Rhodobacteraceae bacterium RB2150_13166 | 126705951 |
| ATA-7 | Martelella mediterranea DSM 17316 | 516720233 |
| ATA-8 | Rugeria pomeroyi DSS-3 | 56677770 |
| ATA-9 | Sagittula stellata E-37 | 126711082 |

A2 Production of Transaminases

A single microbial colony of E. coli BL21 (DE3) was inoculated into 3 mL Luria Bertani medium in a testing tube, containing 100 μg/mL ampicillin, and was grown overnight (about 18 h) at 30° C. with shaking at 180 rpm. In a 300 mL shake flask, 30 mL of Terrific Broth containing 100 μg/mL ampicillin were inoculated with 1% (v/v) of the overnight culture (0.3 mL), and incubated at 37° C. with shaking at 180 rpm to an optical density at 600 nm ($OD_{600}$) of 0.5 to 0.7. The culture was cooled down to 20° C. and isopropyl β D-thiogalactoside (IPTG) was added at a final concentration of 0.2 mM to induce the expression of the TA. Incubation continued overnight at 20° C. with shaking, for about 16 h more. Cells were harvested via centrifugation (6000 g, 10 min, 4° C.) and the supernatant was discarded. The cell pellet was resuspended in 6 mL pre-cooled (4° C.) HEPES buffer (50 mM, pH 7.5), containing 0.1 mM pyridoxal-5-phosphate (PLP), and was treated with sonication (Bandelin Sonopuls HD2070; 2 times of 5 min with 5 min interval, 50% pulse, 60% power, kept always on ice) in order to lyse the cells. Cell debris was removed by centrifugation (6000 g, 30 min, 4° C.). The lysate supernatant was filtered with 0.2 μm filters (Millipore) and was stored at +4° C., or at −20° C., with the addition of 30% glycerol. In the case of a subsequent purification step, 0.3 M NaCl are included in the lysis buffer.

A3 Purification of Transaminases

Protein purification was performed using metal affinity chromatography, taking advantage of the C-terminal HisTag in all expressed TAs, with standard procedure for a person trained in the field. The crude lysate prepared as described in paragraph A2 is loaded to a HisTrap FastFlow 5 mL column equipped on an Äkta protein chromatography system, after equilibration with the lysis buffer (HEPES buffer, 50 mM, 0.3 M NaCl, 0.1 mM PLP). Once the column was loaded with the TA, it was washed from the non-specifically bound proteins with application of 2 column volumes of 10 mM imidazole. The TA was eluted from the column by the application of 2 column volumes of 0.3 M imidazole. The purified TA fractions were pooled and subsequently desalted via the Äkta system, using a Sephadex G60 column equilibrated with a HEPES (50 mM, pH 7.5) buffer, containing 0.1 mM PLP, with a standard procedure known to the person trained in the field. The purified enzyme solutions are stored at +4° C., or at −20° C., with the addition of 30% glycerol.

B Biocatalysis

B1 Preparation of Stock Solutions of the Compounds of Interest

Due to the hydrophobicity of the substrates of interest (cf. Schemes 2 and 3), stock solutions were prepared in water-soluble organic solvents, such as 2-propanol or dimethylsulfoxide. In a standard procedure for the kinetic resolution experiments, 20 to 40 mM stock solutions of the ketones and amines of interest were prepared in 2-propanol. As amine 1 and 4 were prepared as HCl-salts, the solution was sonicated for 30 sec at room temperature (Bandeling Sonorex RK 512H) to facilitate the dispersion. After dispersion, the homogeneous solution was stable and no precipitation of the amine or the amine salt was observed.

B2 Activity Measurement in Kinetic Resolution Mode

The activity measurements were performed in a TECAN Infinite® 200 PRO reader, using the microtiter plate reader. For the direct photometric assay described by Schätzle et al. in Analytical Chemistry (2009; see also above), the enzymatic reaction takes place in CHES buffer (50 mM, pH 9.0) at 30° C., in a total volume of 200 μL. 1 mM of racemic amine (rac-amine) of interest and 2 mM of amine acceptor (preferably pyruvate or glyoxylate) are added to the buffer (final concentrations), which contains the TA of interest. Due to the preparation of the amine stock solution in organic solvent, the final concentration of the organic solvent (2-propanol or DMSO) is 5% (v/v). The reaction is initiated by the addition of the second substrate (pyruvate). The concentration of the enzyme was varying between 2 and 800 μg/mL final concentration, depending on the specific activity towards the substrates in examination. The production of the ketone is monitored in the optimum wavelength for each compound, as determined with a method known to the person trained in the art. The wavelength used for each substrate, as well as the apparent extinction coefficients that were used to determine the specific activity of the TAs, as determined on the exact reaction conditions, are presented in Table 2.

TABLE 2

Optimum wavelength (nm) and apparent extinction coefficient ($M^{-1}cm^{-1}$) for the ketones of interest. Ketone 5a is not included, as it cannot be monitored by the direct photometric assay. Apparent coefficient was calculated simulating the reaction conditions, as some of the amines had a minor, but not detrimental absorbance in the monitored wavelength.

| Substrate | Optimum wavelength | Apparent extinction coefficient |
|---|---|---|
| 1a | 265 nm | 16562 $M^{-1}cm^{-1}$ |
| 2a | 245 nm | 7953 $M^{-1}cm^{-1}$ |
| 3a | 245 nm | 9646 $M^{-1}cm^{-1}$ |
| 4a | 340 nm | 5714 $M^{-1}cm^{-1}$ |
| 6a | 245 nm | 6115 $M^{-1}cm^{-1}$ |

For the compounds for which the direct photometric assay cannot be applied, such as substrate 5a/b and iso-propylamine, the test described by Weiß et al. in Analytical Chemistry (2014) was used. To use this test, a master mix in CHES buffer (pH 9.0, 50 mM) was prepared containing 2 mM amine 5a or 50 mM iso-propylamine (amine donor), 2.4 mM glyoxylate (amine acceptor), 0.12 mg/mL glycine oxidase from *Geobacillus kaustophilus*, 5 U/mL horseradish peroxidase, 3.9 mM vanillic acid and 1.2 mM 4-aminoantipyrine. The reaction was initiated with the addition of 20 µL of enzyme solution, normalized to a concentration of 1 mg/mL, to 130 µL of the master mix, and it was performed at 37° C. for 1 h. The enzymatic activity was determined by the increase of absorbance at 498 nm (c=4654 $M^{-1}$ $cm^{-1}$) due to the formation of the quinone imine dye. As this test relies on the activity of three enzymes, the calculation of specific activities is not possible. Thus, the activity of the TAs is always presented as relative to the reference variant [activity (mutant)/activity (reference)*100)].

Example 1: Improvement of the TA Specific Activity for the Kinetic Resolution of Rac-Amines 1a, 3a and 4a by Incorporation of the Mutations The specific activity of the presented mutants was determined for the kinetic resolution of rac-amines 1a, 3a, 4a and 6a according to the test described in section B2 of the General Procedures, with purified TAs. The positions were identified in the 3FCR scaffold and then transferred into the 3GJU scaffold, for confirmation of their significance in the acceptance of the amines of interest. The identity of SEQ ID NO: 1 and SEQ ID NO: 3 is 71.3%.

TABLE 3

Specific activities (U/mg) for 3FCR and 3GJU mutants in kinetic resolution mode.

| TA | Substrate | | | |
|---|---|---|---|---|
| | 1a | 3a | 4a | 6a |
| 3FCR | n.a. | 0.001 | 0.014 | 0.01 |
| 3FCR Y59W | 0.002 | 0.50 | 0.27 | 0.50 |
| 3FCR T231A | n.a. | 0.02 | 0.07 | 0.16 |
| 3FCR Y59W/T231A | 0.005 | 0.92 | 0.08 | 0.83 |
| 3FCR Y59W/Y87F/Y152F/T231A/P423H | 0.62 | 8.9 | 1.38 | 1.4 |
| 3GJU | n.a. | 0.003 | n.d. | 0.003 |
| 3GJU Y59W | n.a. | 0.11 | n.d. | 0.018 |
| 3GJU T231A | n.a. | 0.01 | n.d. | 0.038 |
| 3GJU Y59W/T231A | 0.003 | 0.66 | 0.11 | 0.344 |
| 3GJU Y59W/Y87F/Y152F/T231A/P423H | 0.22 | 0.92 | 0.90 | 0.449 | n.a.: not active;
n.d.: not determined.

The superiority of the double mutant Y59W/T231A compared to the wild-type and the single mutants in 3FCR is proven, but also to an enzyme with only 71.3% sequence identity (3GJU). More than that, the cumulative beneficial effect of the other positions is exemplified by the mutant Y59W/Y87F/Y152F/T231A/P423H.

More specifically, the most interesting intermediate mutants that were created on the scaffold of 3FCR had the specific activities presented in Table 4.

TABLE 4

Specific activities (U/mg) for 3FCR mutants in kinetic resolution mode.

| TA | Substrate | | | |
|---|---|---|---|---|
| | 1a | 3a | 4a | 6a |
| 3FCR Y59W/T231A | 0.005 | 0.92 | 0.08 | 0.83 |
| 3FCR Y59W/Y87F/T231A | 0.32 | 3.3 | 0.51 | 2.3 |
| 3FCR Y59W/Y87F/Y152F/T231A | 0.54 | 2.9 | 0.66 | 1.0 |
| 3FCR Y59W/Y87F/Y152F/T231A/P423H | 0.62 | 8.9 | 1.38 | 1.4 |

In this table the gradual increase of the activity for substrates 1a, 3a and 4a with each mutation added is exemplified. The increase in the activity towards these bulky substrates does not necessarily goes hand-in-hand with the activity towards the standard substrate 6a.

The operational stability of the most interesting mutants was evaluated at 25° C. Purified enzymes were incubated in the storage buffer (HEPES buffer, 50 mM, pH 7.5, with the addition of 0.1 mM PLP) at the specified temperature, without shaking. At specific time intervals, aliquots of the incubated enzymes were withdrawn and the remaining activity was monitored with the direct test described in paragraph B2 of the General Procedures, using rac-amine 6a as amine donor.

The activity measured prior to the incubation for each mutant was defined as 100%, respectively. The results are presented in FIG. 1.

Mutations Y59W, Y87F, Y152F and T231A were incorporated into several putative transaminases that were identified by a BLAST search in NCBI. The amino acid sequence of 3FCR Y59W/Y87F/Y152F/T231A was used for the query in the non-redundant protein sequence database. No sequence was found in the first 100 results to have any of these four mutations; all sequences were conserved in these positions, namely having Tyr 59, Tyr 87, Tyr 152 and Thr 231. Sequences with identity as low as 69.6% were selected (SEQ ID NO: 5-11) and the synthetic genes were ordered with the four mutations in the respective positions (SEQ ID NO: 32 and 34-38, respectively, for the amino acid sequence. All TAs were expressed solubly, apart from ATA-4. The specific activity of the transaminases was determined for the kinetic resolution of amines 1a, 3a, 4a and 6a according to the test described in paragraph B2 of the General Procedures, with purified TAs.

TABLE 5

Specific activities (U/mg) of the putative transaminases identified in the BLAST search, incorporating the Y59W/Y87F/Y152F/T231A mutations, in kinetic resolution mode.

| TA | Substrate | | | |
|---|---|---|---|---|
| | 1a | 3a | 4a | 6a |
| Mutant ATA-3 | 0.071 | 1.0 | 0.16 | 0.079 |
| Mutant ATA-5 | 0.16 | 0.4 | 0.18 | 0.38 |
| Mutant ATA-6 | 0.117 | 0.6 | 0.058 | 0.32 |
| Mutant ATA-7 | 0.17 | 0.9 | 0.40 | 0.90 |
| Mutant ATA-8 | 0.40 | 1.9 | 0.54 | 1.2 |
| Mutant ATA-9 | 0.35 | 4.3 | 0.50 | 0.9 |

The motif found in 3FCR, and tested in 3GJU can be transferred to enzymes with sequence identity of at least 65% and yield interesting activities for the substrates 1a, 3a and 4a.

Example 2: Improvement of the TA Specific Activity for the Kinetic Resolution of Rac-Amines 1a, 2a, 3a, 4a and 6a by Incorporation of the Mutations The specific activity of the presented mutants was determined for the kinetic resolution of rac-amines 1a, 2a, 3a, 4a and 6a according to the test described in paragraph B2 of the General Procedures, with purified TAs. The positions were identified in the 3FCR scaffold and then transferred into the 3GJU scaffold, for confirmation of their significance in the acceptance of the amines of interest. The identity of SEQ ID NO: 1 and SEQ ID NO: 3 is 71.3%.

TABLE 6

Specific activities (U/mg) for 3FCR and 3GJU mutants in kinetic resolution mode.

| TA | Substrate | | | | |
|---|---|---|---|---|---|
| | 1a | 2a | 3a | 4a | 6a |
| 3FCR | n.a. | n.a. | 0.001 | 0.014 | 0.01 |
| 3FCR Y59W/Y87L/T231A | 0.23 | 0.009 | 0.4 | 0.02 | 0.1 |
| 3FCR Y59W/Y87V/T231A | 0.17 | 0.005 | 0.1 | 0.01 | 0.1 |
| 3GJU | n.a. | n.a. | 0.003 | n.d. | 0.003 |
| 3GJU Y59W/Y87L/T231A | 0.09 | 0.004 | 0.22 | 0.050 | 0.008 | n.a.: not active;
n.d.: not determined.

Position 87 is significant for the acceptance of substrate 2a/b. An aliphatic hydrophobic residue like Leu or Val in necessary in this position to facilitate the acceptance. The effect can be transferred to homologous proteins (like 3GJU, seq. identity: 71.3%).

Example 3: Improvement of the TA Specific Activity for the Kinetic Resolution of Rac-Amine 5a by Incorporation of the Mutations The specific activity of the presented mutants was determined for the kinetic resolution of rac-amine 5a according to the test described in paragraph B2 of the General Procedures, with purified TAs. The positions were identified in the 3FCR scaffold.

TABLE 7

Relative activity of 3FCR mutants in kinetic resolution of rac-amine 5a. The activity of 3FCR Y59W/T231A was used as reference (100%). For comparison, the specific activity (U/mg) towards substrate 6a is provided.

| TA | Substrate | |
|---|---|---|
| | 5a (%) | 6a (U/mg) |
| 3FCR Y59W/T231A | 100% | 0.83 |
| 3FCR T231A | 240% | 0.16 |
| 3FCR Y59W/T231G | 900% | 2.4 |
| 3FCR Y59W/Y87F/T231A/P423H | 540% | 4.5 |
| 3FCR Y59F/T231A | 420% | 1.1 |
| 3FCR Y59F/Y152F/T231G | 1470% | 0.71 |
| 3FCR Y59W/T231A/I234F | 520% | 0.08 |
| 3FCR Y59W/T231A/I234M | 460% | 0.90 |
| 3FCR Y59W/Y87F/Y152F/T231A/I234F | 169% | 0.03 |
| 3FCR Y59W/Y87F/Y152F/T231A/I234M | 247% | 0.26 |

The beneficial effect of Y59F and T231G substitution in 3FCR scaffold for the activity towards substrate 5a is proven. Their combination in the variant Y59F/Y152F/T231G yielded the best variant so far for substrate 5a relative to substrate 6a. More than that, the beneficial effect of the substitution of position 234 to Phe or Met could be shown.

Example 4: Improvement of the TA Specific Activity for the Use of Iso-Propylamine as Amine Donor The specific activity of the presented mutants was determined for use of iso-propylamine as amine donor according to the test described in paragraph B2 of the General Procedures, with purified TAs. The positions were identified in the 3FCR scaffold.

TABLE 8

Relative activity of 3FCR mutants using iso-propylamine as amine donor. The activity of 3FCR Y59W/T231A was used as reference (100%). For comparison, the specific activity (U/mg) towards substrate 6a is provided.

| TA | Substrate | |
|---|---|---|
| | iso-propylamine (%) | 6a (U/mg) |
| 3FCR Y59W/T231A | 100% | 0.83 |
| 3FCR | 145% | 0.01 |
| 3FCR T231A | 280% | 0.16 |
| 3FCR Y59W/T231A/I234F | 860% | 0.08 |
| 3FCR Y59W/T231A/I234M | 475% | 0.90 |
| 3FCR Y59W/Y87F/Y152F/T231A | 43% | 1.0 |
| 3FCR Y59W/Y87F/Y152F/T231A/I234F | 208% | 0.03 |
| 3FCR Y59W/Y87F/Y152F/T231A/I234M | 91% | 0.26 |

It can be concluded that the substitutions at position 234 have a beneficial effect of on the activity towards iso-propylamine.

Example 5: Asymmetric Synthesis of Chiral Amines 1a, 3a and 4a, Using L-Alanine as Amine Donor A glass vial of 2 mL containing 0.5 mL of reaction mixture (HEPES buffer, 50 mM, pH 8.0) of 8 mM ketone (1, 3 or 4), 200 mM L-alanine, 20% DMSO, 25 mM glucose, 5 mM NADH, 0.5 mg/mL glucose dehydrogenase GDH-105 (Codexis), 5 µL/mL L-lactic dehydrogenase (LDH) from bovine heart (L2625-50KU, Sigma), 1 mM PLP and the TA of interest, was incubated at 30° C. in a thermoshaker (Eppendorf), with a shaking speed of 600 rpm. After 20 h the reaction is terminated by thermal denaturation of the enzymes at 90° C. for 10 min. The reaction is cooled down to room temperature, and an equal amount of acetonitrile containing 0.1% diethylamine is added to the reaction mixture. The mixture was centrifuged at 17000 g for 1 min to remove the precipitated protein and the supernatant was filtered into an inlet, for HPLC analysis (Chiralpak OD-RH column, 150*4.6 mm, 5 µm particle at 30° C.; isocratic method with 50% acetonitrile and 50% $H_2O$ containing 0.1% diethylamine, at a flow of 0.5 mL/min). Conversion is defined as [total amine, mM/(total amine, mM+ketone, mM)*100].

TABLE 9

Conversion (%) and enantiomeric ratio (er, %) in the asymmetric synthesis of chiral amines, using L-alanine as amine donor.

| Substr. | TA | Conversion (%) | er (S:R, %) |
|---|---|---|---|
| 1b | 3FCR Y59W/Y87F/Y152F/T231A | 81% | 2:98% |
| 3b | 3FCR Y59W/T231A | 85% | >99.5:0.5% |
| 3b | 3FCR Y59W/Y87F/Y152F/T231A | 99% | >99.5:0.5% |
| 4b | 3FCR Y59W/T231A | 99% | n.d. |
| 4b | 3FCR Y59W/Y87F/Y152F/T231A | 100% | n.d. |

Enzyme concentration was 1.8 mg/mL;
n.d. not determined

Asymmetric synthesis at a scale of 8 mM ketone (for production of chiral amines 1a, 3a and 4a) can be performed with desirable conversions and enantioselectivity, using L-alanine as amine donor in less than a day (20 h). Various variants catalyzed the reaction efficiently.

Example 6: Asymmetric Synthesis of Amine 5a, Using Alanine as Amine Donor

A glass vial of 2 mL containing 0.5 mL of reaction mixture (HEPES buffer, 50 mM, pH 8.0) of 8 mM ketone 5, 200 mM L-alanine, 20% DMSO, 25 mM glucose, 5 mM NADH, 0.5 mg/mL glucose dehydrogenase GDH-105 (Codexis), 5 µL/mL L-lactic dehydrogenase (LDH) from bovine heart (L2625-50KU, Sigma), 1 mM PLP and the TA of interest, was incubated at 30° C. in a thermoshaker (Eppendorf), with a shaking speed of 600 rpm. After 20 h the reaction is terminated by thermal denaturation of the enzymes at 90° C. for 10 min. The reaction is cooled down to room temperature and an equal amount of acetonitrile containing 0.1% diethylamine is added to the reaction mixture. The mixture was centrifuged at 17000 g for 1 min to remove the precipitated protein and the supernatant was filtered into an inlet, for HPLC analysis (Chiralpak OD-RH column, 150*4.6 mm, 5 µm particle at 30° C.; isocratic method with 30% acetonitrile and 70% H$_2$O containing 0.1% diethylamine, at a flow of 0.5 mL/min). Conversion is defined as [total amine, mM/(total amine, mM+ketone, mM)*100].

TABLE 10

Conversion (%) of the asymmetric synthesis of amine 5a, using L-alanine as amine donor.

| TA | Enzyme concentration (mg/mL) | Conversion (%) |
|---|---|---|
| 3FCR Y59W/Y87F/Y152F/T231A/I234M | 1.6 | 66% |
| 3FCR Y59W/Y87F/Y152F/T231A/I234F | 0.2 | 40% |

Asymmetric synthesis at a scale of 8 mM ketone for substrate 5a/b can be performed with desirable conversions and enantioselectivity, using L-alanine as amine donor in less than a day (20 h). Various TA mutants catalyzed the reaction efficiently.

Example 7: Asymmetric Synthesis of Chiral Amine 1a, (R)-(4-Chlorophenyl)-Phenylmethaneamine, Using Alanine as Amine Donor In 53.5 ml reaction buffer (HEPES 100 mM pH 8.0; 4 mM PLP; 400 mM D,L-alanine) 4.5 g pyruvate reductase mix (5.4 mg GDH-102 [Codexis]; 21.6 mg LDH-101 [Codexis]; 126 mg NAD [Roche]; 4.32 g D-glucose) was dissolved. The purified mutant transaminase 3FCR Y59W/Y87F/Y152F/T231A was added subsequently as solution (22 ml, protein 2.6 mg/ml; see A3) and stirred for 5 minutes at 30° C. The reaction was started by the addition 100 mg (4-chlorophenyl)(phenyl)methanone dissolved in 20 ml DMSO. The reaction pH was manually adjusted to 8.0 (2N NaOH) and kept constant by the automated addition of 0.1 N NaOH. At the beginning the yellow reaction solution was slightly turbid. After 24 h and a conversion of 98 area % (IPC-HPLC) the reaction was acidified to pH 2.0 to precipitate the enzymes. 1.125 g filtration aid (Dicalite) was added and the mixture was stirred 20 minutes. Subsequently, the reaction mixture was filtrated through 20 g filter aid (Dicalite) bed and the filter cake was washed with 40 ml 0.1 N HCl. The pH of the combined, slightly yellow, clear aqueous solutions was adjusted to pH 10, changing the solution color to orange, for the amine extraction using twice 50 ml TBME. The combined organic phases were dried over MgSO$_4$, filtrated and evaporated under vacuum at 40° C. yielding in 122 mg (122%) light yellow oil as crude product of the title compound 1a.

HCl-salt formation: The crude product was dissolved in 5 ml TBME and under stirring 350 µl 2 M HCl was added using a syringe. The formed suspension was allowed to stir for 2 h at room temperature prior to its filtration (paper filter). The isolated HCl-salt was washed with TBME and dried 3 h under high vacuum at room temperature yielding in 95 mg (82%) white powder.

Chemical purity HPLC: 99.7 area % [210 nm; X-Bridge C8; 50*4.6 mm, 2.5 µm, flow 2 ml, 45° C., A: H$_2$O/ACN (95/5), 50→10% in 3 min, hold 0.5 min, B: ACN, 40→80% in 3 min, hold 0.5 min, C: 100 mmol ammonium acetate in H$_2$O/ACN (95/5), 10% isocratic]; chiral HPLC: 97.1% (R), 2.9% (S) [235 nm; Chrownpack CR-I(+); 150*3 mm, 5 µm, flow 0.4 ml, 40° C., A: 55% 3.6 g perchloric acid in H$_2$O, B: 45% ACN]; $^1$H NMR (600 MHz, CH$_3$OD) δ ppm 7.20-7.49 (m, 9H), 5.57 (s, 1H); GC-MS: 217 (M)$^+$.

Example 8: Kinetic Resolution of Amine 2a Using Pyruvate as Amine Acceptor for the Preparation of (S)-2,2-Dimethyl-1Phenyl Propan-1-Amine In 89.75 ml reaction buffer (TRIS 50 mM pH 8.5; 1 mM PLP) 129 mg sodium pyruvate and the purified solution of mutant transaminase 3FCR Y59W/Y87L/T231A (18.5 ml, protein 2.47 mg/ml; see A3) were added subsequently and stirred for 5 minutes at 30° C. The reaction was started by the addition 100 mg 2,2-dimethyl-1phenylpropan-1-amine dissolved in 1 ml DMSO. After 48 h and a conversion of roughly 55 area % (IPC-HPLC), the reaction was acidified to pH 2.0 to precipitate the enzymes and was stirred 20 minutes. Subsequently, the reaction mixture was filtrated through 25 g filter aid (Dicalite) bed and subsequently, the filter cake was washed with deionized water and 50 ml TBME. After phase separation the aqueous phase was extracted with 50 ml TBME to remove the 2,2-dimethyl-1-phenyl-propan-1-one 2b. The combined organic phases were dried over MgSO$_4$, filtrated and evaporated under vacuum at 40° C. yielding in 25 mg (26.5%; chiral HPLC: 99 area %) 2,2-dimethyl-1-phenyl-propan-1-one 2b as yellow vicious oil. The pH of the aqueous phase was adjusted to 12 using 2N NaOH and subsequently extracted twice with 50 ml TBME. The combined organic phases were dried over MgSO$_4$, filtrated and evaporated under vacuum at 40° C. yielding in 38 mg (40%) (S)-2,2-dimethyl-1-phenyl-propan-1-amine 2a as yellow oil.

Chiral HPLC: 98.1% (S), 1.9% (R) [220 nm; Chiracel OD-3R; 150*4.6 mm, 3 μm, flow 1.0 ml, 25° C., A: 50% ACN, B: 50% 6.3 g ammonium formate in 950 ml $H_2O$: 50 ml ACN]; $^1H$ NMR (600 MHz, $CDCl_3$) δ ppm 7.27-7.31 (m, 4H), 7.24 (dt, J=6.0, 2.6 Hz, 1H), 3.71 (s, 1H), 0.91 (s, 9H); GC-MS: 162 (M).

Example 9: Asymmetric Synthesis of Chiral Amine 3a, (S)-1,3-Diphenyl Propylamine, Using Alanine as Amine Donor In 68 ml reaction buffer (HEPES 100 mM pH 8.0; 4 mM PLP; 400 mM D,L-alanine) 4.5 g pyruvate reductase mix (5.4 mg GDH-102 [Codexis]; 21.6 mg LDH-101[Codexis]; 126 mg NAD [Roche]; 4.32 g D-glucose) was dissolved. The purified mutant transaminase 3FCR Y59W/Y87F/Y152F/T231A was added subsequently as solution (6.8 ml, protein 2.6 mg/ml; see A3) and stirred for 5 minutes at 30° C. The reaction was started by the addition 100 mg 1,3-diphenyl propan-1-one dissolved in 20 ml DMSO. The reaction pH was kept constant by the automated addition of 0.1 N NaOH. At the beginning the yellow reaction solution was slightly turbid. After 24 h and a conversion of 98 area % (IPC-HPLC), the reaction was acidified to pH 2.0 to precipitate the enzymes. 1.125 g filtration aid (Dicalite) was added and the mixture was stirred 20 minutes. Subsequently, the reaction mixture was filtrated through 20 g filter aid (Dicalite) bed and the filter cake was washed with 40 ml 0.1 N HCl. The pH of the combined, slightly yellow, clear aqueous solutions was adjusted to pH 10, changing its color to orange, for the amine extraction using twice 50 ml TBME. The combined organic phases were dried over $MgSO_4$, filtrated and evaporated under vacuum at 40° C. yielding in 95 mg (95%) light yellow oil as crude product of the title compound 3a.

HCl-salt formation: The crude product was dissolved in 5 ml TBME and under stirring 360 μl 2 M HCl was added using a syringe. The formed suspension was allowed to stir for 2 h at room temperature prior to its filtration (paper filter). The isolated HCl-salt was washed with TBME and dried 3 h under high vacuum at room temperature yielding in 84 mg (71%) white powder as HCl salt of the title compound 3a.

Chemical purity HPLC: 99.0 area % [210 nm; X-Bridge C8; 50*4.6 mm, 2.5 μm, flow 2 ml, 45° C., A: $H_2O$/ACN (95/5), 60→10% in 3 min, hold 0.5 min, B: ACN, 830→0% in 3 min, hold 0.5 min, C: 100 mmol Ammonium acetate in $H_2O$/ACN (95/5), 10% isocratic]; chiral HPLC: 100% (S) [222 nm; Chiralpak IF 3; 150*4.6 mm, flow 1 ml, 40° C., A: 90% heptane with 0.1% diethylamine, B: 10% ethanol]; $^1H$ NMR (600 MHz, $CH_3OD$) δ ppm 7.44-7.59 (m, 5H), 7.28-7.33 (m, 2H), 7.12-7.24 (m, 3H), 4.24 (dd, J=9.6, 5.6 Hz, 1H), 2.55 (br t, J=7.9 Hz, 2H), 2.22-2.42 (m, 2H); LC-MS: 212 $(M+H)^+$.

Example 10: Asymmetric Synthesis of Chiral Amine 4a, (S)-Acenaphthen-1-Ylamine, Using Alanine as Amine Donor In 60.5 ml reaction buffer (HEPES 100 mM pH 8.0; 4 mM PLP; 400 mM D,L-alanine) 4.5 g pyruvate reductase mix (5.4 mg GDH-102 [Codexis]; 21.6 mg LDH-101[Codexis]; 126 mg NAD [Roche]; 4.32 g D-glucose) was dissolved. The purified aminotransaminase 3FCR Y59W/Y87F/Y152F/T231A was added subsequently as solution (15 ml, protein 2.6 mg/ml; see A3) and stirred for 5 minutes at 30° C. The reaction was started by the addition 100 mg 2H-Acenaphthylen-1-one dissolved in 20 ml DMSO. The reaction pH was manually adjusted to 8.0 (2N NaOH) and kept constant by the automated addition of 0.1 N NaOH. At the beginning the yellow reaction solution was slightly turbid. To prevent potential oxidative aromatization the reaction was carried out under $N_2$ atmosphere and in the dark. After 46 h and a conversion of 98 area % (IPC-HPLC) the reaction was acidified to pH 2.0 to precipitate the enzymes. 5 g filtration aid (Dicalite) was added and the mixture was stirred 20 minutes. Subsequently, the reaction mixture was filtrated through 20 g filter aid (Dicalite) bed and the filter cake was washed with 40 ml 0.1 N HCl and with 50 ml TBME. The pH of the combined, slightly yellow, clear aqueous solutions was adjusted to pH 10, prior to the amine extraction using 50 ml TBME. The combined organic phases were dried over $MgSO_4$, filtrated and evaporated under vacuum at 40° C. yielding in 112 mg (112%) orange-brown oil as crude product of the title compound 4a.

HCl-salt formation: The crude product was dissolved in 5 ml TBME and under stirring 445 μl 2 M HCl was added using a syringe. The formed very fine suspension was allowed to stir for 1 h at room temperature prior to its centrifugation (5 min.; 4000 rpm). After decantation of TBME, the remaining solid was re-suspended in 10 ml TBME, vigorously mixed, centrifuged (5 min.; 4000 rpm) and once more decanted. The moist HCl-salt was evaporated under vacuum at 40° C. and dried 3 h under high vacuum at room temperature yielding in 84 mg (69%) beige powder as HCl salt of the title compound 4a.

Chemical and chiral purity HPLC: 81.5% (S): 18.5% (R) [232 nm; Chiracel OJ-3; 150*4.6 mm, 3 μm; flow 2.5 ml, 30° C., A: 96% heptane with 0.1% diethylamine, B: 4% ethanol]; $^1H$ NMR (600 MHz, $CH_3OD$) δ ppm: 7.90 (d, J=8.1 Hz, 1H), 7.77 (d, J=8.3 Hz, 1H), 7.54-7.70 (m, 3H), 7.46 (d, J=6.9 Hz, 1H), 5.32 (dd, J=8.1, 2.7 Hz, 1H), 3.99 (dd, J=17.8, 8.1 Hz, 1H), 3.41 (dt, J=17.8, 1.3 Hz, 1H); LC-MS: 171.1 $(M+H)^+$.

Example 11: Asymmetric Synthesis of Amine 5a, exo-3-amino-8-aza-bicyclo[3.2.1]oct-8-yl)-phenyl-methanone, Using 2-propylamine as Amine Donor Into 82 ml reaction buffer (HEPES 50 mM; 2 mM PLP; 0.2 M 2-propylamine hydrochloride; pH 7.5) the purified mutant transaminase 3FCR Y59W/Y87F/Y152F/T231A/I234M solution (in total 78 ml, protein 1.1 mg/ml; see A3) and 100 mg 8-Benzoyl-8-aza-bicyclo[3.2.1]octan-3-one 5b dissolved in 20 ml DMSO were added under stirring at 30° C. The reaction was allowed to proceed for 9 d enabling a conversion of 75 area % (IPC-HPLC). After 9d the reaction was acidified to pH 2.0 to precipitate the enzymes and was stirred 15 minutes. Subsequently, the reaction mixture was filtrated through 25 g filter aid (Dicalite) bed and extracted twice with 50 ml dichloromethane to remove the 8-Benzoyl-8-aza-bicyclo[3.2.1]octan-3-one 5b. The combined organic phases were dried over $MgSO_4$, filtrated and evaporated under vacuum at 40° C. yielding in 37 mg (HPLC: 97 area %) 8-Benzoyl-8-aza-bicyclo[3.2.1]octan-3-one 5b as slightly yellow oil. The pH of the aqueous phase was adjusted to 12 using 2N NaOH and subsequently extracted four times with 50 ml dichloromethane. The combined organic phases were dried over $MgSO_4$, filtrated, evaporated under vacuum at 40° C. and dried 36 h under high vacuum at 60° C. yielding in 60 mg (60%) as yellow oil of the title compound 5a.

Chemical purity HPLC: 98.9 area % [210 nm; X-Bridge C8; 50*2.1 mm, 2.5 μm, flow ml, 40° C., A: 90% 10 mmol Ammonium acetate in H₂O/ACN (95/5), B: ACN, 10%]; chiral SFC: 100% exo [210 nm; Chiralpak AD-3; 150*4.6 mm, 5 μm; flow 3 ml; left 40° C.; right 42° C.; A: 82% CO₂, B: 18% methanol with 0.2% 2-propylamine]; ¹H NMR (600 MHz, DMSO-d₆, 120° C.) δ ppm 7.44 (s, 5H), 4.29 (br s, 2H), 3.16 (dt, J=11.1, 5.5 Hz, 1H), 1.86-2.00 (m, 3H), 1.79 (ddd, J=13.2, 5.1, 3.0 Hz, 3H), 1.67-1.75 (m 3H), 1.34-1.47 (m, 2H); LC-MS: 231 (M+H)⁺.

| SEQUENCES |
|---|
| Wild-type Sequences (plus tags): |
| 3FCR wild-type (plus tag): amino acid |
| (SEQ ID NO: 1 + SEQ ID NO: 56) |
| MLKNDQLDQW DRDNFFHPST HLAQHARGES ANRVIKTASG VFIEDRDGTK LLDAFAGLYC 60 |
| VNVGYGRQEI AEAIADQARE LAYYHSYVGH GTEASITLAK MILDRAPKNM SKVYFGLGGS 120 |
| DANETNVKLI WYYNNILGRP EKKKIISRWR GYHGSGLVTG SLTGLELFHK KFDLPVEQVI 180 |
| HTEAPYYFRR EDLNQTEEQF VAHCVAELEA LIEREGADTI AAFIGEPILG TGGIVPPPAG 240 |
| YWEAIQTVLN KHDILLVADE VVTGFGRLGT MFGSDHYGLE PDIITIAKGL TSAYAPLSGS 300 |
| IVSDKVWKVL EQGTDENGPI GHGWTYSAHP IGAAAGVANL KLLDELNLVS NAGEVGAYLN 360 |
| ATMAEALSQH ANVGDVRGEG LLCAVEFVKD RDSRTFFDAA DKIGPQISAK LLEQDKIIAR 420 |
| AMPQGDILGF APPFCLTRAE ADQVVEGTLR AVKAVLG-(SHHHHHH) |
| 430          440          450 |
| |
| 3FCR wild-type plus tag: nucleic acid (SEQ ID NO: 2) |
| ATGCTGAAAAACGACCAACTGGACCAATGGGACCGTGATAACTTCTTCCACCCGTCAACGCACCTGGCGCAACATGCCCGT |
| GGCGAATCAGCTAACCGTGTGATCAAAACCGCGTCGGGCGTTTTTATTGAAGATCGCGACGGTACGAAACTGCTGGATGCT |
| TTCGCGGGCCTGTATTGCGTTAATGTCGGCTACGGTCGTCAGGAAATTGCCGAAGCAATCGCTGATCAAGCGCGCGAACTG |
| GCCTATTACCATAGCTATGTGGGCCACGGTACCGAAGCTTCTATCACGCTGGCGAAAATGATTCTGGATCGTGCCCCGAAA |
| AACATGAGTAAAGTTTACTTTGGTCTGGGCGGTTCCGACGCAAACGAAACCAATGTCAAACTGATCTGGTATTACAACAAT |
| ATTCTGGGCCGCCCGGAGAAAAAGAAAATTATCAGTCGTTGGCGCGGTTATCATGGCAGTGGTCTGGTTACCGGCTCCCTG |
| ACGGGTCTGGAACTGTTTCATAAAAAATTCGATCTGCCGGTGGAACAGGTTATTCACACCGAAGCCCCGTATTACTTTCGT |
| CGCGAAGACCTGAACCAGACGGAAGAACAATTCGTCGCACACTGTGTGGCTGAACTGGAAGCGCTGATCGAACGTGAAGGC |
| GCGGATACCATTGCGGCCTTCATCGGCGAACCGATTCTGGGTACGGGCGGTATTGTGCCGCCGCCGGCCGGTTATTGGGAA |
| GCAATCCAGACCGTCCTGAATAAACATGATATTCTGCTGGTTGCGGACGAAGTGGTTACCGGCTTTGGTCGCCTGGGCACG |
| ATGTTCGGTTCTGATCACTATGGCCTGGAACCGGACATTATCACCATCGCGAAAGGTCTGACGTCAGCGTACGCCCCGCTG |
| AGCGGTTCTATTGTGTCGGATAAAGTCTGGAAAGTGCTGGAACAGGGCACCGACGAAAACGGTCCGATCGGCCATGGTTGG |
| ACGTATAGCGCACACCCGATTGGTGCAGCTGCAGGTGTTGCAAATCTGAAACTGCTGGATGAACTGAACCTGGTTAGCAAT |
| GCCGGCGAAGTCGGTGCCTACCTGAACGCAACCATGGCAGAAGCTCTGTCCCAACATGCTAATGTTGGCGATGTCCGTGGC |
| GAAGGTCTGCTGTGCGCGGTGGAATTTGTTAAAGATCGTGACAGCCGCACGTTTTTCGATGCCGCAGACAAAATCGGTCCG |
| CAGATTTCTGCGAAACTGCTGGAACAAGATAAAATTATCGCGCGTGCCATGCCGCAGGGCGACATTCTGGGTTTTGCCCCG |
| CCGTTCTGTCTGACCCGCGCAGAAGCTGATCAAGTCGTGGAAGGTACGCTGCGCGCTGTCAAAGCCGTTCTGGGTTCACAT |
| CACCATCACCACCACTAA |
| |
| 3GJU wild-type (plus tag): amino acid |
| (SEQ ID NO: 3 + SEQ ID NO: 56) |
| MLNQSNELNA WDRDHFFHPS THMGTHARGE SPTRIMAGGE GVTVWDNNGR KSIDAFAGLY 60 |
| CVNVGYGRQK IADAIATQAK NLAYYHAYVG HGTEASITLA KMIIDRAPKG MSRVYFGLSG 120 |
| SDANETNIKL IWYYNNVLGR PEKKKIISRW RGYHGSGVMT GSLTGLDLFH NAFDLPRAPV 180 |
| LHTEAPYYFR RTDRSMSEEQ FSQHCADKLE EMILAEGPET IAAFIGEPIL GTGGIVPPPA 240 |
| GYWEKIQAVL KKYDVLLVAD EVVTGFGRLG TMFGSDHYGI KPDLITIAKG LTSAYAPLSG 300 |
| VIVADRVWQV LVQGSDKLGS LGHGWTYSAH PICVAAGVAN LELIDEMDLV TNAGETGAYF 360 |

| SEQUENCES |
| --- |

RAELAKAVGG HKNVGEVRGD GMLAAVEFVA DKDDRVFFDA SQKIGPQVAT ALAASGVIGR  420

AMPQGDILGF APPLCLTREQ ADIVVSKTAD AVKSVFANL-(SHHHHHH)

3GJU wild-type plus tag: nucleic acid (SEQ ID NO: 4)
```
atgctgaacc aatcgaacga actgaacgcc tgggatcgcg accactttt ccacccgtca   60
acgcacatgg gcacgcacgc acgcggcgaa agtccgaccc gtatcatggc cggcggtgaa  120
ggcgttacgg tctgggataa caatggtcgc aaatccattg acgcgtttgc cggcctgtat  180
tgcgtgaacg ttggctacgg tcgccagaaa attgcagatg ctatcgcgac ccaagctaaa  240
aatctggcgt attaccatgc ctatgtgggc cacggtaccg aagcgagcat tacgctggcc  300
aaaatgatta tcgatcgtgc gccgaaaggc atgtctcgcg tttacttcgg cctgagcggt  360
tctgatgcca cgaaaccaa catcaaactg atctggtact acaacaacgt cctgggccgt  420
ccggagaaaa agaaaattat ctcccgttgg cgcggttatc atggcagcgg tgttatgacc  480
ggctctctga cgggtctgga cctgtttcat aacgcattcg acctgccgcg tgctccggtg  540
ctgcacaccg aagccccgta ttactttcgt cgcacggatc gcagtatgtc cgaagaacag  600
ttcagccaac actgtgcaga caaactggaa gaaatgattc tggctgaagg cccggaaacc  660
attgcggcct tatcggcga accgattctg gtacgggcg gtatcgttcc gccgccggcg  720
ggttattggg aaaaaattca ggccgtcctg aaaaaatacg atgtgctgct ggttgcggac  780
gaagtggtta ccggctttgg tcgcctgggc acgatgttcg gttcagatca ttatggcatc  840
aaaccggacc tgattaccat cgcaaaaggc ctgacgagtg cctacgcacc gctgtccggt  900
gtcattgtgg cggatcgtgt gtggcaggtt ctggtccaag gctcagacaa actgggttcg  960
ctgggccatg gttggaccta ttcggcacac ccgatctgcg tggcagctgg tgttgccaac 1020
ctggaactga ttgatgaaat ggacctggtg accaatgcgg gcgaaacggg tgcatatttt 1080
cgtgctgaac tggctaaagc ggttggcggt cacaaaaatg tcggcgaagt gcgcggcgat 1140
ggtatgctgg cggccgttga attcgtcgca gataaagatg accgtgtgtt tttcgacgct 1200
tcacagaaaa tcggtccgca agtcgcaacc gcactggcag cttcgggtgt gatcggtcgt 1260
gcaatgccgc agggcgatat tctgggtttt gccccgccgc tgtgtctgac ccgtgaacag 1320
gcagatattg tcgtgagcaa aacggccgac gctgtcaaat cagtcttcgc aaacctgtca 1380
caccaccatc accaccacta a                                          1401
```

ATA-3: amino acid illustrated in FIG. 2 (SEQ ID NO: 5)

ATA-4: amino acid illustrated in FIG. 2 (SEQ ID NO: 6)

ATA-5: amino acid illustrated in FIG. 2 (SEQ ID NO: 7)

ATA-6: amino acid illustrated in FIG. 2 (SEQ ID NO: 8)

ATA-7: amino acid illustrated in FIG. 2 (SEQ ID NO: 9)

ATA-8: amino acid illustrated in FIG. 2 (SEQ ID NO: 10)

ATA-9: amino acid illustrated in FIG. 2 (SEQ ID NO: 11)

Sequences of Double Mutants:
3FCR Y59W/T231A: amino acid (SEQ ID NO: 12)
MLKNDQLDQW DRDNFFHPST HLAQHARGES ANRVIKTASG VFIEDRDGTK LLDAFAGLWC   60

VNVGYGRQEI AEAIADQARE LAYYHSYVGH GTEASITLAK MILDRAPKNM SKVYFGLGGS  120

DANETNVKLI WYYNNILGRP EKKKIISRWR GYHGSGLVTG SLTGLELFHK KFDLPVEQVI  180

HTEAPYYFRR EDLNQTEEQF VAHCVAELEA LIEREGADTI AAFIGEPILG AGGIVPPPAG  240

| SEQUENCES | |
|---|---|
| YWEAIQTVLN KHDILLVADE VVTGFGRLGT MFGSDHYGLE PDIITIAKGL TSAYAPLSGS | 300 |
| IVSDKVWKVL EQGTDENGPI GHGWTYSAHP IGAAAGVANL KLLDELNLVS NAGEVGAYLN | 360 |
| ATMAEALSQH ANVGDVRGEG LLCAVEFVKD RDSRTFFDAA DKIGPQISAK LLEQDKIIAR | 420 |
| AMPQGDILGF APPFCLTRAE ADQVVEGTLR AVKAVLG | 457 |

3FCR Y59W/T231G: amino acid (SEQ ID NO: 13)
MLKNDQLDQW DRDNFFHPST HLAQHARGES ANRVIKTASG VFIEDRDGTK LLDAFAGLWC 60
VNVGYGRQEI AEAIADQARE LAYYHSYVGH GTEASITLAK MILDRAPKNM SKVYFGLGGS 120
DANETNVKLI WYYNNILGRP EKKKIISRWR GYHGSGLVTG SLTGLELFHK KFDLPVEQVI 180
HTEAPYYFRR EDLNQTEEQF VAHCVAELEA LIEREGADTI AAFIGEPILG GGGIVPPPAG 240
YWEAIQTVLN KHDILLVADE VVTGFGRLGT MFGSDHYGLE PDIITIAKGL TSAYAPLSGS 300
IVSDKVWKVL EQGTDENGPI GHGWTYSAHP IGAAAGVANL KLLDELNLVS NAGEVGAYLN 360
ATMAEALSQH ANVGDVRGEG LLCAVEFVKD RDSRTFFDAA DKIGPQISAK LLEQDKIIAR 420
AMPQGDILGF APPFCLTRAE ADQVVEGTLR AVKAVLG 457

3FCR Y59F/T231A: amino acid (SEQ ID NO: 14)
MLKNDQLDQW DRDNFFHPST HLAQHARGES ANRVIKTASG VFIEDRDGTK LLDAFAGLFC 60
VNVGYGRQEI AEAIADQARE LAYYHSYVGH GTEASITLAK MILDRAPKNM SKVYFGLGGS 120
DANETNVKLI WYYNNILGRP EKKKIISRWR GYHGSGLVTG SLTGLELFHK KFDLPVEQVI 180
HTEAPYYFRR EDLNQTEEQF VAHCVAELEA LIEREGADTI AAFIGEPILG AGGIVPPPAG 240
YWEAIQTVLN KHDILLVADE VVTGFGRLGT MFGSDHYGLE PDIITIAKGL TSAYAPLSGS 300
IVSDKVWKVL EQGTDENGPI GHGWTYSAHP IGAAAGVANL KLLDELNLVS NAGEVGAYLN 360
ATMAEALSQH ANVGDVRGEG LLCAVEFVKD RDSRTFFDAA DKIGPQISAK LLEQDKIIAR 420
AMPQGDILGF APPFCLTRAE ADQVVEGTLR AVKAVLG 457

3GJU Y59W/T231A: amino acid (SEQ ID NO: 15)
MLNQSNELNA WDRDHFFHPS THMGTHARGE SPTRIMAGGE GVTVWDNNGR KSIDAFAGLW 60
CVNVGYGRQK IADAIATQAK NLAYYHAYVG HGTEASITLA KMIIDRAPKG MSRVYFGLSG 120
SDANETNIKL IWYYNNVLGR PEKKKIISRW RGYHGSGVMT GSLTGLDLFH NAFDLPRAPV 180
LHTEAPYYFR RTDRSMSEEQ FSQHCADKLE EMILAEGPET IAAFIGEPIL GAGGIVPPPA 240
GYWEKIQAVL KKYDVLLVAD EVVTGFGRLG TMFGSDHYGI KPDLITIAKG LTSAYAPLSG 300
VIVADRVWQV LVQGSDKLGS LGHGWTYSAH PICVAAGVAN LELIDEMDLV TNAGETGAYF 360
RAELAKAVGG HKNVGEVRGD GMLAAVEFVA DKDDRVFFDA SQKIGPQVAT ALAASGVIGR 420
AMPQGDILGF APPLCLTREQ ADIVVSKTAD AVKSVFANL 459

3GJU Y59W/T231G: amino acid (SEQ ID NO: 16)
MLNQSNELNA WDRDHFFHPS THMGTHARGE SPTRIMAGGE GVTVWDNNGR KSIDAFAGLW 60
CVNVGYGRQK IADAIATQAK NLAYYHAYVG HGTEASITLA KMIIDRAPKG MSRVYFGLSG 120
SDANETNIKL IWYYNNVLGR PEKKKIISRW RGYHGSGVMT GSLTGLDLFH NAFDLPRAPV 180
LHTEAPYYFR RTDRSMSEEQ FSQHCADKLE EMILAEGPET IAAFIGEPIL GGGGIVPPPA 240
GYWEKIQAVL KKYDVLLVAD EVVTGFGRLG TMFGSDHYGI KPDLITIAKG LTSAYAPLSG 300
VIVADRVWQV LVQGSDKLGS LGHGWTYSAH PICVAAGVAN LELIDEMDLV TNAGETGAYF 360
RAELAKAVGG HKNVGEVRGD GMLAAVEFVA DKDDRVFFDA SQKIGPQVAT ALAASGVIGR 420
AMPQGDILGF APPLCLTREQ ADIVVSKTAD AVKSVFANL 459

| SEQUENCES |
|---|

3GJU Y59F/T231A: amino acid (SEQ ID NO: 17)
```
MLNQSNELNA WDRDHFFHPS THMGTHARGE SPTRIMAGGE GVTVWDNNGR KSIDAFAGLF      60

CVNVGYGRQK IADAIATQAK NLAYYHAYVG HGTEASITLA KMIIDRAPKG MSRVYFGLSG     120

SDANETNIKL IWYYNNVLGR PEKKKIISRW RGYHGSGVMT GSLTGLDLFH NAFDLPRAPV     180

LHTEAPYYFR RTDRSMSEEQ FSQHCADKLE EMILAEGPET IAAFIGEPIL GAGGIVPPPA     240

GYWEKIQAVL KKYDVLLVAD EVVTGFGRLG TMFGSDHYGI KPDLITIAKG LTSAYAPLSG     300

VIVADRVWQV LVQGSDKLGS LGHGWTYSAH PICVAAGVAN LELIDEMDLV TNAGETGAYF     360

RAELAKAVGG HKNVGEVRGD GMLAAVEFVA DKDDRVFFDA SQKIGPQVAT ALAASGVIGR     420

AMPQGDILGF APPLCLTREQ ADIVVSKTAD AVKSVFANL                           459
```

Sequences of Triple Mutants:
3FCR Y59W/Y87F/T231A: amino acid (SEQ ID NO: 18)
```
MLKNDQLDQW DRDNFFHPST HLAQHARGES ANRVIKTASG VFIEDRDGTK LLDAFAGLWC      60

VNVGYGRQEI AEAIADQARE LAYYHSFVGH GTEASITLAK MILDRAPKNM SKVYFGLGGS     120

DANETNVKLI WYYNNILGRP EKKKIISRWR GYHGSGLVTG SLTGLELFHK KFDLPVEQVI     180

HTEAPYYFRR EDLNQTEEQF VAHCVAELEA LIEREGADTI AAFIGEPILG AGGIVPPPAG     240

YWEAIQTVLN KHDILLVADE VVTGFGRLGT MFGSDHYGLE PDIITIAKGL TSAYAPLSGS     300

IVSDKVWKVL EQGTDENGPI GHGWTYSAHP IGAAAGVANL KLLDELNLVS NAGEVGAYLN     360

ATMAEALSQH ANVGDVRGEG LLCAVEFVKD RDSRTFFDAA DKIGPQISAK LLEQDKIIAR     420

AMPQGDILGF APPFCLTRAE ADQVVEGTLR AVKAVLG                             457
```

3FCR Y59W/Y87L/T231A: amino acid (SEQ ID NO: 19)
```
MLKNDQLDQW DRDNFFHPST HLAQHARGES ANRVIKTASG VFIEDRDGTK LLDAFAGLWC      60

VNVGYGRQEI AEAIADQARE LAYYHSLVGH GTEASITLAK MILDRAPKNM SKVYFGLGGS     120

DANETNVKLI WYYNNILGRP EKKKIISRWR GYHGSGLVTG SLTGLELFHK KFDLPVEQVI     180

HTEAPYYFRR EDLNQTEEQF VAHCVAELEA LIEREGADTI AAFIGEPILG AGGIVPPPAG     240

YWEAIQTVLN KHDILLVADE VVTGFGRLGT MFGSDHYGLE PDIITIAKGL TSAYAPLSGS     300

IVSDKVWKVL EQGTDENGPI GHGWTYSAHP IGAAAGVANL KLLDELNLVS NAGEVGAYLN     360

ATMAEALSQH ANVGDVRGEG LLCAVEFVKD RDSRTFFDAA DKIGPQISAK LLEQDKIIAR     420

AMPQGDILGF APPFCLTRAE ADQVVEGTLR AVKAVLG                             457
```

3FCR Y59W/Y87V/T231A: amino acid (SEQ ID NO: 20)
```
MLKNDQLDQW DRDNFFHPST HLAQHARGES ANRVIKTASG VFIEDRDGTK LLDAFAGLWC      60

VNVGYGRQEI AEAIADQARE LAYYHSVVGH GTEASITLAK MILDRAPKNM SKVYFGLGGS     120

DANETNVKLI WYYNNILGRP EKKKIISRWR GYHGSGLVTG SLTGLELFHK KFDLPVEQVI     180

HTEAPYYFRR EDLNQTEEQF VAHCVAELEA LIEREGADTI AAFIGEPILG AGGIVPPPAG     240

YWEAIQTVLN KHDILLVADE VVTGFGRLGT MFGSDHYGLE PDIITIAKGL TSAYAPLSGS     300

IVSDKVWKVL EQGTDENGPI GHGWTYSAHP IGAAAGVANL KLLDELNLVS NAGEVGAYLN     360

ATMAEALSQH ANVGDVRGEG LLCAVEFVKD RDSRTFFDAA DKIGPQISAK LLEQDKIIAR     420

AMPQGDILGF APPFCLTRAE ADQVVEGTLR AVKAVLG                             457
```

3FCR Y59W/Y87F/T231G: amino acid (SEQ ID NO: 21)
```
MLKNDQLDQW DRDNFFHPST HLAQHARGES ANRVIKTASG VFIEDRDGTK LLDAFAGLWC      60

VNVGYGRQEI AEAIADQARE LAYYHSFVGH GTEASITLAK MILDRAPKNM SKVYFGLGGS     120

DANETNVKLI WYYNNILGRP EKKKIISRWR GYHGSGLVTG SLTGLELFHK KFDLPVEQVI     180
```

| SEQUENCES |
|---|

```
HTEAPYYFRR EDLNQTEEQF VAHCVAELEA LIEREGADTI AAFIGEPILG GGGIVPPPAG    240

YWEAIQTVLN KHDILLVADE VVTGFGRLGT MFGSDHYGLE PDIITIAKGL TSAYAPLSGS    300

IVSDKVWKVL EQGTDENGPI GHGWTYSAHP IGAAAGVANL KLLDELNLVS NAGEVGAYLN    360

ATMAEALSQH ANVGDVRGEG LLCAVEFVKD RDSRTFFDAA DKIGPQISAK LLEQDKIIAR    420

AMPQGDILGF APPFCLTRAE ADQVVEGTLR AVKAVLG                             457

3FCR Y59F/Y87F/T231G: amino acid (SEQ ID NO: 57)
MLKNDQLDQW DRDNFFHPST HLAQHARGES ANRVIKTASG VFIEDRDGTK LLDAFAGLFC     60

VNVGYGRQEI AEAIADQARE LAYYHSFVGH GTEASITLAK MILDRAPKNM SKVYFGLGGS    120

DANETNVKLI WYYNNILGRP EKKKIISRWR GYHGSGLVTG SLTGLELFHK KFDLPVEQVI    180

HTEAPYYFRR EDLNQTEEQF VAHCVAELEA LIEREGADTI AAFIGEPILG GGGIVPPPAG    240

YWEAIQTVLN KHDILLVADE VVTGFGRLGT MFGSDHYGLE PDIITIAKGL TSAYAPLSGS    300

IVSDKVWKVL EQGTDENGPI GHGWTYSAHP IGAAAGVANL KLLDELNLVS NAGEVGAYLN    360

ATMAEALSQH ANVGDVRGEG LLCAVEFVKD RDSRTFFDAA DKIGPQISAK LLEQDKIIAR    420

AMPQGDILGF APPFCLTRAE ADQVVEGTLR AVKAVLG                             457

3FCR Y59W/T231A/I234F: amino acid (SEQ ID NO: 22)
MLKNDQLDQW DRDNFFHPST HLAQHARGES ANRVIKTASG VFIEDRDGTK LLDAFAGLWC     60

VNVGYGRQEI AEAIADQARE LAYYHSYVGH GTEASITLAK MILDRAPKNM SKVYFGLGGS    120

DANETNVKLI WYYNNILGRP EKKKIISRWR GYHGSGLVTG SLTGLELFHK KFDLPVEQVI    180

HTEAPYYFRR EDLNQTEEQF VAHCVAELEA LIEREGADTI AAFIGEPILG AGGFVPPPAG    240

YWEAIQTVLN KHDILLVADE VVTGFGRLGT MFGSDHYGLE PDIITIAKGL TSAYAPLSGS    300

IVSDKVWKVL EQGTDENGPI GHGWTYSAHP IGAAAGVANL KLLDELNLVS NAGEVGAYLN    360

ATMAEALSQH ANVGDVRGEG LLCAVEFVKD RDSRTFFDAA DKIGPQISAK LLEQDKIIAR    420

AMPQGDILGF APPFCLTRAE ADQVVEGTLR AVKAVLG                             457

3FCR Y59W/T231A/I234M: amino acid (SEQ ID NO: 23)
MLKNDQLDQW DRDNFFHPST HLAQHARGES ANRVIKTASG VFIEDRDGTK LLDAFAGLWC     60

VNVGYGRQEI AEAIADQARE LAYYHSYVGH GTEASITLAK MILDRAPKNM SKVYFGLGGS    120

DANETNVKLI WYYNNILGRP EKKKIISRWR GYHGSGLVTG SLTGLELFHK KFDLPVEQVI    180

HTEAPYYFRR EDLNQTEEQF VAHCVAELEA LIEREGADTI AAFIGEPILG AGGMVPPPAG    240

YWEAIQTVLN KHDILLVADE VVTGFGRLGT MFGSDHYGLE PDIITIAKGL TSAYAPLSGS    300

IVSDKVWKVL EQGTDENGPI GHGWTYSAHP IGAAAGVANL KLLDELNLVS NAGEVGAYLN    360

ATMAEALSQH ANVGDVRGEG LLCAVEFVKD RDSRTFFDAA DKIGPQISAK LLEQDKIIAR    420

AMPQGDILGF APPFCLTRAE ADQVVEGTLR AVKAVLG                             457

3GJU Y59W/Y87F/T231A: amino acid (SEQ ID NO: 24)
MLNQSNELNA WDRDHFFHPS THMGTHARGE SPTRIMAGGE GVTVWDNNGR KSIDAFAGLW     60

CVNVGYGRQK IADAIATQAK NLAYYHAFVG HGTEASITLA KMIIDRAPKG MSRVYFGLSG    120

SDANETNIKL IWYYNNVLGR PEKKKIISRW RGYHGSGVMT GSLTGLDLFH NAFDLPRAPV    180

LHTEAPYYFR RTDRSMSEEQ FSQHCADKLE EMILAEGPET IAAFIGEPIL GAGGIVPPPA    240

GYWEKIQAVL KKYDVLLVAD EVVTGFGRLG TMFGSDHYGI KPDLITIAKG LTSAYAPLSG    300

VIVADRVWQV LVQGSDKLGS LGHGWTYSAH PICVAAGVAN LELIDEMDLV TNAGETGAYF    360

RAELAKAVGG HKNVGEVRGD GMLAAVEFVA DKDDRVFFDA SQKIGPQVAT ALAASGVIGR    420

AMPQGDILGF APPLCLTREQ ADIVVSKTAD AVKSVFANL                           459
```

| SEQUENCES |
|---|

3GJU Y59W/Y87L/T231A: amino acid (SEQ ID NO: 25)
```
MLNQSNELNA WDRDHFFHPS THMGTHARGE SPTRIMAGGE GVTVWDNNGR KSIDAFAGLW    60
CVNVGYGRQK IADAIATQAK NLAYYHALVG HGTEASITLA KMIIDRAPKG MSRVYFGLSG   120
SDANETNIKL IWYYNNVLGR PEKKKIISRW RGYHGSGVMT GSLTGLDLFH NAFDLPRAPV   180
LHTEAPYYFR RTDRSMSEEQ FSQHCADKLE EMILAEGPET IAAFIGEPIL GAGGIVPPPA   240
GYWEKIQAVL KKYDVLLVAD EVVTGFGRLG TMFGSDHYGI KPDLITIAKG LTSAYAPLSG   300
VIVADRVWQV LVQGSDKLGS LGHGWTYSAH PICVAAGVAN LELIDEMDLV TNAGETGAYF   360
RAELAKAVGG HKNVGEVRGD GMLAAVEFVA DKDDRVFFDA SQKIGPQVAT ALAASGVIGR   420
AMPQGDILGF APPLCLTREQ ADIVVSKTAD AVKSVFANL                         459
```

3GJU Y59W/Y87V/T231A: amino acid (SEQ ID NO: 26)
```
MLNQSNELNA WDRDHFFHPS THMGTHARGE SPTRIMAGGE GVTVWDNNGR KSIDAFAGLW    60
CVNVGYGRQK IADAIATQAK NLAYYHAVVG HGTEASITLA KMIIDRAPKG MSRVYFGLSG   120
SDANETNIKL IWYYNNVLGR PEKKKIISRW RGYHGSGVMT GSLTGLDLFH NAFDLPRAPV   180
LHTEAPYYFR RTDRSMSEEQ FSQHCADKLE EMILAEGPET IAAFIGEPIL GAGGIVPPPA   240
GYWEKIQAVL KKYDVLLVAD EVVTGFGRLG TMFGSDHYGI KPDLITIAKG LTSAYAPLSG   300
VIVADRVWQV LVQGSDKLGS LGHGWTYSAH PICVAAGVAN LELIDEMDLV TNAGETGAYF   360
RAELAKAVGG HKNVGEVRGD GMLAAVEFVA DKDDRVFFDA SQKIGPQVAT ALAASGVIGR   420
AMPQGDILGF APPLCLTREQ ADIVVSKTAD AVKSVFANL                         459
```

3GJU Y59W/Y87F/T231G: amino acid (SEQ ID NO: 27)
```
MLNQSNELNA WDRDHFFHPS THMGTHARGE SPTRIMAGGE GVTVWDNNGR KSIDAFAGLW    60
CVNVGYGRQK IADAIATQAK NLAYYHAFVG HGTEASITLA KMIIDRAPKG MSRVYFGLSG   120
SDANETNIKL IWYYNNVLGR PEKKKIISRW RGYHGSGVMT GSLTGLDLFH NAFDLPRAPV   180
LHTEAPYYFR RTDRSMSEEQ FSQHCADKLE EMILAEGPET IAAFIGEPIL GGGGIVPPPA   240
GYWEKIQAVL KKYDVLLVAD EVVTGFGRLG TMFGSDHYGI KPDLITIAKG LTSAYAPLSG   300
VIVADRVWQV LVQGSDKLGS LGHGWTYSAH PICVAAGVAN LELIDEMDLV TNAGETGAYF   360
RAELAKAVGG HKNVGEVRGD GMLAAVEFVA DKDDRVFFDA SQKIGPQVAT ALAASGVIGR   420
AMPQGDILGF APPLCLTREQ ADIVVSKTAD AVKSVFANL                         459
```

3GJU Y59W/T231A/I234F: amino acid (SEQ ID NO: 28)
```
MLNQSNELNA WDRDHFFHPS THMGTHARGE SPTRIMAGGE GVTVWDNNGR KSIDAFAGLW    60
CVNVGYGRQK IADAIATQAK NLAYYHAYVG HGTEASITLA KMIIDRAPKG MSRVYFGLSG   120
SDANETNIKL IWYYNNVLGR PEKKKIISRW RGYHGSGVMT GSLTGLDLFH NAFDLPRAPV   180
LHTEAPYYFR RTDRSMSEEQ FSQHCADKLE EMILAEGPET IAAFIGEPIL GAGGFVPPPA   240
GYWEKIQAVL KKYDVLLVAD EVVTGFGRLG TMFGSDHYGI KPDLITIAKG LTSAYAPLSG   300
VIVADRVWQV LVQGSDKLGS LGHGWTYSAH PICVAAGVAN LELIDEMDLV TNAGETGAYF   360
RAELAKAVGG HKNVGEVRGD GMLAAVEFVA DKDDRVFFDA SQKIGPQVAT ALAASGVIGR   420
AMPQGDILGF APPLCLTREQ ADIVVSKTAD AVKSVFANL                         459
```

3GJU Y59W/T231A/I234M: amino acid (SEQ ID NO: 29)
```
MLNQSNELNA WDRDHFFHPS THMGTHARGE SPTRIMAGGE GVTVWDNNGR KSIDAFAGLW    60
CVNVGYGRQK IADAIATQAK NLAYYHAYVG HGTEASITLA KMIIDRAPKG MSRVYFGLSG   120
SDANETNIKL IWYYNNVLGR PEKKKIISRW RGYHGSGVMT GSLTGLDLFH NAFDLPRAPV   180
LHTEAPYYFR RTDRSMSEEQ FSQHCADKLE EMILAEGPET IAAFIGEPIL GAGGMVPPPA   240
```

| SEQUENCES |
|---|
| GYWEKIQAVL KKYDVLLVAD EVVTGFGRLG TMFGSDHYGI KPDLITIAKG LTSAYAPLSG    300 |
| VIVADRVWQV LVQGSDKLGS LGHGWTYSAH PICVAAGVAN LELIDEMDLV TNAGETGAYF    360 |
| RAELAKAVGG HKNVGEVRGD GMLAAVEFVA DKDDRVFFDA SQKIGPQVAT ALAASGVIGR    420 |
| AMPQGDILGF APPLCLTREQ ADIVVSKTAD AVKSVFANL                           459 |

Sequences of 4-fold Mutants:
3FCR Y59W/Y87F/Y152F/T231A: amino acid as in FIG. 3 (SEQ ID NO: 30)

3GJU Y59W/Y87F/Y152F/T231A: amino acid as in FIG. 3 (SEQ ID NO: 31)

ATA-3 Y59W/Y87F/Y152F/T231A: amino acid as in FIG. 3 (SEQ ID NO: 32)

ATA-4 Y59W/Y87F/Y152F/T231A: amino acid as in FIG. 3 (SEQ ID NO: 33)

ATA-5 Y59W/Y87F/Y152F/T231A: amino acid as in FIG. 3 (SEQ ID NO: 34)

ATA-6 Y59W/Y87F/Y152F/T231A: amino acid as in FIG. 3 (SEQ ID NO: 35)

ATA-7 Y59W/Y87F/Y152F/T231A: amino acid as in FIG. 3 (SEQ ID NO: 36)

ATA-8 Y59W/Y87F/Y152F/T231A: amino acid as in FIG. 3 (SEQ ID NO: 37)

ATA-9 Y59W/Y87F/Y152F/T231A: amino acid as in FIG. 3 (SEQ ID NO: 38)

3FCR Y59W/Y87L/Y152F/T231A: amino acid (SEQ ID NO: 39)
| |
|---|
| MLKNDQLDQW DRDNFFHPST HLAQHARGES ANRVIKTASG VFIEDRDGTK LLDAFAGLWC    60 |
| VNVGYGRQEI AEAIADQARE LAYYHSLVGH GTEASITLAK MILDRAPKNM SKVYFGLGGS   120 |
| DANETNVKLI WYYNNILGRP EKKKIISRWR GFHGSGLVTG SLTGLELFHK KFDLPVEQVI   180 |
| HTEAPYYFRR EDLNQTEEQF VAHCVAELEA LIEREGADTI AAFIGEPILG AGGIVPPPAG   240 |
| YWEAIQTVLN KHDILLVADE VVTGFGRLGT MFGSDHYGLE PDIITIAKGL TSAYAPLSGS   300 |
| IVSDKVWKVL EQGTDENGPI GHGWTYSAHP IGAAAGVANL KLLDELNLVS NAGEVGAYLN   360 |
| ATMAEALSQH ANVGDVRGEG LLCAVEFVKD RDSRTFFDAA DKIGPQISAK LLEQDKIIAR   420 |
| AMPQGDILGF APPFCLTRAE ADQVVEGTLR AVKAVLG                           457 |

3FCR Y59W/Y87F/T231A/P423H: amino acid (SEQ ID NO: 40)
| |
|---|
| MLKNDQLDQW DRDNFFHPST HLAQHARGES ANRVIKTASG VFIEDRDGTK LLDAFAGLWC    60 |
| VNVGYGRQEI AEAIADQARE LAYYHSFVGH GTEASITLAK MILDRAPKNM SKVYFGLGGS   120 |
| DANETNVKLI WYYNNILGRP EKKKIISRWR GYHGSGLVTG SLTGLELFHK KFDLPVEQVI   180 |
| HTEAPYYFRR EDLNQTEEQF VAHCVAELEA LIEREGADTI AAFIGEPILG AGGIVPPPAG   240 |
| YWEAIQTVLN KHDILLVADE VVTGFGRLGT MFGSDHYGLE PDIITIAKGL TSAYAPLSGS   300 |
| IVSDKVWKVL EQGTDENGPI GHGWTYSAHP IGAAAGVANL KLLDELNLVS NAGEVGAYLN   360 |
| ATMAEALSQH ANVGDVRGEG LLCAVEFVKD RDSRTFFDAA DKIGPQISAK LLEQDKIIAR   420 |
| AMHQGDILGF APPFCLTRAE ADQVVEGTLR AVKAVLG                           457 |

3GJU Y59W/Y87L/Y152F/T231A: amino acid (SEQ ID NO: 41)
| |
|---|
| MLNQSNELNA WDRDHFFHPS THMGTHARGE SPTRIMAGGE GVTVWDNNGR KSIDAFAGLW    60 |
| CVNVGYGRQK IADAIATQAK NLAYYHALVG HGTEASITLA KMIIDRAPKG MSRVYFGLSG   120 |
| SDANETNIKL IWYYNNVLGR PEKKKIISRW RGYHGSGVMT GSLTGLDLFH NAFDLPRAPV   180 |
| LHTEAPYYFR RTDRSMSEEQ FSQHCADKLE EMILAEGPET IAAFIGEPIL GAGGIVPPPA   240 |
| GYWEKIQAVL KKYDVLLVAD EVVTGFGRLG TMFGSDHYGI KPDLITIAKG LTSAYAPLSG   300 |
| VIVADRVWQV LVQGSDKLGS LGHGWTYSAH PICVAAGVAN LELIDEMDLV TNAGETGAYF   360 |

| SEQUENCES |
|---|

RAELAKAVGG HKNVGEVRGD GMLAAVEFVA DKDDRVFFDA SQKIGPQVAT ALAASGVIGR    420

AMPQGDILGF APPLCLTREQ ADIVVSKTAD AVKSVFANL                         459

3GJU Y59W/Y87F/T231A/P423H: amino acid (SEQ ID NO: 42)
MLNQSNELNA WDRDHFFHPS THMGTHARGE SPTRIMAGGE GVTVWDNNGR KSIDAFAGLW   60

CVNVGYGRQK IADAIATQAK NLAYYHAFVG HGTEASITLA KMIIDRAPKG MSRVYFGLSG    120

SDANETNIKL IWYYNNVLGR PEKKKIISRW RGYHGSGVMT GSLTGLDLFH NAFDLPRAPV    180

LHTEAPYYFR RTDRSMSEEQ FSQHCADKLE EMILAEGPET IAAFIGEPIL GAGGIVPPPA    240

GYWEKIQAVL KKYDVLLVAD EVVTGFGRLG TMFGSDHYGI KPDLITIAKG LTSAYAPLSG    300

VIVADRVWQV LVQGSDKLGS LGHGWTYSAH PICVAAGVAN LELIDEMDLV TNAGETGAYF    360

RAELAKAVGG HKNVGEVRGD GMLAAVEFVA DKDDRVFFDA SQKIGPQVAT ALAASGVIGR    420

AMHQGDILGF APPLCLTREQ ADIVVSKTAD AVKSVFANL                         459

Sequences of 5-fold Mutants:
3FCR Y59W/Y87F/Y152F/T231A/P423H: amino acid as in FIG. 4 (SEQ ID NO: 43)

3GJU Y59W/Y87F/Y152F/T231A/P423H: amino acid as in FIG. 4 (SEQ ID NO: 44)

ATA-3 Y59W/Y87F/Y152F/T231A/P423H: amino acid as in FIG. 4 (SEQ ID NO: 45)

ATA-4 Y59W/Y87F/Y152F/T231A/P423H: amino acid as in FIG. 4 (SEQ ID NO: 46)

ATA-5 Y59W/Y87F/Y152F/T231A/P423H: amino acid as in FIG. 4 (SEQ ID NO: 47)

ATA-6 Y59W/Y87F/Y152F/T231A/P423H: amino acid as in FIG. 4 (SEQ ID NO: 48)

ATA-7 Y59W/Y87F/Y152F/T231A/P423H: amino acid as in FIG. 4 (SEQ ID NO: 49)

ATA-8 Y59W/Y87F/Y152F/T231A/P423H: amino acid as in FIG. 4 (SEQ ID NO: 50)

ATA-9 Y59W/Y87F/Y152F/T231A/P423H: amino acid as in FIG. 4 (SEQ ID NO: 51)

3FCR Y59W/Y87F/Y152F/T231A/1234M: amino acid as in FIG. 5 (SEQ ID NO: 53)

3GJU Y59W/Y87F/Y152F/T231A/1234M: amino acid as in FIG. 5 (SEQ ID NO: 55)

ATA-3 Y59W/Y87F/Y152F/T231A/1234M: amino acid as in FIG. 5 (SEQ ID NO: 58)

ATA-4 Y59W/Y87F/Y152F/T231A/1234M: amino acid as in FIG. 5 (SEQ ID NO: 59)

ATA-5 Y59W/Y87F/Y152F/T231A/1234M: amino acid as in FIG. 5 (SEQ ID NO: 60)

ATA-6 Y59W/Y87F/Y152F/T231A/1234M: amino acid as in FIG. 5 (SEQ ID NO: 61)

ATA-7 Y59W/Y87F/Y152F/T231A/1234M: amino acid as in FIG. 5 (SEQ ID NO: 62)

ATA-8 Y59W/Y87F/Y152F/T231A/1234M: amino acid as in FIG. 5 (SEQ ID NO: 63)

ATA-9 Y59W/Y87F/Y152F/T231A/1234M: amino acid as in FIG. 5 (SEQ ID NO: 64)

3FCR Y59W/Y87F/Y152F/T231A/I234F: amino acid (SEQ ID NO: 52)
MLKNDQLDQW DRDNFFHPST HLAQHARGES ANRVIKTASG VFIEDRDGTK LLDAFAGLWC    60

VNVGYGRQEI AEAIADQARE LAYYHSFVGH GTEASITLAK MILDRAPKNM SKVYFGLGGS    120

DANETNVKLI WYYNNILGRP EKKKIISRWR GFHGSGLVTG SLTGLELFHK KFDLPVEQVI    180

HTEAPYYFRR EDLNQTEEQF VAHCVAELEA LIEREGADTI AAFIGEPILG AGGFVPPPAG    240

YWEAIQTVLN KHDILLVADE VVTGFGRLGT MFGSDHYGLE PDIITIAKGL TSAYAPLSGS    300

IVSDKVWKVL EQGTDENGPI GHGWTYSAHP IGAAAGVANL KLLDELNLVS NAGEVGAYLN    360

ATMAEALSQH ANVGDVRGEG LLCAVEFVKD RDSRTFFDAA DKIGPQISAK LLEQDKIIAR    420

AMPQGDILGF APPFCLTRAE ADQVVEGTLR AVKAVLG                           457

| SEQUENCES |
|---|
| GJU Y59W/Y87F/Y152F/T231A/I234F: amino acid (SEQ ID NO: 54) | | | | | |
| MLNQSNELNA WDRDHFFHPS THMGTHARGE SPTRIMAGGE GVTVWDNNGR KSIDAFAGL<u>W</u> | 60 |
| CVNVGYGRQK IADAIATQAK NLAYYHA<u>F</u>VG HGTEASITLA KMIIDRAPKG MSRVYFGLSG | 120 |
| SDANETNIKL IWYYNNVLGR PEKKKIISRW RG<u>F</u>HGSGVMT GSLTGLDLFH NAFDLPRAPV | 180 |
| LHTEAPYYFR RTDRSMSEEQ FSQHCADKLE EMILAEGPET IAAFIGEPIL G<u>A</u>GG<u>F</u>VPPPA | 240 |
| GYWEKIQAVL KKYDVLLVAD EVVTGFGRLG TMFGSDHYGI KPDLITIAKG LTSAYAPLSG | 300 |
| VIVADRVWQV LVQGSDKLGS LGHGWTYSAH PICVAAGVAN LELIDEMDLV TNAGETGAYF | 360 |
| RAELAKAVGG HKNVGEVRGD GMLAAVEFVA DKDDRVFFDA SQKIGPQVAT ALAASGVIGR | 420 |
| AMPQGDILGF APPLCLTREQ ADIVVSKTAD AVKSVFANL | 459 |

REFERENCES

Coffen D. L., Okabe M., Sun R. C., Lee S. & Matcham G. W. J. (1994) Aminotransferase Catalysis Applied to the Synthesis of a PAF Antagonist. *Bioorg. Med. Chem.* 2, 411-413.

Deszcz D., Affacati P., Ladkau N., Gegel A., Ward J. M., Hailes H. C., Dalby P. A. (2015) Single active-site mutants are sufficient to enhance serine:pyruvate α-transaminase activity in an ω-transaminase. *FEBS J* DOI:1111/febs.13293

Nobili, A., Steffen-Munsberg, F., Kohls, H., Trentin, I., Schulzke, C., Höhne, M., Bornscheuer, U. T. (2015) Engineering the active site of the amine-transaminase from *Vibrio fluvialis* for the asymmetric synthesis of aryl-alkyl amines and amino alcohols, Chem Cat Chem, 7, 757-760.

Pearson W. R., Lipman D. J. (1988) Improved tools for biological sequence comparison. *Proc Natl Acad Sci USA*, 85, 2444-2448.

Savile C. K., Janey J. M., Mundorff E. C., Moore J. C., Tam S., Jarvis W. R., Colbeck J. C., Krebber A., Fleitz F. J., Brands J., Devine P. N., Huisman G. W. & Hughes G. J. (2010) Biocatalytic Asymmetric Synthesis of Chiral Amines from Ketones Applied to Sitagliptin Manufacture. *Science* 329, 305-309.

Schätzle, S., Höhne, M., Redestad, E., Robins, K., Bornscheuer U. T. (2009), A rapid and sensitive kinetic assay for characterization of omega-transaminases, *Anal. Chem*, 81, 8244-8248

Steffen-Munsberg F., Vickers C., Thontowi A., Schätzle S., Meinhardt T., Svedendahl Humble M., Land H., Berglund P., Bornscheuer U. T., Höhne M. (2013) Revealing the Structural Basis of Promiscuous Amine Transaminase Activity. *Chem Cat Chem*, 5, 154-157.

US 2015/0037869 A1

Weiß, M. S., Pavlidis, I. V., Vickers, C., Höhne, M., Bornscheuer, U. T. (2014), A glycine oxidase based high-throughput solid-phase-assay for substrate profiling and directed evolution of (R)- and (S)-selective amine transaminases, *Anal. Chem*, 86, 11847-11853.

The invention claimed is:

1. A mutant transaminase with increased transaminase activity relative to the wild-type transaminase having the amino acid sequence shown in SEQ ID NO:1, wherein the mutant transaminase comprises an amino acid sequence that is at least 65% identical to the amino acid sequence of SEQ ID NO: 1 (*Ruegeria* sp. TM1040 transaminase; referred to as 3FCR) and wherein the mutant transaminase has at least two amino acid substitutions relative to the wild-type transaminase having the amino acid sequence of SEQ ID NO:1, wherein the amino acid at the position corresponding to position 59 of SEQ ID NO: 1 is substituted with Trp or Phe (Trp59 or Phe59, respectively) and the amino acid at the position corresponding to position 231 of SEQ ID NO: 1 is substituted with Ala or Gly (Ala231 or Gly231, respectively).

2. The mutant transaminase of claim 1, wherein said mutant transaminase has at least one substitution selected from the group consisting of:
   (a) the amino acid at the position corresponding to position 87 of SEQ ID NO: 1 is substituted with a hydrophobic amino acid (HYaa87) selected from the group consisting of Leu (Leu87), Val (Val87), and Phe (Phe87);
   (b) the amino acid at the position corresponding to position 152 of SEQ ID NO: 1 is substituted with Phe (Phe152);
   (c) the amino acid at the position corresponding to position 234 of SEQ ID NO: 1 is substituted with Phe (Phe234) or Met (Met234); and
   (d) wherein the amino acid at the position corresponding to position 423 of SEQ ID NO: 1 is substituted with His (His423).

3. The mutant transaminase of claim 1, wherein the transaminase has one or more mutations selected from the group consisting of:
   (a) Trp59 and Ala231;
   (b) Trp59, Phe87 and Ala231;
   (c) Trp59, Leu87 and Ala231;
   (d) Trp59, Val87 and Ala231;
   (e) Trp59, Phe87, Ala231 and His423;
   (f) Trp59, Phe87, Phe152 and Ala231;
   (g) Trp59, Leu87, Phe152 and Ala231;
   (h) Trp59, Val87, Phe152 and Ala231;
   (i) Trp59, Phe87, Phe152, Ala231 and His423;
   (j) Trp59 and Gly231;
   (k) Trp59, Phe87 and Gly231;
   (l) Trp59, Leu87 and Gly231;
   (m) Trp59, Val87 and Gly231;
   (n) Trp59, Phe87, Phe152 and Gly231;
   (o) Trp59, Phe87, Phe152, Gly231 and His423;
   (p) Phe59 and Ala231;
   (q) Phe59, Phe87 and Gly231;
   (r) Trp59, Ala231 and Phe234;
   (s) Trp59, Ala231 and Met234;
   (t) Trp59, Phe87, Ala231 and Phe234;
   (u) Trp59, Leu87, Ala231 and Phe234;
   (v) Trp59, Val87, Ala231 and Phe234;
   (w) Trp59, Phe87, Phe152, Ala231 and Phe234;
   (x) Trp59, Phe87, Phe152, Ala231, Phe234 and His423;
   (y) Trp59, Gly231 and Phe234;
   (z) Trp59, Phe87, Gly231 and Phe234;
   (aa) Trp59, Leu87, Gly231 and Phe234;
   (bb) Trp59, Val87, Gly231 and Phe234;
   (cc) Trp59, Phe87, Phe152, Gly231 and Phe234;
   (dd) Trp59, Phe87, Phe152, Gly231, Phe234 and His423;
   (ee) Phe59, Phe87, Gly231 and Phe234;
   (ff) Trp59, Ala231 and Met234;
   (gg) Trp59, Phe87, Ala231 and Met234;
   (hh) Trp59, Leu87, Ala231 and Met234;
   (ii) Trp59, Val87, Ala231 and Met234;
   (jj) Trp59, Phe87, Phe152, Ala231 and Met234;
   (kk) Trp59, Phe87, Phe152, Ala231, Met234 and His423;
   (ll) Trp59, Gly231 and Met234;
   (mm) Trp59, Phe87, Gly231 and Met234;
   (nn) Trp59, Leu87, Gly231 and Met234;
   (oo) Trp59, Val87, Gly231 and Met234;
   (pp) Trp59, Phe87, Phe152, Gly231 and Met234;
   (qq) Trp59, Phe87, Phe152, Gly231, Met234 and His423; and
   (rr) Phe59, Phe87, Gly231 and Met234.

4. The mutant transaminase of claim 1 wherein the transaminase has at least one set of mutations selected from the group consisting of:
   (a) Trp59, Phe87, Phe152 and Ala231;
   (b) Trp59, Phe87, Phe152, Ala231 and Met234;
   (c) Trp59, Phe87, Phe152, Ala231 and H423; and
   (d) Phe59, Phe87 and Gly231.

5. The mutant transaminase of claim 1, wherein the transaminase comprises a sequence selected from the group consisting of SEQ ID NOs: 30-38, SEQ ID NOS:43, 44, 46-51, SEQ ID NO:53, SEQ ID NO:55 and SEQ ID NOS: 57-64.

6. The mutant transaminase of claim 1, wherein the mutant transaminase comprises an amino acid sequence that is at least 70%, identical to an amino acid sequence selected from the group consisting of: SEQ ID NOs: 1, 3, and 5-11.

7. The mutant transaminase of claim 1, wherein the mutant transaminase has increased transaminase activity for transamination of at least one compound selected from the group consisting of: 1-(4-chlorophenyl)-1-phenyl-1-aminomethane (1a); 2,2-dimethyl-1-phenyl-1-amino propane (2a); 1,3-diphenyl-1-aminopropane (3a); 1,2-dihydroacenaphthylen-1-amine (4a); 3-amino-8-benzoyl-8-azabicyclo [3.2.1]octane (5a); 3(4-chlorophenyl)-phenyl-methanone (1b); 2,2-dimethyl-1-phenyl-propan-1-one (2b) 1,3-diphenylpropan-1-one (3b); 2H-acenaphthylen-1-one (4b), 8-benzoyl-8-azabicyclo[3.2.1]octan-3-one (5b); and iso-propylamine when compared with the transaminase activity of the wild type transaminase having the sequence of SEQ ID NO:1.

8. The mutant transaminase of claim 7, wherein the mutant transaminase has an at least 2-fold increased transaminase activity relative to the wild type enzyme having the amino acid sequence of SEQ ID NO:1.

9. A fusion protein comprising the transaminase of claim 1.

10. A nucleic acid coding for the transaminase of claim 1.

11. A host cell comprising the polynucleotide of claim 10.

12. A method of producing an amine comprising reacting an amine acceptor with the mutant transaminase of claim 1 or the fusion protein of claim 9 in the presence of an amine donor.

13. The method of claim 12 wherein an enantiomerically enriched chiral amine is produced and the method is an asymmetric transamination of a prochiral ketone in the presence of an amine donor and the mutant transaminase or the fusion protein, wherein the mutant transaminase or the fusion protein is stereoselective.

14. The method of claim 12 wherein an enantiomerically enriched chiral amine is produced and the method is a kinetic resolution of a racemic amine in the presence of an amine acceptor and the mutant transaminase or the fusion protein.

15. The method of claim 14, wherein the racemic amine has the formula

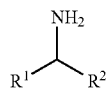   I wherein
R¹ or R² independently of each other represent optionally substituted alkyl, aryl, carbocyclyl or heterocyclyl; or
R¹ and R² together with the carbon atom they are attached to form an optionally substituted mono- or poly-cyclic carbocyclic or heterocyclic ring.

16. The method of claim 14 wherein the amine acceptor is selected from ketones and keto carboxylic acids.

17. The method of claim 13, wherein the prochiral ketone has the formula

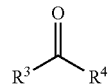   II wherein
R³ or R⁴ independently of each other represent optionally substituted alkyl, aryl, carbocyclyl or heterocyclyl or;
R³ and R⁴ together with the carbon atom they are attached to form an optionally substituted mono- or poly-cyclic carbocyclic or heterocyclic ring.

18. The method of claim 13, wherein the amine donor is an achiral or chiral amine or amino acid.

19. The method of claim 15 wherein the amine acceptor is selected from ketones and keto carboxylic acids.

20. The method of claim 17, wherein the amine donor is an achiral or chiral amine or amino acid.

\* \* \* \* \*